United States Patent [19]
Kuno et al.

[11] Patent Number: 5,824,691
[45] Date of Patent: Oct. 20, 1998

[54] GUANIDINE DERIVATIVES AS INHIBITORS OF $NA^+/H^+$ EXCHANGE IN CELLS

[75] Inventors: Atsushi Kuno, Toyono-gun; Yoshikazu Inoue, Amagasaki; Hisashi Takasugi, Sakai; Hiroaki Mizuno, Osaka; Kumi Yamasaki, Nishinomiya, all of Japan

[73] Assignee: Fujisawa Pharmaceutical Co., Ltd., Osaka, Japan

[21] Appl. No.: 532,804

[22] PCT Filed: May 12, 1994

[86] PCT No.: PCT/JP94/00786

§ 371 Date: Nov. 9, 1995

§ 102(e) Date: Nov. 9, 1995

[87] PCT Pub. No.: WO94/26709

PCT Pub. Date: Nov. 24, 1994

[30] Foreign Application Priority Data

May 17, 1993 [GB] United Kingdom ............ 9310074
Dec. 10, 1993 [GB] United Kingdom ............ 9325268

[51] Int. Cl.⁶ .................. A61K 31/34; A61K 31/38; A61K 31/40; A61K 31/535
[52] U.S. Cl. .................. 514/335.5; 514/256; 514/357; 514/364; 514/365; 514/381; 514/427; 514/429; 514/438; 514/471; 544/141; 544/335; 546/332; 548/143; 548/204; 548/253; 548/560; 548/561; 548/563; 548/577; 549/61; 549/77; 549/474; 549/493
[58] Field of Search ................ 548/563, 577, 548/143, 204, 253, 560, 561; 514/427, 429, 235.9, 256, 357, 364, 365, 381, 438, 471; 544/141, 335; 546/332; 549/61, 77, 474, 493

[56] References Cited

U.S. PATENT DOCUMENTS 3,574,527  4/1971  Walz et al. .
4,251,545  2/1981  Resnick .
5,364,868  11/1994 Englert et al. ................ 514/445

FOREIGN PATENT DOCUMENTS 59-106993  6/1984  Japan .

OTHER PUBLICATIONS

Chemical Abstract 121:133971 for Chinese Patent 1075960 (Sep. 8, 1993).
Englert, Chemical Abstract 120:106777 for EP 556672 (Aug. 25, 1993).
Englert, Chemical Abstract 115:71158 for DE 3929582 (Mar. 7, 1991).

*Primary Examiner*—Richard L. Raymond
*Attorney, Agent, or Firm*—Oblon, Spivak, McClelland, Maier & Neustadt, P.C.

[57] ABSTRACT

Guanidine derivatives of the formula:

$$\text{(I)}$$

wherein
  Y is C—$R^1$
    (in which $R^1$ is hydrogen, lower alkyl, hydroxy, protected hydroxy, etc.,)
  $R^2$ is pyrrolyl, tetrazolyl, pyrazolyl, etc.,
  $R^3$ is hydrogen, lower alkoxy, hydroxy, protected hydroxy, etc.,
  Z is C—$R^4$
    (in which $R^4$ is hydrogen, carboxy, protected carboxy, nitro, halogen, hydroxy(lower)alkyl, etc.,), and
  W is $R^{12}$
    (in which $R^{12}$ is hydrogen, lower alkoxy, nitro, hydroxy or protected hydroxy)
and pharmaceutically acceptable salts thereof which are useful as a medicament which are useful in inhibiting $Na^+/H^+$ exchange in cells and in the prevention of cardiovascular diseases, cerebrovascular diseases, renal diseases, arteriosclerosis and shock.

12 Claims, No Drawings

GUANIDINE DERIVATIVES AS INHIBITORS OF NA+/H+ EXCHANGE IN CELLS

This application is a 371 of PCT/JP94/00786, filed May 12, 1994.

TECHNICAL FIELD

This invention relates to new guanidine derivatives and a pharmaceutically acceptable salts thereof which are useful as a medicament.

DISCLOSURE OF INVENTION

This invention relates to new guanidine derivatives. More particularly, this invention relates to new guanidine derivatives and pharmaceutically acceptable salts thereof which have pharmacological activities, processes for preparation thereof, a pharmaceutical composition comprising the same and a use of the same.

Accordingly, one object of this invention is to provide the new and useful guanidine derivatives and pharmaceutically acceptable salts thereof which possess a strong inhibitory activity on Na+/H+ exchange in cells.

Another object of this invention is to provide processes for preparation of the guanidine derivatives and salts thereof.

A further object of this invention is to provide a pharmaceutical composition comprising said guanidine derivatives or a pharmaceutically acceptable salt thereof.

Still further object of this invention is to provide a use of said guanidine derivatives or a pharmaceutically acceptable salt thereof as a medicament for the treatment and/or prevention of cardiovascular diseases, cerebrovascular diseases, renal diseases, arteriosclerosis, shock and the like in human being and animals.

The object guanidine derivatives of the present invention are novel and can be represented by the following general formula (I):

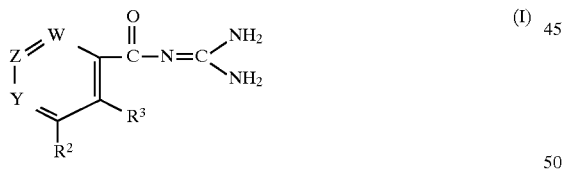

wherein

Y is N or C—R$^1$
(in which R$^1$ is hydrogen, lower alkyl, hydroxy, protected hydroxy, lower alkoxy, hydroxy(lower)alkyl, protected hydroxy(lower)alkyl, amino(lower)alkyl, protected amino(lower)alkyl, carboxy(lower)alkoxy, protected carboxy(lower)alkoxy, hydroxy(lower)alkoxy, protected hydroxy(lower)alkoxy, acyl, aryl or heterocyclic group), R$^2$ is hydrogen, aryl which may have one suitable substituent, aryloxy, mono(or di or tri)halo(lower)alkyl, acyl, heterocyclic group which may have suitable substituent(s) or heterocyclic(lower)alkyl, R$^3$ is hydrogen, lower alkoxy, hydroxy, protected hydroxy or heterocyclic group, or R$^1$ and R$^2$ are linked together to form a bivalent radical of

or

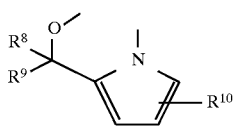

(in which
R$^8$ is hydrogen or lower alkyl,
R$^9$ is hydrogen or lower alkyl, and
R$^{10}$ is hydrogen, cyano or di(lower)alkylamino (lower)alkyl), or R$^2$ and R$^3$ are linked together to form a bivalent radical of

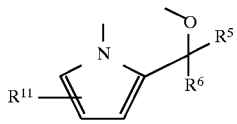

(in which
R$^5$ is hydrogen or lower alkyl,
R$^6$ is hydrogen or lower alkyl, and
R$^{11}$ is hydrogen or cyano), Z is N or C—R$^4$
(in which R$^4$ is hydrogen, carboxy, protected carboxy, nitro, halogen, hydroxy(lower)alkyl, protected hydroxy(lower)alkyl, amino, protected amino, cyano, lower alkoxy(lower)alkyl, carboxy(lower) alkenyl, protected carboxy(lower)alkenyl, hydroxy, protected hydroxy, di(lower)alkylamino(lower) alkyl, amino(lower)alkyl, protected amino(lower) alkyl, hydroxy(lower)alkoxy, protected hydroxy (lower)alkoxy, hydroxyimino(lower)alkyl, heterocyclic group, heterocyclic(lower)alkyl which may have suitable substituent(s) or acyl), and W is N or C—R$^{12}$
(in which R$^{12}$ is hydrogen, lower alkoxy, nitro, hydroxy or protected hydroxy).

The object compound (I) of the present invention can be prepared by the following process.

Process (1)

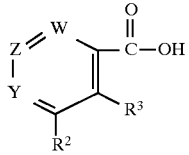

(II)
or its reactive derivative at the carboxy group, or a salt thereof

-continued
Process (1)

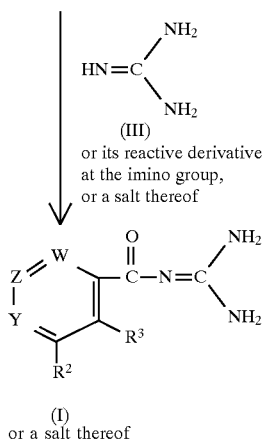
(III)
or its reactive derivative
at the imino group,
or a salt thereof

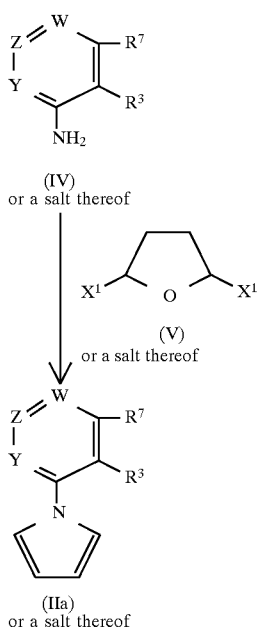
(I)
or a salt thereof wherein

R$^2$, R$^3$, W, Y and Z are each as defined above.

The starting compound (II) can be prepared by the following processes or Preparations mentioned below, or similar manners thereto.

Process (A)

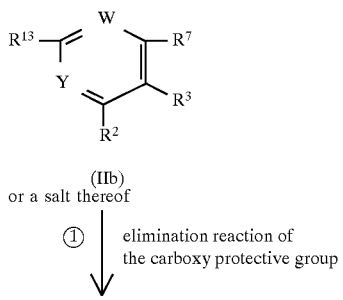

Process (B)

-continued
Process (B)

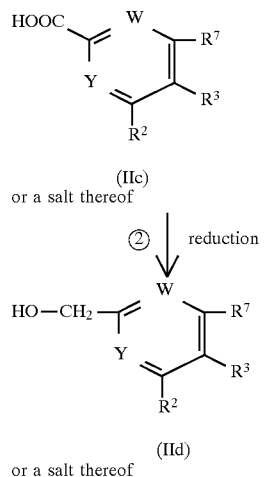
(IIc)
or a salt thereof

② ↓ reduction

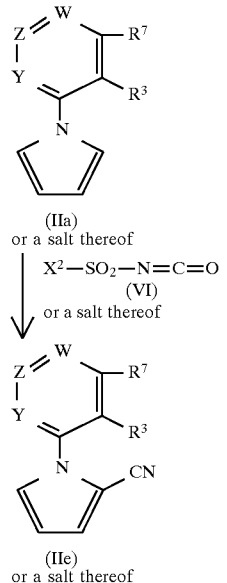
(IId)
or a salt thereof

Process (C)

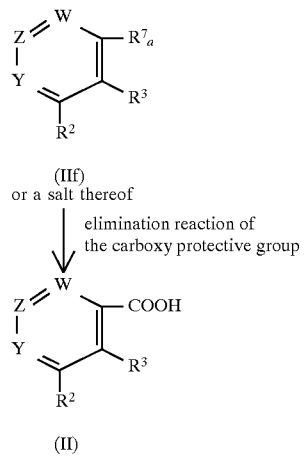

Process (D)

-continued

Process (D)

or a salt thereof

Process (E)

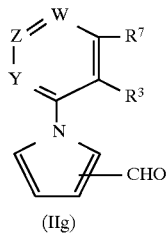

(IIg)
or a salt thereof $H_2N-OH$ (VII)
or a salt thereof

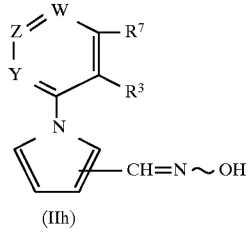

(IIh)
or a salt thereof

Process (F)

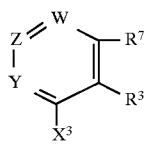

(VIII)
or a salt thereof

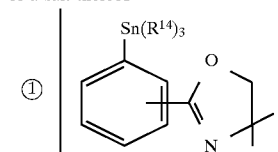

(IX)
or a salt thereof

①

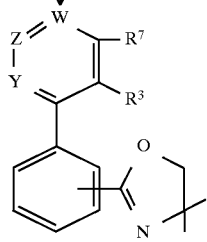

(IIr)
or a salt thereof

② cyanogenation

Process (F)

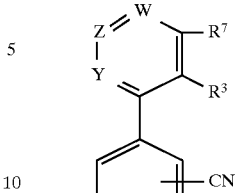

(IIi)
or a salt thereof

Process (G)

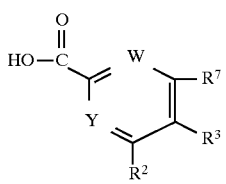

(IIc)
or its reactive derivative at the
carboxy group, or a salt thereof amidation

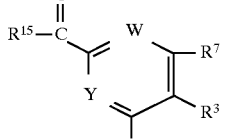

(IIj)
or a salt thereof

Process (H)

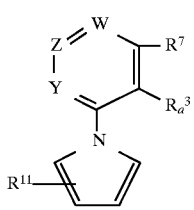

(IIk)
or a salt thereof

① formylation

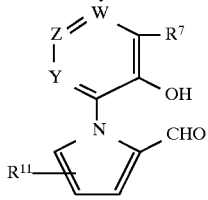

(III)
or a salt thereof

② reduction

Process (H)

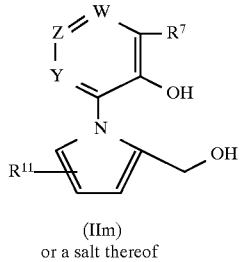

(IIm)
or a salt thereof

Process (I)

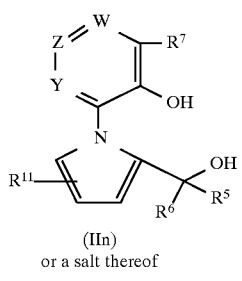

(IIn)
or a salt thereof

↓ cyclization

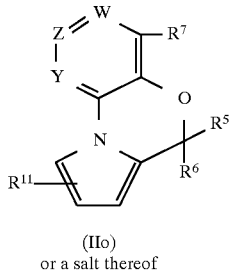

(IIo)
or a salt thereof

Process (J)

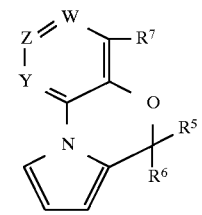

(IIp)
or a salt thereof

↓ cyanogenation

Process (J)

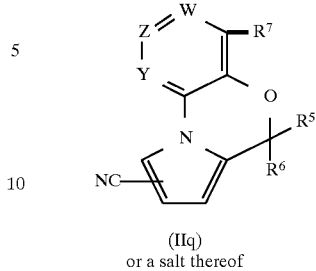

(IIq)
or a salt thereof wherein
$R^2$, $R^3$, $R^5$, $R^6$, $R^{11}$, W, Y and Z are each as defined above,
$R_a^3$ is hydroxy or protected hydroxy,
$R^7$ is carboxy or protected carboxy,
$R_a^7$ is protected carboxy,
$R^{13}$ is protected carboxy,
$R^{14}$ is lower alkyl, a group of the formula:

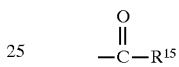

is amidated carboxy, and
$X^1$, $X^2$ and $X^3$ are each a leaving group.

Suitable pharmaceutically acceptable salts of the object compound (I) are conventional non-toxic salts and may include a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, triethanolamine salt, dicyclohexylamine salt, N,N'-dibenzylethylenediamine salt, etc.); an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, citrate, fumarate, isethionate, methanesulfonate, benzenesulfonate, toluenesulfonate, etc.); a salt with a basic or acidic amino acid (e.g., arginine, aspartic acid, glutamic acid, etc.).

In the above and subsequent descriptions of the present specification, suitable examples and illustration of the various definitions which the present invention intends to include within the scope thereof are explained in detail as follows.

The term "lower" is used to intend a group having 1 to 6, preferably 1 to 4, carbon atom(s), unless otherwise provided.

The term "higher" is used to intend a group having 7 to 20 carbon atoms, unless otherwise provided.

Suitable "lower alkyl" and "lower alkyl moiety" in the terms "protected hydroxy(lower)alkyl", "hydroxy(lower)alkyl", "amino(lower)alkyl", "protected amino(lower)alkyl", "heterocyclic(lower)alkyl", "mono(or di or tri)halo(lower)alkyl", "di(lower)alkylamino(lower)alkyl", "hydroxyimino(lower)alkyl" and "lower alkoxy(lower)

alkyl" may include straight or branched one having 1 to 6 carbon atom(s), such as methyl, ethyl, propyl, isopropyl, butyl, isobutyl, sec-butyl, tert-butyl, pentyl, tert-pentyl, hexyl, and the like, preferably one having 1 to 4 carbon atom(s).

Suitable "lower alkenyl" and "lower alkenyl moiety" in the terms "carboxy(lower)alkenyl" and "protected carboxy (lower)alkenyl" may include vinyl, 1-(or 2-)propenyl, 1-(or 2- or 3-)butenyl, 1-(or 2- or 3- or 4-)pentenyl, 1-(or 2- or 3- or 4- or 5-)hexenyl, methylvinyl, ethylvinyl, 1-(or 2- or 3-)methyl-1-(or 2-)propenyl, 1-(or 2- or 3-)ethyl-1-(or 2-)propenyl, 1-(or 2- or 3- or 4-)methyl-1-(or 2- or 3-)butenyl, and the like, in which more preferable example may be $C_2$–$C_4$ alkenyl.

Suitable "lower alkynyl" may include ethynyl, 1-propynyl, propargyl, 1-methylpropargyl, 1 or 2 or 3-butynyl, 1 or 2 or 3 or 4-pentynyl, 1 or 2 or 3 or 4 or 5-hexynyl, and the like.

Suitable "lower alkoxy" and "lower alkoxy moiety" in the terms "lower alkoxy(lower)alkyl", "carboxy(lower)alkoxy", "protected carboxy(lower)alkoxy", "hydroxy(lower) alkoxy" and "protected hydroxy(lower)alkoxy" may include methoxy, ethoxy, propoxy, isopropoxy, butoxy, isobutoxy, t-butoxy, pentyloxy, t-pentyloxy, hexyloxy and the like.

Suitable "cyclo(lower)alkyl" may include cyclopentyl, cyclohexyl and the like.

Suitable "cyclo(lower)alkenyl" may include cyclohexenyl, cyclohexadienyl and the like.

Suitable "protected amino" and "protected amino moiety" in the term "protected amino(lower)alkyl" may include commonly protected amino or the like.

Suitable "commonly protected amino" may include an acylamino or an amino group substituted by a conventional protecting group such as ar(lower)alkyl which may have suitable substituent(s) (e.g., benzyl, trityl, etc.) or the like.

Suitable "acyl" and "acyl moiety" in the term "acylamino" may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

Carbamoyl; Thiocarbamoyl; Sulfamoyl; Aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.); lower or higher alkoxycarbonyl (e.g., methoxycarbonyl, ethoxycarbonyl, t-butoxycarbonyl, t-pentyloxycarbonyl, heptyloxycarbonyl, etc.); lower or higher alkylsulfonyl (e.g., methylsulfonyl, ethylsulfonyl, etc.); lower or higher alkoxysulfonyl (e.g., methoxysulfonyl, ethoxysulfonyl, etc.); mono(or di or tri)halo(lower)alkylsulfonyl [e.g. fluoromethylsulfonyl, difluoromethylsulfonyl, trifluoromethylsulfonyl, chloromethylsulfonyl, dichloromethylsulfonyl, trichloromethylsulfonyl, 1 or 2-fluoroethylsulfonyl, 1 or 2-chloroethylsulfonyl, etc.); or the like;

Aromatic acyl such as
aroyl (e.g., benzoyl, toluoyl, naphthoyl, etc.); ar(lower) alkanoyl [e.g., phenyl(lower)alkanoyl (e.g., phenylacetyl, phenylpropanoyl, phenylbutanoyl, phenylisobutanoyl, phenylpentanoyl, phenylhexanoyl, etc.), naphthyl(lower) alkanoyl (e.g., naphthylacetyl, naphthylpropanoyl, naphthylbutanoyl, etc.), etc.]; ar(lower)alkenoyl [e.g., phenyl(lower)alkenoyl (e.g., phenylpropenoyl, phenylbutenoyl, phenylmethacryloyl, phenylpentenoyl, phenylhexenoyl, etc.), naphthyl(lower)alkenoyl (e.g., naphthylpropenoyl, naphthylbutenoyl, etc.), etc.]; ar(lower)alkoxycarbonyl [e.g., phenyl(lower) alkoxycarbonyl (e.g., benzyloxycarbonyl, etc.), etc.]; aryloxycarbonyl (e.g., phenoxycarbonyl, naphthyloxycarbonyl, etc.); aryloxy(lower)alkanoyl (e.g., phenoxyacetyl, phenoxypropionyl, etc.); arylglyoxyloyl (e.g., phenylglyoxyloyl, naphthylglyoxyloyl, etc.); arylsulfonyl (e.g., phenylsulfonyl, p-tolylsulfonyl, etc.); or the like;

Heterocyclic acyl such as
heterocycliccarbonyl; heterocyclic(lower)alkanoyl (e.g., heterocyclicacetyl, heterocyclicpropanoyl, heterocyclicbutanoyl, heterocyclicpentanoyl, heterocyclichexanoyl, etc.); heterocyclic(lower)alkenoyl (e.g., heterocyclicpropenoyl, heterocyclicbutenoyl, heterocyclicpentenoyl, heterocyclichexenoyl, etc.); heterocyclicglyoxyloyl; or the like;

in which suitable "heterocyclic moiety" in the terms "heterocycliccarbonyl", "heterocyclic(lower)alkyl", heterocyclic(lower)alkenoyl" and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like.

And, especially preferable heterocyclic group may be heterocyclic group such as unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 to 2 oxygen atom(s) and 1 to 3 nitrogen atom(s), for example, oxazoloxazolidinyl, morpholinyl, syndnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2, 3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc.; and the like.

The acyl moiety as stated above may have one to ten, same or different, suitable substituent(s) such as lower alkyl as exemplified above; lower alkoxy as exemplified above; lower alkylthio wherein lower alkyl moiety is as exemplified above; lower alkylamino wherein lower alkyl moiety is as exemplified above; cyclo(lower)alkyl as exemplified above; cyclo(lower)alkenyl as exemplified above; halogen; amino, protected amino as exemplified above; hydroxy; protected hydroxy; cyano; nitro; carboxy; protected carboxy; sulfo; sulfamoyl; imino; oxo; amino(lower)alkyl wherein lower alkyl moiety is as exemplified above; carbamoyloxy; hydroxy(lower)alkyl wherein lower alkyl moiety is as exemplified above; diamino(lower)alkylidene (e.g., diaminomethylene, etc.); di(lower)alkylamino wherein lower alkyl moiety is as exemplified above; di(lower) alkylamino(lower)alkyl wherein lower alkyl moiety is as exemplified above; heterocyclic(lower)alkyl wherein heterocyclic moiety and lower alkyl moiety are each as exemplified above, or the like.

Suitable "aryl" and "aryl moiety" in the term "aryloxy" may include phenyl, naphthyl and the like.

Suitable "leaving group" may include acid residue, lower alkoxy as exemplified above and the like, and suitable examples of "acid residue" may be halogen, acyloxy wherein acyl moiety is as exemplified above or the like.

Suitable "halogen" and "halogen moiety" in the term "mono(or di or tri)halo(lower)alkyl" may include fluorine, bromine, chlorine and iodine.

Suitable "protected carboxy" and "protected carboxy moiety" in the terms "protected carboxy(lower)alkoxy" and "protected carboxy(lower)alkenyl" may include commonly protected carboxy or the like.

Suitable "commonly protected carboxy" may include esterified carboxy and the like. And suitable example of said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, etc.); lower alkenyl ester (e.g., vinyl ester, allyl ester, etc.); lower alkynyl ester (e.g., ethynyl ester, propynyl ester, etc.); lower alkoxy(lower)alkyl ester (e.g., methoxymethyl ester, ethoxymethyl ester, isopropoxymethyl ester, 1-methoxyethyl ester, 1-ethoxyethyl ester, etc.); lower alkylthio(lower)alkyl ester (e.g., methylthiomethyl ester, ethylthiomethyl ester, ethylthioethyl ester, isopropoxythi-omethyl ester, etc.); mono(or di or tri)halo(lower)alkyl ester (e.g., 2-iodoethyl ester, 2,2,2-trichloroethyl ester, etc.); lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 1-acetoxyethyl ester, 2-acetoxyethyl ester, 2-propionyloxyethyl ester, etc.); lower alkoxycarbonyloxy (lower)alkyl ester (e.g., methoxycarbonyloxymethyl ester, ethoxycarbonyloxymethyl ester, propoxycarbonyloxymethyl ester, 1-(or 2-)[methoxycarbonyloxy]ethyl ester, 1-(or 2-)[ethoxycarbonyloxy]ethyl ester, 1-(or 2-)[propoxycarbonyloxy]ethyl ester, 1-(or 2-)[isopropoxycarbonyloxy]ethyl ester, etc.); lower alkanesulfonyl(lower)alkyl ester (e.g., mesylmethyl ester, 2-mesylethyl ester, etc.); lower alkoxycarbonyloxy(lower) alkyl ester (e.g., methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-)isopropoxycarbonyloxyethyl ester, etc.); phthalidylidene (lower)alkyl ester; (5-lower alkyl-2-oxo-1,3-dioxol-4-yl) (lower)alkyl ester [e.g., (5-methyl-2-oxo- 1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.]; mono(or di or tri)aryl(lower)alkyl ester, for example, mono(or di or tri)phenyl(lower)alkyl ester which may have one or more suitable substituent(s) (e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have one or more suitable substituent(s) such as substituted or unsubstituted phenyl ester (e.g., phenyl ester, tolyl ester, t-butylphenyl ester, xylyl ester, mesityl ester, cumenyl ester, 4-chlorophenyl ester, 4-methoxyphenyl ester, etc.); tri(lower)alkyl silyl ester; lower alkylthioester (e.g., methylthioester, ethylthioester, etc.) and the like.

Suitable "hydroxy protective group" in the terms "protected hydroxy", "protected hydroxy(lower)alkoxy" and "protected hydroxy(lower)alkyl" may include commonly protective group or the like.

Suitable "common protective group may include acyl as mentioned above, mono(or di or tri)phenyl(lower)alkyl which may have one or more suitable substituent(s) (e.g., benzyl, 4-methoxybenzyl, trityl, etc.), trisubstituted silyl [e.g., tri(lower)alkylsilyl (e.g., trimethylsilyl, t-butyldimethylsilyl, etc.), etc.], tetrahydropyranyl and the like.

Suitable "heterocyclic group" and "heterocyclic moiety" in the term "heterocyclic(lower)alkyl" can be referred to the ones as exemplified above.

Suitable "substituent" in the term "heterocyclic group which may have suitable substituent(s)" may include lower alkyl as exemplified above, lower alkoxy as exemplified above, lower alkenyl as exemplified above, lower alkynyl as exemplified above, mono(or di or tri)halo(lower)alkyl wherein halogen moiety and lower alkyl moiety are each as exemplified above, cyclo(lower)alkyl as exemplified above, cyclo(lower)alkenyl as exemplified above, halogen as exemplified above, carboxy, protected carboxy as exemplified above, hydroxy, protected hydroxy as exemplified above, aryl as exemplified above, ar(lower)alkyl wherein aryl moiety and lower alkyl moiety are each as exemplified above, carboxy(lower)alkyl wherein lower alkyl moiety is as exemplified above, protected carboxy(lower)alkyl wherein protected carboxy moiety and lower alkyl moiety are each as exemplified above, nitro, amino, protected amino as exemplified above, di(lower)alkylamino wherein lower alkyl moiety is as exemplified above, amino(lower)alkyl wherein lower alkyl moiety is as exemplified above, protected amino (lower)alkyl wherein protected amino moiety and lower alkyl moiety are each as exemplified above, hydroxy(lower) alkyl wherein lower alkyl moiety is as exemplified above, protected hydroxy(lower)alkyl wherein protected hydroxy moiety and lower alkyl moiety are each as exemplified above, acyl as exemplified above, cyano, sulfo, oxo, carbamoyloxy, mercapto, lower alkylthio wherein lower alkyl moiety is as exemplified above, imino, hydroxyimino (lower)alkyl wherein lower alkyl moiety is as exemplified above, lower alkoxyimino(lower)alkyl wherein lower alkoxy moiety and lower alkyl moiety are each as exemplified above, di(lower)alkylamino(lower)alkyl wherein lower alkyl moiety is as exemplified above, carboxy(lower)alkenyl wherein lower alkenyl moiety is as exemplified above, protected carboxy(lower)alkenyl wherein protected carboxy moiety and lower alkenyl moiety are each as exemplified above, and the like.

Suitable "substituent" in the term "aryl which may have one suitable substituent" may include lower alkyl as exemplified above, lower alkoxy as exemplified above, lower alkenyl as exemplified above, lower alkynyl as exemplified above, mono(or di or tri)halo(lower)alkyl wherein halogen moiety and lower alkyl moiety are each as exemplified above, cyclo(lower)alkyl as exemplified above, cyclo (lower)alkenyl as exemplified above, halogen as exemplified above, carboxy, protected carboxy as exemplified above, hydroxy, protected hydroxy as exemplified above, aryl as exemplified above, ar(lower)alkyl wherein aryl moiety and lower alkyl moiety are each as exemplified above, carboxy (lower)alkyl wherein lower alkyl moiety is as exemplified above, protected carboxy(lower)alkyl wherein protected carboxy moiety and lower alkyl moiety are each as exemplified above, nitro, amino, protected amino as exemplified above, di(lower)alkylamino wherein lower alkyl moiety is as exemplified above, amino(lower)alkyl wherein lower alkyl moiety is as exemplified above, protected amino(lower)alkyl wherein protected amino moiety and lower alkyl moiety are each as exemplified above, hydroxy(lower)alkyl wherein lower alkyl moiety is as exemplified above, protected hydroxy(lower)alkyl wherein protected hydroxy moiety and lower alkyl moiety are each as exemplified above, acyl as exemplified above, cyano, sulfo, oxo, carbamoyloxy, mercapto, lower alkylthio wherein lower alkyl moiety is as exemplified above, imino, and the like.

Suitable "substituent" in the term "heterocyclic(lower) alkyl which may have suitable substituent(s)" may include lower alkyl as exemplified above, lower alkoxy as exemplified above, lower alkenyl as exemplified above, lower alkynyl as exemplified above, mono(or di or tri)halo(lower) alkyl wherein halogen moiety and lower alkyl moiety are each as exemplified above, cyclo(lower)alkyl as exemplified above, cyclo(lower)alkenyl as exemplified above, halogen as exemplified above, carboxy, protected carboxy as exemplified above, hydroxy, protected hydroxy as exemplified above, aryl as exemplified above, ar(lower)alkyl wherein aryl moiety and lower alkyl moiety are each as exemplified above, carboxy(lower)alkyl wherein lower alkyl moiety is as exemplified above, protected carboxy(lower)alkyl wherein protected carboxy moiety and lower alkyl moiety are each as exemplified above, nitro, amino, protected amino as exemplified above, di(lower)alkylamino wherein lower alkyl moiety is as exemplified above, amino(lower)alkyl wherein lower alkyl moiety is as exemplified above, protected amino (lower)alkyl wherein protected amino moiety and lower alkyl moiety are each as exemplified above, hydroxy(lower) alkyl wherein lower alkyl moiety is as exemplified above, protected hydroxy(lower)alkyl wherein protected hydroxy moiety and lower alkyl moiety are each as exemplified above, acyl as exemplified above, cyano, sulfo, oxo, carbamoyloxy, mercapto, lower alkylthio wherein lower alkyl moiety is as exemplified above, imino, and the like.

Suitable "amidated carboxy" may include carbamoyl which may have one or two suitable substituent(s), and the like.

Suitable "substituent" in the term "carbamoyl which may have one or two suitable substituent(s)" may include lower alkyl as exemplified above; lower alkoxy as exemplified above; lower alkylthio wherein lower alkyl moiety is as exemplified above; lower alkylamino wherein lower alkyl moiety is as exemplified above; cyclo(lower)alkyl as exemplified above; cyclo(lower)alkenyl as exemplified above; halogen as exemplified above; amino; protected amino as exemplified above; hydroxy; protected hydroxy as exemplified above; cyano; nitro; carboxy; protected carboxy as exemplified above; sulfo; sulfamoyl; imino; oxo; amino (lower)alkyl wherein lower alkyl moiety is as exemplified above; carbamoyloxy; hydroxy(lower)alkyl wherein lower alkyl moiety is as exemplified above; diamino(lower) alkylidene (e.g., diaminomethylene, etc.); di(lower) alkylamino wherein lower alkyl moiety is as exemplified above, di(lower)alkylamino(lower)alkyl wherein lower alkyl moiety is as exemplified above; heterocyclic(lower) alkyl wherein heterocyclic moiety and lower alkyl moiety are each as exemplified above, or the like.

Preferred embodiments of the object compound (I) are as follows:

Y is N or C—R$^1$
(in which R$^1$ is hydrogen, lower alkyl, hydroxy, phenyl (lower)alkoxy (more preferably benzyloxy), lower alkoxy, hydroxy(lower)alkyl, acyloxy(lower)alkyl, amino(lower)alkyl, acylamino(lower)alkyl (more preferably lower alkanoylamino(lower)alkyl), carboxy(lower)alkoxy, esterified carboxy(lower) alkoxy, hydroxy(lower)alkoxy, acyloxy(lower)alkyl, carbamoyl which may have suitable substituent(s) (more preferably diamino(lower)alkylidene) [more preferably diamino(lower)alkylidenecarbamoyl], phenyl, piperidyl or pyrrolyl), R$^2$ is hydrogen; phenyl or naphthyl, each of which may have one suitable substituent (more preferably substituent selected from the group consisting of acyl (more preferably lower alkylsulfonyl or diamino(lower) alkylidenecarbamoyl), mono(or di or tri)halo(lower) alkyl (more preferably trihalo(lower)alkyl), cyano, lower alkyl, lower alkoxy, halogen, nitro and protected amino (more preferably acylamino; most preferably mono(or di or tri)halo(lower)alkylsulfonylamino) [more preferably phenyl, lower alkylsulfonylphenyl, diamino(lower)alkylidenecarbamoylphenyl, trihalo (lower)alkylphenyl, cyanophenyl, lower alkylphenyl, lower alkoxyphenyl, halophenyl, nitrophenyl, trihalo (lower)alkylsulfonylaminophenyl or naphthyl]; phenyloxy; trihalo(lower)alkyl; aroyl (more preferably benzoyl); pyrrolyl, tetrazolyl, pyrazolyl, thienyl, furyl, oxadiazolyl, thiazolyl, pyridyl or pyrimidinyl, each of which may have one to three suitable substituent(s) (more preferably substituent selected from the group consisting of carboxy, protected carboxy (more preferably esterified carboxy; most preferably diphenyl (lower)alkoxycarbonyl), acyl (more preferably lower alkanoyl or carbamoyl), lower alkyl, halogen, hydroxyimino, (lower)alkyl, lower alkoxyimino(lower) alkyl, di(lower)alkylamino(lower)alkyl, cyano, amino, protected amino (more preferably acylamino), carboxy (lower)alkenyl, protected carboxy(lower)alkenyl (more preferably esterified carboxy(lower)alkenyl; most preferably lower alkoxycarbonyl(lower)alkenyl), carboxy (lower)alkyl and protected carboxy(lower)alkyl (more preferably esterified carboxy(lower)alkyl) [more preferably pyrrolyl which may have one to three substituent (s) selected from the group consisting of carboxy, diphenyl(lower)alkoxycarbonyl, lower alkanoyl, carbamoyl, lower alkyl, halogen, hydroxyimino(lower) alkyl, lower alkoxyimino(lower)alkyl, di(lower) alkylamino(lower)alkyl, cyano, carboxy(lower) alkenyl, lower alkoxycarbonyl(lower)alkenyl and carboxy(lower)alkyl (more preferably pyrrolyl, carboxypyrrolyl, diphenyl(lower) alkoxycarbonylpyrrolyl, lower alkanoylpyrrolyl, carbamoylpyrrolyl, mono(or di)(lower)alkylpyrrolyl, hydroxyimino(lower)alkylpyrrolyl, lower alkoxyimino (lower)alkylpyrrolyl, [di(lower)alkylamino(lower) alkyl]pyrrolyl, cyanopyrrolyl, carboxy(lower) alkenylpyrrolyl, lower alkoxycarbonyl(lower) alkenylpyrrolyl, carboxy(lower)alkylpyrrolyl, dihalopyrrolyl, pyrrolyl having lower alkyl and cyano, pyrrolyl having di(lower)alkylamino(lower)alkyl and cyano, pyrrolyl having two lower alkyl and cyano); tetrazolyl; pyrazolyl which may have amino; thienyl which may have cyano; furyl which may have cyano; oxadiazolyl which may have lower alkyl (more preferably lower alkyloxadiazolyl); thiazolyl; pyridyl or pyrimidinyl]; or pyrrolyl(lower)alkyl, $R^3$ is hydrogen, lower alkoxy, hydroxy, acyloxy or pyrrolyl, or $R^1$ and $R^2$ are linked together to form a bivalent radical of

or

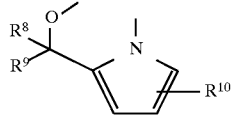

(in which
$R^8$ is hydrogen or lower alkyl,
$R^9$ is hydrogen or lower alkyl, and
$R^{10}$ is hydrogen, cyano or di(lower)alkylamino (lower)alkyl), or $R^2$ and $R^3$ are linked together to form a bivalent radical of

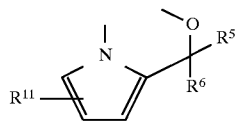

(in which
$R^5$ is hydrogen or lower alkyl,
$R^6$ is hydrogen or lower alkyl, and
$R^{11}$ is hydrogen or cyano), Z is N or C—$R^4$ (in which $R^4$ is hydrogen; carboxy; esterified carboxy (more preferably lower alkoxycarbonyl); nitro; halogen; hydroxy(lower)alkyl; acyloxy(lower)alkyl; amino; acylamino [more preferably mono(or di or tri)halo(lower)alkylsulfonylamino (more preferably trihalo(lower)alkylsulfonylamino), di(lower) alkylamino(lower)alkanoylamino or heterocyclic (lower)alkanoylamino (more preferably morpholinyl (lower)alkanoylamino)]; cyano; lower alkoxy (lower)alkyl; carboxy(lower)alkenyl; esterified carboxy(lower)alkenyl; hydroxy; acyloxy; di(lower) alkylamino(lower)alkyl; amino(lower)alkyl; acylamino(lower)alkyl; hydroxy(lower)alkoxy; acyloxy(lower)alkoxy; hydroxyimino(lower)alkyl; pyrrolyl; tetrazolyl; oxazolidinyl(lower)alkyl which may have suitable substituent(s) (more preferably oxo) [more preferably oxazolidinyl(lower)alkyl having oxo]; lower alkylsulfonyl; lower alkanoyl; carbamoyl which may have one or two substituent(s) selected from the group consisting of lower alkyl, diamino(lower)alkylidene, di(lower)alkylamino (lower)alkyl and heterocyclic(lower)alkyl (more preferably morpholinyl(lower)alkyl) [more preferably di(lower)alkylcarbamoyl, diamino(lower) alkylidenecarbamoyl, di(lower)alkylamino(lower) alkylcarbamoyl or morpholinyl(lower) alkylcarbamoyl]; sulfamoyl; or heterocycliccarbonyl (more preferably piperidylcarbonyl or piperazinylcarbonyl) which may have hydroxy, protected hydroxy (more preferably acyloxy) or lower alkyl [more preferably hydroxypiperidylcarbonyl or lower alkylpiperazinylcarbonyl], and W is N or C—$R^{12}$
(in which $R^{12}$ is hydrogen, lower alkoxy, nitro, hydroxy or acyloxy).

More preferred embodiments of the object compound (I) are represented by the following general formulas (A)–(C):

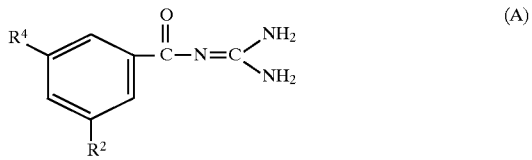

(in which
$R^2$ is hydrogen; phenyl or naphthyl, each of which may have one suitable substituent (more preferably substituent selected from the group consisting of acyl (more preferably lower alkylsulfonyl or diamino(lower) alkylidenecarbamoyl), mono(or di or tri)halo(lower) alkyl (more preferably trihalo(lower)alkyl), cyano, lower alkyl, lower alkoxy, halogen, nitro and protected amino (more preferably acylamino; most preferably mono(or di or tri)halo(lower)alkylsulfonylamino) [more preferably phenyl, lower alkylsulfonylphenyl, diamino(lower)alkylidenecarbamoylphenyl, trihalo (lower)alkylphenyl, cyanophenyl, lower alkylphenyl, lower alkoxyphenyl, halophenyl, nitrophenyl, trihalo (lower)alkylsulfonylaminophenyl or naphthyl]; phenyloxy; trihalo(lower)alkyl; aroyl(more preferably benzoyl); pyrrolyl, tetrazolyl, pyrazolyl, thienyl, furyl, oxadiazolyl, thiazolyl, pyridyl or pyrimidinyl, each of which may have one to three suitable substituent(s) (more preferably substituent selected from the group consisting of carboxy, protected carboxy (more preferably esterified carboxy; most preferably diphenyl (lower)alkoxycarbonyl), acyl (more preferably lower alkanoyl or carbamoyl), lower alkyl, halogen, hydroxyimino(lower)alkyl, lower alkoxyimino(lower) alkyl, di(lower)alkylamino(lower)alkyl, cyano, amino, protected amino (more preferably acylamino), carboxy (lower)alkenyl, protected carboxy(lower)alkenyl (more preferably esterified carboxy(lower)alkenyl; most preferably lower alkoxycarbonyl(lower)alkenyl), carboxy (lower)alkyl and protected carboxy(lower)alkyl (more preferably esterified carboxy(lower)alkyl) [more preferably pyrrolyl which may have one to three substituent (s) selected from the group consisting of carboxy, diphenyl(lower)alkoxycarbonyl, lower alkanoyl, carbamoyl, lower alkyl, halogen, hydroxyimino(lower) alkyl, lower alkoxyimino(lower)alkyl, di(lower) alkylamino(lower)alkyl, cyano, carboxy(lower) alkenyl, lower alkoxycarbonyl(lower)alkenyl and carboxy(lower)alkyl (more preferably pyrrolyl, carboxypyrrolyl, diphenyl(lower) alkoxycarbonylpyrrolyl, lower alkanoylpyrrolyl, carbamoylpyrrolyl, mono(or di)(lower)alkylpyrrolyl, hydroxyimino(lower)alkylpyrrolyl, lower alkoxyimino (lower)alkylpyrrolyl, [di(lower)alkylamino(lower) alkyl]pyrrolyl, cyanopyrrolyl, carboxy(lower) alkenylpyrrolyl, lower alkoxycarbonyl(lower) alkenylpyrrolyl, carboxy(lower)alkylpyrrolyl, dihalopyrrolyl, pyrrolyl having lower alkyl and cyano, pyrrolyl having di(lower)alkylamino(lower)alkyl and cyano, pyrrolyl having two lower alkyl and cyano); tetrazolyl; pyrazolyl which may have amino; thienyl which may have cyano; furyl which may have cyano; oxadiazolyl which may have lower alkyl (more preferably lower alkyloxadiazolyl); thiazolyl; pyridyl or pyrimidinyl]; or pyrrolyl(lower)alkyl, and R⁴ is hydrogen; carboxy; esterified carboxy (more preferably lower alkoxycarbonyl); nitro; halogen; hydroxy (lower)alkyl; acyloxy(lower)alkyl; amino; acylamino [more preferably mono(or di or tri)halo(lower) alkylsulfonylamino (more preferably trihalo(lower) alkylsulfonylamino), di(lower)alkylamino(lower) alkanoylamino or heterocyclic(lower)alkanoylamino (more preferably morpholinyl(lower)alkanoylamino)]; cyano; lower alkoxy(lower)alkyl; carboxy(lower) alkenyl; esterified carboxy(lower)alkenyl; hydroxy; acyloxy; di(lower)alkylamino(lower)alkyl; amino (lower)alkyl; acylamino(lower)alkyl; hydroxy(lower) alkoxy; acyloxy(lower)alkoxy; hydroxyimino(lower) alkyl; pyrrolyl; tetrazolyl; oxazolidinyl(lower)alkyl which may have suitable substituent(s) (more preferably oxo) [more preferably oxazolidinyl(lower)alkyl having oxo]; lower alkylsulfonyl; lower alkanoyl; carbamoyl which may have one or two substituent(s) selected from the group consisting of lower alkyl, diamino(lower)alkylidene, di(lower)alkylamino(lower) alkyl and heterocyclic(lower)alkyl (more preferably morpholinyl(lower)alkyl) [more preferably di(lower) alkylcarbamoyl, diamino(lower)alkylidenecarbamoyl, di(lower)alkylamino(lower)alkylcarbamoyl, morpholinyl(lower)alkylcarbamoyl]; sulfamoyl; or heterocycliccarbonyl (more preferably piperidylcarbonyl or piperazinylcarbonyl) which may have hydroxy, protected hydroxy (more preferably acyloxy) or lower alkyl [more preferably hydroxypiperidylcarbonyl or lower alkylpiperazinylcarbonyl]),

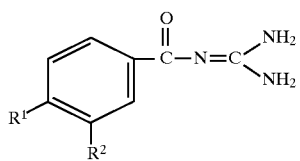

(in which

R¹ is hydrogen, lower alkyl, hydroxy, phenyl(lower) alkoxy (more preferably benzyloxy), lower alkoxy, hydroxy(lower)alkyl, acyloxy(lower)alkyl, amino (lower)alkyl, acylamino(lower)alkyl (more preferably lower alkanoylamino(lower)alkyl), carboxy(lower) alkoxy, esterified carboxy(lower)alkoxy, hydroxy (lower)alkoxy, acyloxy(lower)alkyl, carbamoyl which may have suitable substituent(s) (more preferably diamino(lower)alkylidene) [more preferably diamino (lower)alkylidenecarbamoyl], phenyl, piperidyl or pyrrolyl, R² is hydrogen; phenyl or naphthyl, each of which may have one suitable substituent (more preferably substituent selected from the group consisting of acyl (more preferably lower alkylsulfonyl or diamino(lower) alkylidenecarbamoyl), mono(or di or tri)halo(lower) alkyl (more preferably trihalo(lower)alkyl), cyano, lower alkyl, lower alkoxy, halogen, nitro and protected amino (more preferably acylamino; most preferably mono(or di or tri)halo(lower)alkylsulfonylamino) [more preferably phenyl, lower alkylsulfonylphenyl, diamino(lower)alkylidenecarbamoylphenyl, trihalo (lower)alkylphenyl, cyanophenyl, lower alkylphenyl, lower alkoxyphenyl, halophenyl, nitrophenyl, trihalo (lower)alkylsulfonylaminophenyl or naphthyl]; phenyloxy; trihalo(lower)alkyl; aroyl (more preferably benzoyl); pyrrolyl, tetrazolyl, pyrazolyl, thienyl, furyl, oxadiazolyl, thiazolyl, pyridyl or pyrimidinyl, each of which may have one to three suitable substituent(s) (more preferably substituent selected from the group consisting of carboxy, protected carboxy (more preferably esterified carboxy; most preferably diphenyl (lower)alkoxycarbonyl), acyl (more preferably lower alkanoyl or carbamoyl), lower alkyl, halogen, hydroxyimino(lower)alkyl, lower alkoxyimino(lower) alkyl, di(lower)alkylamino(lower)alkyl, cyano, amino, protected amino (more preferably acylamino), carboxy (lower)alkenyl, protected carboxy(lower)alkenyl (more preferably esterified carboxy(lower)alkenyl; most preferably lower alkoxycarbonyl(lower)alkenyl), carboxy (lower)alkyl and protected carboxy(lower)alkyl (more preferably esterified carboxy(lower)alkyl) [more preferably pyrrolyl which may have one to three substituent (s) selected from the group consisting of carboxy, diphenyl(lower)alkoxycarbonyl, lower alkanoyl, carbamoyl, lower alkyl, halogen, hydroxyimino(lower) alkyl, lower alkoxyimino(lower)alkyl, di(lower) alkylamino(lower)alkyl, cyano, carboxy(lower) alkenyl, lower alkoxycarbonyl(lower)alkenyl and carboxy(lower)alkyl (more preferably pyrrolyl, carboxypyrrolyl, diphenyl(lower) alkoxycarbonylpyrrolyl, lower alkanoylpyrrolyl, carbamoylpyrrolyl, mono(or di)(lower)alkylpyrrolyl, hydroxyimino(lower)alkylpyrrolyl, lower alkoxyimino (lower)alkylpyrrolyl, di(lower)alkylamino(lower) alkylpyrrolyl, cyanopyrrolyl, carboxy(lower) alkenylpyrrolyl, lower alkoxycarbonyl(lower) alkenylpyrrolyl, carboxy(lower)alkylpyrrolyl, dihalopyrrolyl, pyrrolyl having lower alkyl and cyano, pyrrolyl having di(lower)alkylamino(lower)alkyl and cyano, pyrrolyl, having two lower alkyl and cyano); tetrazolyl; pyrazolyl which may have amino; thienyl which may have cyano; furyl which may have cyano; oxadiazolyl which may have lower alkyl (more preferably lower alkyloxadiazolyl); thiazolyl; pyridyl or pyrimidinyl]; or pyrrolyl(lower)alkyl), and

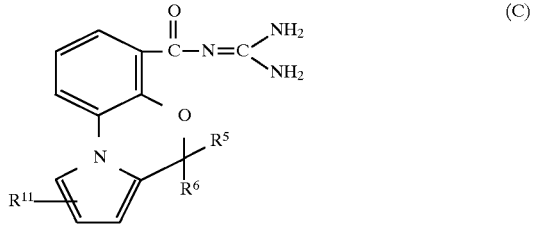

(C)

(in which
R5 is hydrogen or lower alkyl,
$R^6$ is hydrogen or lower alkyl, and
$R^{11}$ is hydrogen or cyano).

The processes for preparing the object and starting compounds of the present invention are explained in detail in the following.

Process (1)

The compound (I) or a salt thereof can be prepared by reacting the compound (II) or its reactive derivative at the carboxy group, or a salt thereof with the compound (III) or its reactive derivative at the imino group, or a salt thereof.

Suitable reactive derivative at the imino group of the compound (III) may include a silyl derivative formed by the reaction of the compound (III) with a silyl compound such as bis(trimethylsilyl)acetamide, mono(trimethylsilyl) acetamide [e.g. N-(trimethylsilyl)acetamide], bis (trimethylsilyl)urea or the like; a derivative formed by reaction of the compound (III) with phosphorus trichloride or phosgene, and the like.

Suitable reactive derivative at the carboxy group of the compound (II) may include a conventional one such as an acid halide, an acid anhydride, an activated amide, an activated ester, and the like.

Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 1-hydroxy-1H-benzotriazole, 4-substituted imidazole, dimethylpyrazole, triazole or tetrazole; or an activated ester [e.g. cyanomethyl ester, methyl ester, ethyl ester, methoxymethyl ester, dimethyliminomethyl $[(CH_3)_2 \overset{+}{N}=CH—]$ ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, benzothiazolyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)pyridone, N-hydroxysuccinimide, N-hydroxyphthalimide, 1-hydroxy-1H-benzotriazole, etc.], and the like. These reactive derivatives can optionally be selected from them according to the kind of the compound (II) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (II) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonyl-bis(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl) isoxazollum hydroxide intramolecular salt; 1-(p-chlorobenzenesulfonyloxy-6-chloro-1H-benzotriazole; a combination of N-lower alkylhalopyridinum halide (e.g., 1-methyl-2-chloropyridinium iodide, etc.) and tri(lower) alkylamine (e.g. triethylamine, etc.); so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine (e.g. triethylamine, etc.), pyridine, N-(lower)alkylmorpholine, N,N-di(lower) alkylbenzylamine, alkali metal lower alkoxide (e.g. sodium methoxide, etc.) or the like.

The reaction temperature is not critical, and the reaction is usually carried out under cooling to warming.

Process (A)

The compound (IIa) or a salt thereof can be prepared by reacting the compound (IV) or a salt thereof with the compound (V) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvent which does not adversely affect the reaction. These conventional solvent may also be used in a mixture with water.

The reaction temperature is not critical and the reaction is usually carried out under warming to heating.

The reaction is usually carried out in the presence of an acid including Lewis acid.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, zinc halide (e.g. zinc chloride, zinc bromide, etc.), etc.] and the like.

When the acid and/or the starting compound are in liquid, they can be used also as a solvent.

Process (B)—①

The compound (IIc) or a salt thereof can be prepared by subjecting the compound (IIb) or a salt thereof to elimination reaction of the carboxy protective group.

This reaction can be carried out in the manner disclosed in Preparation 56 or similar manners thereto.

Process (B)—②

The compound (IId) or a salt thereof can be prepared by subjecting the compound (IIc) or a salt thereof to reduction reaction.

This reaction can be carried out in the manner disclosed in Preparation 52 or similar manners thereto.

Process (C)

The compound (IIe) or a salt thereof can be prepared by reacting the compound (IIa) or a salt thereof with the compound (VI) or a salt thereof.

The reaction can be carried out in the manner disclosed in Preparations 37 and 38 or similar manners thereto.

Process (D)

The compound (II) or a salt thereof can be prepared by subjecting the compound (IIf) or a salt thereof to elimination reaction of the carboxy protective group.

This reaction can be carried out in the manner disclosed in Preparation 45 or similar manners thereto.

Process (E)

The compound (IIh) or a salt thereof can be prepared by reacting the compound (IIg) or a salt thereof with the compound (VII) or a salt thereof.

The reaction can be carried out in the manners disclosed in Preparations 32 and 34 or similar manners thereto.

Process (F)—①

The compound (IIr) or a salt thereof can be prepared by reacting the compound (VIII) or a salt thereof with the compound (IX) or a salt thereof.

The reaction can be carried out in the manner disclosed in Preparation 26 or similar manners thereto.

Process (F)—②

The compound (IIi) or a salt thereof can be prepared by subjecting the compound (IIr) or a salt thereof to cyanogenation reaction.

The reaction can be carried out in the manner disclosed in Preparation 28 or similar manners thereto.

Process (G)

The compound (IIj) or a salt thereof can be prepared by subjecting the compound (IIc) or its reactive derivative at the carboxy group or a salt thereof to amidation reaction.

Suitable amidation reagent to be used in the present amidation reaction may include a compound of the formula:

$$H-R^{15} \qquad (X)$$

(wherein $R^{15}$ is as defined above) or its reactive derivative or a salt thereof, and the like.

Suitable reactive derivative of the compound (X) may include Schiff's base type imino or its tautomeric enamine type isomer formed by the reaction of the compound (X) with a carbonyl compound such as aldehyde, ketone or the like; a silyl derivative formed by the reaction of the compound (X) with a silyl compound such as bis(trimethylsilyl)acetamide, mono(trimethylsilyl)acetamide [e.g. N-(trimethylsilyl)acetamide], bis(trimethylsilyl)urea or the like; a derivative formed by reaction of the compound (X) with phosphorus trichloride or phosgene, and the like.

Suitable reactive derivative at the carboxy group of the compound (IIc) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl

ester, vinyl ester, ethyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.] or an ester with a N-hydroxy compound [e.g. N,N-dimethyl hydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (IIc) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, toluene, ethyl acetate, N,N-dimethylformamide, pyridine or any other organic solvent which does not adversely influence the reaction. These conventional solvent may also be used in a mixture with water. When the base and/or the starting compound are in liquid, they can be used also as a solvent.

In this reaction, when the compound (IIc) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonyl-bis(2-methylimidazole); pentamethyleneketene-N-cyclohexylimine; diphenylketene-N-cyclohexylimine; ethoxyacetylene; 1-alkoxy-1-chloroethylene; trialkyl phosphite, ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine or the like.

The reaction temperature is not critical, and the reaction is usually carried out under cooling to heating.

Process (H)—①

The compound (III) or a salt thereof can be prepared by subjecting the compound (IIk) or a salt thereof to formylation reaction.

The reaction can be carried out in the manner disclosed in Preparation 118 or similar manners thereto.

Process (H)—②

The compound (IIm) or a salt thereof can be prepared by subjecting the compound (III) or a salt thereof to reduction reaction.

The reaction can be carried out in the manner disclosed in Preparation 119 or similar manners thereto.

Process (I)

The compound (IIo) or a salt thereof can be prepared by subjecting the compound (IIn) or a salt thereof to cyclization reaction.

The reaction can be carried out in the manner disclosed in Preparation 120 or similar manners thereto.

Process (J)

The compound (IIq) or a salt thereof can be prepared by subjecting the compound (IIp) or a salt thereof to cyanogenation reaction.

The reaction can be carried out in the manners disclosed in Preparations 37 and 38 or similar manners thereto.

Suitable salts of the object and starting compounds and their reactive derivatives in Processes (1) and (A)~(J) can be referred to the ones as exemplified for the compound (I).

The new guanidine derivatives (I) and a pharmaceutically acceptable salt thereof of the present invention possess a strong inhibitory activity on $Na^+/H^+$ exchange in cells and therefore are useful as an inhibitor on $Na^+/H^+$ exchange in cells.

Accordingly, the new guanidine derivatives (I) and a pharmaceutically acceptable salt thereof can be used for the treatment and/or prevention of cardiovascular diseases [e.g. hypertension, angina pectoris, myocardial infarction, heart failure (e.g. congestive heart failure, acute heart failure, cardiac hypertrophy, etc.), arrhythmia (e.g. ischemic arrhythmia, arrhythmia due to myocardial infarction, arrhythmia after PTCA or after thrombolysis, etc.), restenosis after PTCA, etc.], cerebrovascular diseases [e.g. ischemic stroke, hemorrhagic stroke, etc.], renal diseases [e.g. diabetic nephropathy, ischemic acute renal failure, etc.], arteriosclerosis, shock [e.g. hemorrhagic shock, endotoxin shock, etc.] and the like, and can also be used as an agent for myocardial protection, organ protection in organ transplantation, open heart surgery, and the like.

In order to show the utilities of the guanidine derivatives (I) and a pharmaceutically acceptable salt thereof of the present invention, pharmacological test data of the representative compound of the guanidine derivatives (I) are illustrated in the following.

[1] Test Compound (a) 2-[3-Methylsulfonyl-5-(pyrrol-1-yl)benzoyl]guanidine

[2] Inhibitory activity on $Na^+/H^+$ exchange in cells

[i] Test Method

Procedure was carried out according to a similar manner to the method described in Enzymology 173, 777 (1989).

Cell preparation

One male SD strain weighing 250–300 g was sacrificed with the blow on the head. Then, the thymus was removed into ice-cold NaCl medium (140 mM sodium chloride, 1 mM potassium chloride, 1 mM calcium chloride, 1 mM magnesium chloride, 10 mM glucose and 20 mM N-2-hydroxyethylpiperazine-N'-2-ethanesulfonic acid (HEPES) - - - pH 7.3), cut in small fragments, and transferred to glass homogenizer. The cells were dissociated by gentle strokes, and the resulting suspension was filtrated through six layers of surgical gauze and the filtrate was centrifuged at 4° C. at 1000 g for 5 minutes. The pellet was resuspended in RPMI 1640 medium (pH 7.3) at room temperature to adjust final cell concentration ($1 \times 10^7$ cells/ml).

Assay

This method detects the swelling that accompanies activation of $Na^+/H^+$ exchanger in cells incubated with sodium propionate. Propionic acid rapidly penetrates through the membrane. Intracellular dissociation brings about cytoplasmic acidification and consequently activation of $Na^+/H^+$ exchanger, which exchange extracellular $Na^+$ for cytoplasmic $H^+$. The uptake of osmotically obliged water is manifested as cell swelling.

Cell sizing and counting were performed electrically with the Coulter Counter-Channelyzer (AT-II). 0.1 ml Thymocytes solution were suspended in 20 ml sodium-propionate medium (140 mM sodium propionate, 1 mM potassium chloride, 1 mM calcium chloride, 1 mM magnesium chloride, 10 mM glucose, 20 mM N-2-hydroxyethylpiperazine-N'-2-ethanesulfonic acid (HEPES) - - - pH 6.8) including test compound solved in dimethyl sulfoxide (final concentration of dimethyl sulfoxide was 0.1%). During 4 minutes, increase of cell volume induced by $Na^+/H^+$ exchanger was kept linear, and the time course of swelling was observed each minute after the addition of thymocytes. Rate of Swelling (volume/min.) was measured by using 3–5 concentrations of test compound. Then, apparent Ki value of test compound was calculated by using Line weaver-Burk plot.

[3] Test Result

| Test compound | Ki (M) |
| --- | --- |
| (a) | $<1.0 \times 10^{-7}$ |

The object compound (I) or its pharmaceutically acceptable salts can usually be administered to mammals including human being in the form of a conventional pharmaceutical composition such as oral dosage form (e.g., capsule, microcapsule, tablet, granule, powder, troche, syrup, aerosol, inhalation, suspension, emulsion, etc.), injection dosage form, suppository, ointment, or the like.

The pharmaceutical composition of this invention can contain various organic or inorganic carrier materials, which are conventionally used for pharmaceutical purpose such as excipient (e.g., sucrose, starch, mannit, sorbit, lactose, glucose, cellulose, talc, calcium phosphate, calcium carbonate, etc.), binding agent (e.g., cellulose, methyl cellulose, hydroxypropylcellulose, polypropylpyrrolidone, gelatin, gum arabic, polyethyleneglycol, sucrose, starch, etc.), disintegrator (e.g., starch, carboxymethyl cellulose, calcium salt of carboxymethyl cellulose, hydroxypropylstarch, sodium glycolestarch, sodium bicarbonate, calcium phosphate, calcium citrate, etc.), lubricant (e.g., magnesium stearate, talc, sodium laurylsulfate, etc.), flavoring agent (e.g., citric acid, mentol, glycine, orange powders, etc.), preservative (e.g., sodium benzoate, sodium bisulfite, methylparaben, propylparaben, etc.), stabilizer (e.g., citric acid, sodium citrate, acetic acid, etc.), suspending agent (e.g., methyl cellulose, polyvinylpyrrolidone, aluminum stearate, etc.), dispersing agent, aqueous diluting agent (e.g., water, etc.), base wax (e.g., cacao butter, polyethyleneglycol, white petrolatum, etc.).

The effective ingredient may usually be administered with a unit dose of 0.01 mg/kg to 500 mg/kg, 1 to 4 times a day. However, the above dosage may be increased or decreased according to age, weight, conditions of the patient or the administering method.

The following Preparations and Examples are given for the purpose of illustrating the present invention in more detail.

Preparation 1

To the mixture of conc. sulfuric acid (53.3 ml) and conc. nitric acid (36.0 ml) was added dropwise a solution of 4-chloro-3-methylsulfonylbenzoic acid (22.5 g) in conc. sulfuric acid (135.0 ml) for 10 minutes at 20°–30° C., and the mixture was stirred for 5 hours at 75°–80° C. After ice-cooling, the mixture was poured into ice-water and isolated precipitate was collected by filtration to give 4-chloro-3-methylsulfonyl-5-nitrobenzoic acid (24.85 g).

mp: 196° C.

IR (Nujol): 1690, 1535, 1320, 1140 $cm^{-1}$

NMR (DMSO-$d_6$, δ): 3.52 (3H, s), 8.69 (1H, d, J=2.0 Hz), 8.80 (1H, d, J=2.0 Hz), 14.25 (1H, br s)

Preparation 2

The mixture of 4-chloro-3-methylsulfonyl-5-nitrobenzoic acid (10.0 g) and conc. sulfuric acid (5.0 ml) in methanol (100.0 ml) was heated under reflux for 10 hours and the mixture was evaporated in vacuo. To the residue was added water and the mixture was adjusted to pH 8 with potassium carbonate. The mixture was extracted with a mixture of ethyl acetate and tetrahydrofuran. The extract was washed with brine, dried over magnesium sulfate and evaporated in vacuo. The residue was triturated with diisopropyl ether to give methyl 4-chloro-3-methylsulfonyl-5-nitrobenzoate (10.23 g).

mp: 168°–169° C.

IR (Nujol): 1730, 1605, 1525, 1360, 1315, 1140 $cm^{-1}$

NMR (DMSO-$d_6$, δ): 3.52 (3H, s), 3.96 (3H, s), 8.68 (1H, d, J=2.0 Hz), 8.85 (1H, d, J=2.0 Hz)

Preparation 3

The following compound was obtained according to a similar manner to that of Preparation 2.

Methyl 3-methylsulfonyl-5-nitro-4-piperidinobenzoate mp: 147°–150° C.

IR (Nujol): 1720, 1600, 1525, 1360, 1140 $cm^{-1}$

NMR (DMSO-$d_6$, δ): 1.48–1.72 (6H, m), 3.00–3.12 (4H, m), 3.45 (3H, s), 3.92 (3H, s), 8.54 (1H, d, J=2.2 Hz), 8.64 (1H, d, J=2.2 Hz)

Preparation 4

10% Palladium-carbon (2.5 g) was added to a mixture of methyl 4-chloro-3-methylsulfonyl-5-nitrobenzoate (9.5 g) and triethylamine (5.0 ml) in methanol (150 ml) and tetrahydrofuran (100 ml), and the mixture was subjected to catalytic reduction at ambient temperature under atmospheric pressure. The catalyst was removed by filtration and the filtrate was evaporated in vacuo. To the residue was added a mixture of ethyl acetate and water, and adjusted to pH 9 with 20% aqueous potassium carbonate solution. The separated organic layer was washed with brine, dried over magnesium sulfate and evaporated in vacuo. The residue was triturated with diisopropyl ether to give methyl 5-amino-3-methylsulfonylbenzoate (5.85 g).

mp: 181°–183° C.

IR (Nujol): 3480, 3440, 3370, 1725, 1605, 1330, 1150 $cm^{-1}$

NMR (DMSO-$d_6$, δ): 3.17 (3H, s), 3.86 (3H, s), 6.03 (2H, s), 7.28–7.32 (1H, m), 7.43–7.48 (1H, m), 7.48–7.54 (1H, m)

Preparation 5

The mixture of methyl 5-amino-3-methylsulfonylbenzoate (1.5 g) and 2,5-dimethoxytetrahydrofuran (1.3 ml) in acetic acid (4.5 ml) was heated under reflux for 2 hours under stirring. After cooling, the mixture was poured into a mixture of ethyl acetate and water, and adjusted to pH 8 with 20% aqueous potassium carbonate solution. The separated organic layer was washed with brine and dried over magnesium sulfate.

The solvent was removed by concentration and the residue was triturated with diisopropyl ether to give methyl 3-methylsulfonyl-5-(pyrrol-1-yl)benzoate (1.58 g).

mp: 117°–121° C.

IR (Nujol): 1720, 1605, 1310, 1150 $cm^{-1}$

NMR (DMSO-$d_6$, δ): 3.39 (3H, s), 3.95 (3H, s), 6.37 (2H, s), 7.62 (2H, s), 8.23 (1H, s), 8.35 (2H, s)

Preparation 6

The following compounds were obtained according to a similar manner to that of Preparation 5.

(1) Methyl 3-methylsulfonyl-4-piperidino-5-(pyrrol-1-yl)benzoate mp: 175°–176° C.

IR (Nujol): 1720, 1605, 1340, 1145 cm–1

NMR (DMSO-$d_6$, δ): 1.18–1.70 (6H, m), 2.30–3.10 (4H, m), 3.44 (3H, s), 3.89 (3H, s), 6.26–6.33 (2H, m), 6.95–7.02 (2H, m), 7.93 (1H, d, J=2.2 Hz), 8.55 (1H, d, J=2.2 Hz)

(2) Ethyl 3-(pyrrol-1-yl)benzoate mp: 46°–48° C.

IR (Nujol): 1710, 1590 $cm^{-1}$

NMR (DMSO-$d_6$, δ): 1.35 (3H, t, J=7.1 Hz), 4.36 (2H, q, J=7.1 Hz), 6.26–6.37 (2H, m), 7.37–7.50 (2H, M), 7.61 (1H, dd, J=7.8 Hz, 7.8 Hz), 7.83 (1H, d, J=7.8 Hz), 7.87 (1H, d, J=7.8 Hz), 8.03 (1H, s)

Elemental Analysis Calcd. for $C_{13}H_{13}NO_2$: C 72.54, H 6.09, N 6.51 Found: C 72.42, H 6.21, N 6.56

(3) Methyl 3-(pyrrol-1-yl)benzoate

IR (Film): 1720, 1590 $cm^{-1}$

NMR (DMSO-$d_6$, δ): 3.91 (3H, s), 6.30–6.38 (2H, m), 7.40–7.48 (2H, m), 7.59 (1H, dd, J=7.9 Hz, 7.9 Hz), 7.80–7.92 (2H, m), 8.05 (1H, dd, J=1.9 Hz, 1.9 Hz)

(4) Ethyl 2-(pyrrol-1-yl)benzoate

IR (Nujol): 1710, 1600 $cm^{-1}$

NMR (DMSO-$d_6$, δ): 1.06 (3H, t, J=7.1 Hz), 4.09 (2H, q, J=7.1 Hz), 6.19–6.27 (2H, m), 6.86–6.93 (2H, m), 7.42–7.53 (2H, m), 7.64 (1H, dd, J=1.7 Hz, 7.2 Hz), 7.69–7.77 (1H, m)

(5) Methyl 3,5-di(pyrrol-1-yl)benzoate mp: 111°–113° C.

IR (Nujol): 1720, 1600 $cm^{-1}$

NMR (DMSO-$d_6$, δ): 3.92 (3H, s), 6.28–6.40 (4H, m), 7.55–7.67 (4H, m), 7.89 (2H, d, J=2.1 Hz), 8.03 (1H, dd, J=2.1 Hz, 2.1 Hz)

Elemental Analysis Calcd. for $C_{16}H_{14}N_2O_2$: C 72.17, H 5.30, N 10.52 Found: C 72.31, H 5.28, N 10.44

(6) Methyl 3-nitro-5-(pyrrol-1-yl)benzoate mp: 147°–148° C.

IR (Nujol): 1720, 1540, 1360, 1340, 1260, 740, 730 $cm^{-1}$

NMR (DMSO-$d_6$, δ) 3.96 (3H, s), 6.3–6.4 (2H, m), 7.6–7.7 (2H, m), 8.4–8.5 (2H, m), 8.6–8.65 (1H, m)

MASS (m/z): 246 ($M^+$)

Elemental Analysis Calcd. for $C_{12}H_{10}N_2O_4$: C 58.53, H 4.09, N 11.3 Found: C 58.63, H 4.02, N 11.29

(7) Dimethyl 5-(pyrrol-1-yl)isophthalate mp: 108°–109° C.

IR (Nujol): 3125, 1720, 1605, 1235 $cm^{-1}$

NMR (DMSO-$d_6$, δ): 3.92 (6H, s), 6.32–6.35 (2H, m), 7.49–7.52 (2H, m), 8.23–8.27 (3H, m)

MASS (m/z): 260 ($M^+$+1)

Elemental Analysis Calcd. for $C_{14}H_{13}NO_4$: C 64.85, H 5.05, N 5.40 Found: C 64.96, H 5.15, N 5.44

(8) Methyl 2-methoxy-5-methylsulfonyl-3-(pyrrol-1-yl)benzoate mp: 97°–98° C.

IR (Nujol): 1720, 1150, 1080, 750 $cm^{-1}$

NMR (DMSO-$d_6$, δ): 3.34 (3H, s), 3.49 (3H, s), 3.91 (3H, s), 6.32–6.35 (2H, m), 7.15–7.22 (2H, m), 8.08 (1H, d, J=2.4 Hz)

Preparation 7

10% Palladium-carbon (1.5 g) was added to a mixture of methyl 3-methylsulfonyl-5-nitro-4-piperidinobenzoate (5.6 g) in a mixture of methanol (50 ml) and tetrahydrofuran (50 ml) and the mixture was subjected to catalytic reduction at ambient temperature under atmospheric pressure. The catalyst was removed by filtration and the filtrate was evaporated in vacuo. The residue was triturated with a mixture of diisopropyl ether and n-hexane to give methyl 5-amino-3-methylsulfonyl-4-piperidinobenzoate (4.88 g).

mp: 178°–179° C.

IR (Nujol): 3350, 3250, 1710, 1330, 1130 cm$^{-1}$

NMR (DMSO-d$_6$, δ): 1.35–1.80 (6H, m), 2.74–3.91 (2H, m), 3.28–3.46 (2H, m), 3.35 (3H, s), 3.84 (3H, s), 7.46 (1H, d, J=2.1 Hz), 7.62 (1H, d, J=2.1 Hz)

Preparation 8

The mixture of 4-chloro-3-methylsulfonyl-5-nitrobenzoic acid (5.0 g) and piperidine (25.0 ml) was stirred for 1 hour at ambient temperature. To the mixture was added a mixture of ethyl acetate and water and the mixture was adjusted to pH 1 with conc. hydrochloric acid. The separated organic layer was washed with water and dried over magnesium sulfate. The solvent was removed by concentration and the residue was triturated with a mixture of diisopropyl ether and n-hexane to give 3-methylsulfonyl-5-nitro-4-piperidinobenzoic acid (5.66 g).

mp: 197°–199° C.

IR (Nujol): 1700, 1530, 1305, 1125 cm$^{-1}$

NMR (DMSO-d$_6$, δ): 1.47–1.74 (6H, m), 3.01–3.13 (4H, m), 3.45 (3H, s), 8.48 (1H, d, J=2.1 Hz), 8.65 (1H, d, J=2.1 Hz), 13.91 (1H, br s)

Preparation 9

The mixture of ethyl 3-aminobenzoate (3.0 g), tri(ethoxy)methane (3.0 ml) and sodium azide (1.2 g) in acetic acid (30 ml) was stirred for 5 hours at 60°–70° C. To the reaction mixture was added water and the mixture was adjusted to pH 8 with potassium carbonate. The isolated precipitate was collected by filtration and the precipitate was dissolved in a mixture of ethyl acetate and tetrahydrofuran. The mixture was washed with water, dried over magnesium sulfate and evaporated in vacuo. The residue was recrystallized from a mixture of ethanol and diisopropyl ether to give ethyl 3-(1H-tetrazol-1-yl)benzoate (2.44 g).

mp: 104°–105° C.

IR (Nujol): 3120, 1700, 1590 cm$^{-1}$

NMR (DMSO-d$_6$, δ): 1.37 (3H, t, J=7.1 Hz), 4.40 (2H, q, J=7.1 Hz), 7.82 (1H, dd, J=7.9 Hz, 7.9 Hz), 8.10–8.18 (1H, m), 8.18–8.28 (1H, m), 8.44 (1H, dd, J=1.8 Hz, 1.8 Hz), 10.24 (1H, s)

MASS (m/z): 219 (M$^+$+1)

Elemental Analysis Calcd. for $C_{10}H_{10}N_4O_2$: C 55.04, H 4.62, N 25.68 Found: C 55.19, H 4.61, N 25.66

Preparation 10

The mixture of ethyl 3-aminobenzoate (2.0 g), hexane-2,5-dione (1.8 ml) and acetic acid (0.7 ml) in benzene (10.0 ml) was heated under reflux for 5 hours, while water was removed in a Dean-Stark apparatus. To the mixture was added a mixture of ethyl acetate and water and the mixture was adjusted to pH 8 with potassium carbonate. The separated organic layer was washed with a brine, dried over magnesium sulfate and evaporated in vacuo to give ethyl 3-(2,5-dimethylpyrrol-1-yl)benzoate (2.9 g) as an oil.

IR (Nujol): 1715, 1585 cm$^{-1}$

NMR (DMSO-d$_6$, δ): 1.33 (3H, t, J=7.1 Hz), 1.96 (6H, s), 4.34 (2H, q, J=7.1 Hz), 5.84 (2H, s), 7.55–7.77 (3H, m), 8.00–8.08 (1H, m)

Preparation 11

The mixture of 3-hydrazinobenzoic acid (2.0 g), 1,1,3,3-tetramethoxypropane (2.2 ml) and conc. hydrochloric acid (2.4 ml) in methanol (10.0 ml) was heated under reflux for 2 hours, and the mixture was evaporated in vacuo. The residue was dissolved in ethyl acetate, washed with a saturated aqueous sodium bicarbonate solution and brine. The residue was obtained by evaporating solvent, and purified by column chromatography on silica gel eluting with dichloromethane. The fractions containing the desired product were collected and evaporated in vacuo to give methyl 3-(pyrazol-1-yl)benzoate (1.33 g).

mp: 48°–50° C.

IR (Nujol): 3130, 1705, 1610, 1590 cm$^{-1}$

NMR (DMSO-d$_6$, δ): 3.92 (3H, s), 6.57–6.63 (1H, m), 7.66 (1H, dd, J=7.9 Hz, 7.9 Hz), 7.82 (1H, d, J=1.6 Hz), 7.86–7.94 (1H, m), 8.10–8.20 (1H, m), 8.40–8.47 (1H, m), 8.64 (1H, d, J=2.5 Hz)

MASS: 203 (M$^+$+1)

Elemental Analysis Calcd. for $C_{11}H_{10}N_2O_2$: C 65.34, H 4.98, N 13.85 Found: C 65.11, H 4.94, N 13.78

Preparation 12

The mixture of methyl 5-acetyl-3-pyridinecarboxylate (3.0 g) and N,N-dimethylformamide dimethyl acetal (6.7 ml) in tetrahydrofuran (30 ml) was heated under reflux for 6 hours. To the mixture was added a mixture of ethyl acetate and tetrahydrofuran, and the mixture was washed with brine and dried over magnesium sulfate. The solvent was removed by concentration and the residue was triturated with diisopropyl ether to give methyl 5-(3-dimethylamino-1-oxo-2-propenyl)-3-pyridinecarboxylate (1.88 g).

mp: 135°–137° C.

IR (Nujol): 1720, 1640, 1600 cm$^{-1}$

NMR (DMSO-d$_6$, δ): 2.98 (3H, s), 3.19 (3H, s), 3.92 (3H, s), 5.94 (1H, d, J=12.1 Hz), 7.84 (1H, d, J=12.1 Hz), 8.63 (1H, dd, J=2.1 Hz, 2.1 Hz), 9.15 (1H, d, J=2.1 Hz), 9.32 (1H, d, J=2.1 Hz)

Preparation 13

The mixture of methyl 5-(3-dimethylamino-1-oxo-2-propenyl)-3-pyridinecarboxylate (1.7 g), acetic acid (0.62 ml) and hydrazine monohydrate (0.53 ml) in methanol (34 ml) was stirred for 24 hours at ambient temperature, and the mixture was evaporated in vacuo. To the residue was added a mixture of tetrahydrofuran, ethyl acetate and water, and the mixture was adjusted to pH 9 with potassium carbonate. The separated organic layer was washed with brine and dried over magnesium sulfate. The solvent was removed by concentration and the residue was triturated with diisopropyl ether to give methyl 5-(pyrazol-3-yl)-3-pyridinecarboxylate (1.24 g).

mp: 138°–141° C.

IR (Nujol): 3100, 1720, 1600 cm$^{-1}$

NMR (DMSO-d$_6$, δ): 3.93 (3H, s), 6.98 (1H, s), 7.89 (1H, s), 8.64 (1H, s), 9.01 (1H, s), 9.27 (1H, s), 13.20 (1H, s)

Preparation 14

Thionyl chloride (2.5 ml) was added dropwise in methanol (25 ml) under cooling at 7°–9° C. After the mixture was stirred for 30 minutes at the same temperature, 5-(3-methyl-1,2,4-oxadiazol-5-yl)-3-pyridinecarboxylic acid (2.5 g) was added thereto and the mixture was refluxed for 3 hours. After being cooled to room temperature, the mixture was poured into a mixture of ethyl acetate (100 ml) and water (100 ml). The organic layer was successively washed with 10% potassium carbonate aqueous solution and brine, and then dried over magnesium sulfate. The solvent was evaporated in vacuo and the residue was recrystallized from diethyl ether to afford methyl 5-(3-methyl-1,2,4-oxadiazol-5-yl)-3-pyridinecarboxylate (2.12 g).

mp: 131°–132° C.

IR (Nujol): 1720, 1610, 1100, 740 cm$^{-1}$

NMR (DMSO-d$_6$, δ): 2.47 (3H, s), 3.96 (3H, s), 8.77 (1H, dd, J=2.1 Hz, 2.1 Hz), 9.31 (1H, d, J=2.1 Hz), 9.45 (1H, d, J=2.1 Hz)

MASS (m/z): 218 (M$^+$–1)

Preparation 15

To a suspension of 1-(hydroxyimino)ethylamine (7.4 g) in dry tetrahydrofuran (450 ml) was added sodium hydride (3.7 g, 60% in mineral oil) carefully. The mixture was stirred at room temperature for 15 minutes, and refluxed for 30 minutes. To this mixture was added 3,5-bis (methoxycarbonyl)pyridine (15 g), and the mixture was refluxed for 3 hours. After being cooled to room temperature, the reaction mixture was poured into a mixture of ethyl acetate (200 ml) and water (200 ml) under stirring. The aqueous layer was adjusted to pH 3.5 with 10% hydrochloric acid. The resulting precipitate was collected by filtration, washed with water and dried in vacuo to afford 5-(3-methyl-1,2,4-oxadiazol-5-yl)-3-pyridinecarboxylic acid (5.04 g).

mp: 242°–244° C. (dec.)

IR (Nujol): 1710, 1455, 1170 cm$^{-1}$

NMR (DMSO-d$_6$, δ): 2.47 (3H, s), 8.63 (1H, t, J=2.1 Hz), 9.28 (1H, t, J=2.1 Hz), 9.41 (1H, d, J=2.1 Hz)

MASS (m/z): 203 (M$^+$–2)

Preparation 16

A mixture of methyl 5-tert-butoxycarbonylamino-3-pyridinecarboxylate (5.7 g) and conc. hydrochloric acid (11.4 ml) in methanol (57 ml) was stirred for 1 hour at 40° C. After being cooled to room temperature, the reaction mixture was poured into a mixture of ethyl acetate (100 ml) and water (50 ml) under stirring, and adjusted to pH 9.0 with 10% potassium carbonate aqueous solution. The organic layer was washed with brine and dried over magnesium sulfate. The solvent was evaporated in vacuo and the residue was recrystallized from diethyl ether-methanol to afford methyl 5-amino-3-pyridinecarboxylate (2.03 g).

mp: 128°–130° C.

IR (Nujol): 3300, 3125, 1720, 1245, 1120 cm$^{-1}$

NMR (DMSO-d$_6$, δ): 3.84 (3H, s), 7.40–7.50 (1H, m), 8.12–8.15 (1H, m), 8.20–8.30 (1H, m)

MASS: 151 (M$^+$–1)

Preparation 17

A mixture of methyl 5-amino-3-pyridinecarboxylate (1.7 g) and 2.5-dimethoxytetrahydrofuran (2.2 g) in acetic acid (5 ml) was refluxed for 30 minutes. After being cooled to room temperature, the reaction mixture was poured into a mixture of ethyl acetate (50 ml) and water (50 ml) under stirring, and adjusted to pH 8.5 with 10% potassium carbonate aqueous solution. The organic layer was washed with brine and dried over magnesium sulfate. The solvent was evaporated in vacuo and the residue was recrystallized from diethyl ether-n-hexane to afford methyl 5-(pyrrol-1-yl)-3-pyridinecarboxylate (1.29 g).

mp: 101°–102° C.

IR: 1710, 1590, 1260 cm$^{-1}$

NMR (DMSO-d$_6$, δ) 3.93 (3H, s), 6.30–6.40 (2H, m), 7.55–7.65 (2H, m), 8.35–8.40 (1H, m), 8.93 (1H, d, J=1.7 Hz), 9.17 (1H, d, J=2.7 Hz)

MASS: 203 (M$^+$)

Elemental Analysis Calcd. for C$_{11}$H$_{10}$N$_2$O$_2$: C 65.34, H 4.98, N 13.85 Found: C 65.11, H 5.03, N 13.63

Preparation 18

A solution of 1-methylthio-2-bromobenzene (5 g) in dry ether (30 ml) was stirred at 0° C. and 1.63M n-butyllithium in hexane solution (16.6 ml) was added dropwise over a period of 15 minutes. The reaction mixture was stirred at 0° C. for 1.5 hours and then transferred to a cold (–78° C.) solution of triisopropyl borate (7.4 ml) in tetrahydrofuran (40 ml) over 40 minutes. After stirring for 1 hour at –78° C., the reaction mixture was allowed to warm to room temperature overnight. The suspension was poured into dilute 2M hydrochloric acid (40 ml) and the layers were separated. The aqueous phase was extracted with ether (2×80 ml) and the combined organic phases were washed with brine, dried with magnesium sulfate, evaporated and washed with petroleum ether (2×20 ml) to afford 2-methylthiophenyldihydroxyborane.

mp: 83°–84° C.

IR (Nujol): 3250, 1580, 1010, 740 cm$^{-1}$

NMR (DMSO-d$_6$, δ): 2.41 (3H, s), 7.07–7.36 (4H, m), 8.09 (2H, s)

MASS (m/z): 168 (M$^+$)

Preparation 19

The following compounds were obtained according to a similar manner to that of Preparation 18.

(1) 2-Methoxyphenyl-dihydroxyborane mp: 105°–106° C.

IR (Nujol) 3350, 1600, 1220, 1160, 1050, 1020, 750 cm$^{-1}$

NMR (DMSO-d$_6$, δ): 3.80 (3H, s), 6.90–6.99 (2H, m), 7.39 (1H, ddd, J=7.2 Hz, 7.2 Hz, 1.8 Hz), 7.57 (1H, dd, J=7.2 Hz, 1.8 Hz), 7.70 (2H, s)

MASS (m/z): 152

(2) 2-Trifluoromethylphenyl-dihydroxyborane mp: 144°–145° C.

IR (Nujol): 3250, 1100, 770, 720 cm$^{-1}$

NMR (DMSO-d$_6$, δ): 7.50–7.67 (4H, m), 8.33 (2H, s)

Preparation 20

The mixture of 2-methylthiophenyl-dihydroxyborane (1.55 g) and 3-iodobenzoic acid (2.08 g) in water (30 ml) was stirred at room temperature, then sodium carbonate (2.67 g) and palladium(II) acetate (0.019 g) were added thereto. After stirring at 40° C. overnight, the reaction mixture was filtered and was washed with ether (2×20 ml). The aqueous layer was adjusted to pH 2 with 6N-hydrochloric acid. The crystalline was collected, washed with water, and dried to afford 3-(2-methylthiophenyl) benzoic acid.

IR (Nujol): 1680, 1275, 945, 750 cm$^{-1}$

Preparation 21

The following compounds were obtained according to a similar manner to that of Preparation 20.

(1) 3-(2-Methylphenyl)benzoic acid mp: 135°–137° C.

IR (Nujol): 1670, 750 cm$^{-1}$

NMR (DMSO-d$_6$, δ): 2.23 (3H, s), 7.20–7.35 (4H, m), 7.57–7.64 (2H, m), 7.86 (1H, s), 7.93–7.98 (1H, m), 13.05 (1H, br s)

MASS (m/z): 211 (M$^+$–1)

(2) 3-(4-Methoxyphenyl)benzoic acid mp: 212°–213° C.

IR (Nujol): 1675, 1250, 1020 cm$^{-1}$

NMR (DMSO-d$_6$, δ): 3.81 (3H, s), 7.05 (2H, dd, J=6.7 Hz, 2.1 Hz), 7.56 (1H, dd, J=7.7 Hz, 7.7 Hz), 7.65 (2H, dd, J=6.7 Hz, 2.1 Hz), 7.85–7.91 (2H, m), 8.14 (1H, dd, J=1.7 Hz, 1.7 Hz), 13.07 (1H, br s)

MASS (m/z): 227 (M$^+$–1)

(3) 3-(3-Methoxyphenyl)benzoic acid mp: 129°–131° C.

IR (Nujol): 1690, 1310, 1210, 1040, 750 cm$^{-1}$

NMR (DMSO-d$_6$, δ): 3.84 (3H, s), 6.96–7.01 (1H, m), 7.21–7.28 (2H, m), 7.42 (1H, dd, J=7.9 Hz, 7.9 Hz), 7.59 (1H, dd, J=7.7 Hz, 7.7 Hz), 7.90–7.97 (2H, m), 8.18 (1H, dd, J=1.5 Hz, 1.5 Hz)

MASS (m/z): 227 (M⁺–1)
(4) 3-(1-Naphthyl)benzoic acid
mp: 185°–187° C.
IR (Nujol): 1670, 1300, 770 cm⁻¹
NMR (DMSO-d$_6$, δ): 7.47–7.79 (7H, m), 7.98–8.09 (4H, m)
MASS (m/z): 247 (M⁺–1)
(5) 3-(2-Naphthyl)benzoic acid
mp 213°–215° C.
IR (Nujol): 1670, 1310, 1250, 810, 750 cm⁻¹
NMR (DMSO-d$_6$, δ): 7.52–7.71 (3H, m), 7.86–8.11 (6H, m), 8.30 (1H, s), 8.37–8.39 (1H, m), 13.17 (1H, br s)
MASS (m/z): 247 (M⁺–1)
(6) 3-(2-Methoxyphenyl)benzoic acid
mp: 176°–178° C.
IR (Nujol): 1690, 1310, 1250, 1020, 720 cm⁻¹
NMR (DMSO-d$_6$, δ): 3.78 (3H, s), 7.03–7.16 (2H, m), 7.30–7.42 (2H, m), 7.54 (1H, dd, J=7.7 Hz, 7.7 Hz), 7.72 (1H, ddd, J=7.9 Hz, 1.6 Hz, 1.6 Hz), 7.91 (1H, ddd, J=7.7 Hz, 1.5 Hz, 1.5 Hz), 8.05 (1H, dd, J=1.6 Hz, 1.6 Hz), 13.02 (1H, br s)
MASS (m/z): 227 (M⁺–1)
(7) 3-(2-Trifluoromethylphenyl)benzoic acid
IR (Nujol): 1680, 1310, 1110, 750 cm⁻¹

Preparation 22

The following compounds were obtained according to a similar manner to that of Preparation 2.
(1) Methyl 3-(4-methoxyphenyl)benzoate
mp: 62°–64° C.
IR (Nujol): 1720, 1610, 1020, 835 cm⁻¹
NMR (DMSO-d$_6$, δ): 3.81 (3H, s), 3.89 (3H, s), 7.05 (2H, dd, J=7.9 Hz, 1.7 Hz), 7.59 (1H, dd, J=7.9 Hz, 7.9 Hz), 7.85–7.95 (2H, m), 8.15 (1H, dd, J=1.7 Hz)
MASS (m/z): 243 (Mu+1)
(2) Methyl 3-(3-methoxyphenyl)benzoate
IR (Nujol): 1720, 1250, 1210, 1110, 750 cm⁻¹
NMR (DMSO-d$_6$, δ) 3.84 (3H, s), 3.90 (3H, s), 6.97–7.02 (1H, m), 7.21–7.28 (2H, m), 7.42 (1H, dd, J=7.7 Hz, 7.7 Hz), 7.62 (1H, dd, J=7.7 Hz, 7.7 Hz), 7.94–7.99 (2H, m), 8.18 (1H, dd, J=1.7 Hz, 1.7 Hz)
MASS (m/z): 243 (M⁺+1)
(3) Methyl 3-(1-naphthyl)benzoate
mp: 73°–74° C.
IR (Nujol): 1720, 1300, 1260, 1240, 1100, 800, 770, 750 cm⁻¹
NMR (DMSO-d$_6$, δ) 3.89 (3H, s), 7.47–7.78 (7H, m), 7.99–8.10 (4H, m)
MASS (m/z): 263 (M⁺+1)
(4) Methyl 3-(2-naphthyl)benzoate
mp: 51°–52° C.
IR (Nujol): 1720, 1290, 1250, 1110, 810, 750 cm⁻¹
NMR (DMSO-d$_6$, δ) 3.93 (3H, s), 7.52–7.72 (3H, m), 7.85–8.13 (6H, m), 8.29 (1H, s), 8.36 (1H, s)
MASS (m/z): 263 (M⁺+1)
(5) Methyl 3-(2-methoxyphenyl)benzoate
mp: 91°–93° C.
IR (Nujol): 1710, 1310, 1250, 1100, 1020, 760 cm⁻¹
NMR (DMSO-d$_6$, δ): 3.78 (3H, s), 3.88 (3H, s), 7.05–7.16 (2H, m), 7.30–7.40 (2H, m), 7.57 (1H, dd, J=7.7 Hz, 7.7 Hz), 7.76 (1H, dd, J=8.0 Hz, 1.6 Hz, 1.6 Hz), 7.93 (1H, ddd, J=7.8 Hz, 1.5 Hz, 1.5 Hz), 8.07 (1H, dd, J=1.6 Hz, 1.6 Hz)
MASS (m/z): 243 (M⁺+1)
(6) Methyl 3-(2-trifluoromethylphenyl)benzoate
mp: 41°–43° C.
IR (Nujol): 1730, 1310, 1240, 1170, 1130, 1040, 740 cm⁻¹
NMR (DMSO-d$_6$, δ) 3.87 (3H, s), 7.46 (1H, d, J=7.3 Hz), 7.62–7.80 (4H, m), 7.85–7.88 (2H, m), 7.99–8.06 (1H, m)

MASS (m/z): 281 (M⁺+1)
(7) Methyl 3-(2-methylphenyl)benzoate
IR (Neat): 1720, 1580, 1300, 1240, 1110, 970, 740 cm⁻¹
NMR (DMSO-d$_6$, δ): 2.22 (3H, s), 3.88 (3H, s), 7.21–7.35 (4H, m), 7.60–7.67 (2H, m), 7.88 (1H, dd, J=1.5 Hz, 1.5 Hz), 7.97 (1H, ddd, J=6.9 Hz, 1.9 Hz, 1.9 Hz)
MASS (m/z): 227 (M⁺+1)
(8) Methyl 3-(2-methylthiophenyl)benzoate
mp: 91°–92° C.
IR (Nujol): 1710, 1300, 1230, 750 cm⁻¹
NMR (DMSO-d$_6$, δ): 2.38 (3H, s), 3.87 (3H, s), 7.22–7.30 (2H, m), 7.35–7.46 (2H, m), 7.56–7.68 (2H, m), 7.94–8.01 (2H, m)
MASS (m/z): 259 (M⁺+1)

Preparation 23

The following compounds were obtained according to a similar manner to that of Preparation 5.
(1) Methyl 4-n-butyl-3-(pyrrol-1-yl)benzoate
IR (Film): 1720, 1610 cm⁻¹
NMR (DMSO-d$_6$, δ): 0.77 (3H, t, J=7.1 Hz), 1.05–1.45 (4H, m), 2.48–2.60 (2H, m), 3.85 (3H, s), 6.22–6.28 (2H, m), 6.91–6.96 (2H, m), 7.55 (1H, d, J=8.0 Hz), 7.72 (1H, d, J=1.7 Hz), 7.93 (1H, dd, J=1.7 Hz, 8.0 Hz)
(2) Methyl 4-methyl-3-(pyrrol-1-yl)benzoate
mp: 46° C.
IR (Nujol): 1715 cm⁻¹
NMR (DMSO-d$_6$, δ): 2.25 (3H, s), 3.86 (3H, s), 6.23–6.29 (2H, m), 6.95–7.01 (2H, m), 7.53 (1H, d, J=7.9 Hz), 1.74 (1H, d, J=1.8 Hz), 7.88 (1H, dd, J=1.8 Hz, 7.9 Hz)
(3) Methyl 5-cyano-3-(pyrrol-1-yl)benzoate
mp: 124°–126° C.
IR (Nujol): 2240, 1700, 1595 cm⁻¹
NMR (DMSO-d$_6$, δ): 3.93 (3H, s), 6.31–6.36 (2H, m), 7.57–7.60 (2H, m), 8.13 (1H, dd, J=1.4 Hz, 1.4 Hz), 8.32 (1H, dd, J=1.4 Hz, 2.3 Hz), 8.45 (1H, dd, J=1.4 Hz, 2.3 Hz)
(4) Methyl 3-chloro-5-(pyrrol-1-yl)benzoate
mp: 70°–72° C.
IR (Nujol): 1720, 1580, 1340, 1260, 760, 720 cm⁻¹
NMR (DMSO-d$_6$, δ): 3.90 (3H, s), 6.30–6.35 (2H, m), 7.50–7.55 (2H, m), 7.75–7.80 (1H, m), 8.00–8.03 (1H, m), 8.03–8.06 (1H, m)
MASS (m/z): 236 (M+1)
(5) Methyl 3-(3-formylpyrrol-1-yl)benzoate
IR (Film): 1720, 1665, 1590 cm⁻¹
NMR (DMSO-d$_6$, δ): 3.91 (3H, s), 6.72 (1H, dd, J=1.6 Hz, 3.1 Hz), 7.61–7.65 (1H, m), 7.67–7.74 (1H, m), 7.91–8.04 (2H, m), 8.12–8.18 (1H, m), 8.35–8.40 (1H, m), 9.81 (1H, s)
(6) Methyl 4-hydroxy-3-(pyrrol-1-yl)benzoate
mp: 98°–100° C.
IR (Nujol): 3220, 1677, 1605 cm⁻¹
NMR (DMSO-d$_6$, δ): 3.82 (3H, s), 6.17–6.23 (2H, m), 7.07–7.19 (3H, m), 7.74–7.85 (2H, m), 11.00 (1H, s)

Preparation 24

A mixture of dimethyl 5-(pyrrol-1-yl)isophthalate (3.0 g), methyl acetate (0.86 g) and sodium methoxide (0.81 g) in N,N-dimethylformamide (21 ml) was heated at 55° C. for 3 hours. After being cooled to room temperature, the reaction mixture was poured into water (100 ml) and the whole was adjusted to pH 3 with 10% hydrochloric acid. The resulting precipitate was collected and washed with water. This crude product was purified by column chromatography on silica gel (150 ml) with benzene-ethyl acetate (30:1) as an eluent. The fractions containing the object product were collected and evaporated in vacuo. The residue was recrystallized from methanol to afford methyl 3-[3-methoxycarbonyl-5-(pyrrol-1-yl)phenyl]-3-oxopropionate (0.31 g).

mp: 82°–84° C.

IR (Nujol): 1720, 1690, 1260, 720 cm$^{-1}$

NMR (DMSO-d$_6$, δ): 3.68 (3H, s), 3.93 (3H, s), 4.42 (2H, s), 6.3–6.4 (2H, m), 7.55–7.65 (2H, m), 8.29 (2H, s), 8.34 (1H, s)

MASS (m/z): 300 (M–1)

Preparation 25

A solution of methyl 3-[3-methoxycarbonyl-5-(pyrrol-1-yl)phenyl]-3-oxopropionate (0.1 g) in a mixture of water (1 ml), methanol (3 ml) and concentrated sulfuric acid (40 mg) was refluxed for 16 hours. After being cooled to room temperature, the reaction mixture was poured into a mixture of ethyl acetate (50 ml) and water (50 ml). The organic layer was successively washed with a saturated aqueous sodium hydrogencarbonate solution and brine, dried over magnesium sulfate and evaporated in vacuo to afford methyl 3-acetyl-5-(pyrrol-1-yl)benzoate (20.1 mg).

mp: 101°–103° C.

IR (Nujol): 1720, 1690, 1230, 730 cm$^{-1}$

NMR (DMSO-d$_6$, δ): 2.71 (3H, s), 3.93 (3H, s), 6.30–6.36 (2H, m), 7.56–7.59 (2H, m), 8.25–8.33 (3H, m)

MASS (m/z): 243 (M$^+$)

Preparation 26

A suspension of 1-tri(n-butyl)stannyl-2-(4,4-dimethyl-4,5-dihydrooxazol-2-yl)benzene (5 g), methyl 3-iodobenzoate (2.17 g) and tetrakis(triphenylphosphine) palladium(0) (0.29 g) in dioxane was refluxed for 18 hours. After being cooled to room temperature, 25% potassium fluoride aqueous solution (11 ml) was added to the reaction mixture and the mixture was stirred for 15 minutes. Insoluble material was filtered by using celite The filtrate was extracted with ethyl acetate (50 ml), washed with brine, dried over magnesium sulfate, filtered and evaporated in vacuo. The residue was purified by column chromatography on silica gel (200 g) with benzene-ethyl acetate (20:1) as an eluent. The fractions containing the object compound were combined and evaporated in vacuo. The residue was recrystallized from methanol to afford methyl 3-[2-(4,4-dimethyl-4,5-dihydrooxazol-2-yl)phenyl]benzoate (370 mg).

mp: 103°–104° C.

IR (Nujol): 1710, 1655, 1300, 745 cm$^{-1}$

NMR (DMSO-d$_6$, δ): 1.17 (6H, s), 3.79 (2H, s), 3.86 (3H, s), 7.3–7.7 (7H, m), 7.9–8.0 (2H, m)

MASS (m/z): 310 (M+1)

Preparation 27

The following compounds were obtained according to a similar manner to that of Preparation 26.

(1) Methyl 3-(thiophen-3-yl)benzoate mp: 50°–51° C.

IR (Nujol): 1710, 1285, 1235, 780, 745 cm$^{-1}$

NMR (DMSO-d$_6$, δ): 3.89 (3H, s), 7.54–7.71 (3H, m), 7.85–7.90 (1H, m), 7.98–8.05 (2H, m), 8.23–8.25 (1H, m)

MASS (m/z): 219 (M+1)

(2) Methyl 3-(thiophen-2-yl)benzoate

IR (Film): 1615, 1440, 1290, 750 cm$^{-1}$

NMR (DMSO-d$_6$, δ): 3.90 (3H, s), 7.15–7.20 (1H, m), 7.50–7.65 (3H, m), 7.85–8.00 (2H, m), 8.16–8.17 (1H, m)

MASS (m/z): 219 (M+1)

(3) Methyl 3-(thiazol-2-yl)benzoate mp: 50°–52° C.

IR (Nujol): 1700, 1295, 1220, 755 cm$^{-1}$

NMR (DMSO-d$_6$, δ): 3.91 (3H, s), 7.68 (1H, dd, J=7.8 Hz, 7.8 Hz), 7.88 (1H, d, J=3.2 Hz), 7.99 (1H, d, J=3.2 Hz), 8.03–8.09 (1H, m), 8.19–8.25 (1H, m), 8.49–8.51 (1H, m)

MASS (m/z): 220 (M+1)

(4) Methyl 3-[4-(4,4-dimethyl-4,5-dihydrooxazol-2-yl)phenyl]benzoate

IR (Neat): 2950, 1720, 1640, 1440, 1300, 1240 cm$^{-1}$

NMR (DMSO-d$_6$, δ): 1.31 (6H, s), 3.90 (3H, s), 4.14 (2H, s), 7.66 (1H, dd, J=7.7 Hz, 7.7 Hz), 7.82 (2H, d, J=8.5 Hz), 7.94–8.05 (4H, m), 8.24 (1H, s)

MASS (m/z): 310 (M$^+$+1)

Preparation 28

To a solution of methyl 3-[2-(4,4-dimethyl- 4,5-dihydrooxazol-2-yl)phenyl]benzoate (1.25 g) in pyridine (5 ml) at 7° C. was added dropwise phosphoryl chloride (0.75 ml) keeping the reaction temperature below 20° C. The reaction mixture was stirred at 100° C. for 4 hours. After being cooled to room temperature, the mixture was quenched by water, and the emulsion was extracted with ethyl acetate (50 ml). The organic layer was successively washed with 6N-hydrochloric acid and brine, dried over magnesium sulfate, filtered, and evaporated in vacuo. The residue was purified by column chromatography on silica gel (25 g) with dichloromethane as an eluent. The fractions containing the object compound were combined and evaporated in vacuo. The crystalline residue was recrystallized from methanol to afford methyl 3-(2-cyanophenyl)benzoate (0.7 g).

mp: 83°–85° C.

IR (Nujol): 2225, 1720, 1245, 730 cm$^{-1}$

NMR (DMSO-d$_6$, δ): 3.90 (3H, s), 7.5–8.2 (8H, m)

MASS (m/z): 238 (M+1)

Preparation 29

The following compound was obtained according to a similar manner to that of Preparation 28.

Methyl 3-(4-cyanophenyl)benzoate mp: 123°–125° C.

IR (Nujol): 2230, 1720 cm$^{-1}$

NMR (DMSO-d$_6$, δ): 3.90 (3H, s), 7.68 (1H, dd, J=7.8 Hz, 7.8 Hz), 7.90–8.06 (6H, m), 8.25 (1H, s)

MASS (m/z): 238 (M$^+$+1)

Preparation 30

To a mixture of 3-methoxycarbonyl-5-(pyrrol-1-yl)-benzoic acid (3.0 g), 4-hydroxypiperidine (1.23 g) and 1-hydroxybenzotriazole (1.81 g) in dichloromethane (100 ml) was added 1-ethyl-3-(3-dimethylaminopropyl)carbodiimide (2.57 g) under ice cooling, and the solution was stirred for 30 hours at room temperature. After evaporating the solvent, the residue was dissolved in a mixture of ethyl acetate and a saturated aqueous sodium hydrogencarbonate solution under stirring. The organic layer was successively washed with water and brine, and dried over magnesium sulfate. The solvent was evaporated in vacuo and the residue was purified by column chromatography on silica gel eluting with a mixture of chloroform and methanol (50:1). The fractions containing the desired product were collected and evaporated in vacuo to afford methyl 3-[(4-hydroxypiperidin-1-yl)carbonyl]-5-(pyrrol-1-yl)benzoate (3.56 g).

mp: 158°–159° C.

IR (Nujol): 3350, 1730, 1600 cm$^{-1}$

NMR (DMSO-d$_6$, δ): 1.2–2.0 (4H, m), 3.0–4.2 (6H, m), 3.91 (3H, s), 6.3–6.4 (2H, m), 7.5–7.6 (2H, m), 7.7–7.8 (1H, m), 7.9–8.0 (1H, m), 8.1–8.2 (1H, m)

MASS (m/z): 329 (M$^+$+1)

Preparation 31

The following compounds were obtained according to a similar manner to that of Preparation 30.

(1) Methyl 3-[(2-dimethylaminoethyl)carbamoyl]-5-(pyrrol-1-yl)benzoate mp: 108°–109° C.

IR (Nujol): 3370, 1720, 1640, 1600 cm$^{-1}$

NMR (DMSO-d$_6$, δ): 2.28 (6H, s), 2.5–2.6 (2H, m), 3.5–3.6 (2H, m), 3.98 (3H, s), 6.3–6.4 (2H, m), 6.97 (1H, br s), 7.1–7.2 (2H, m), 8.1–8.3 (3H, m)

MASS (m/z): 316 (M$^+$+1)

(2) Methyl 3-[(4-methylpiperazin-1-yl)carbonyl]-5-(pyrrol-1-yl)benzoate

IR (Film): 2950, 2800, 1720, 1630, 1600 cm$^{-1}$

NMR (DMSO-d$_6$, δ): 2.20 (3H, s), 2.1–2.5 (6H, m), 3.5–3.8 (2H, m), 3.91 (3H, s), 6.3–6.4 (2H, m), 7.5–7.6 (2H, m), 7.7–7.8 (1H, m), 7.9–8.0 (1H, m), 8.1–8.2 (1H, m)

MASS (m/z): 328 (M$^+$+1)

Preparation 32

Methyl 3-(3-formylpyrrol-1-yl)benzoate (10.2 g) was added to a mixture of hydroxylamine hydrochloride (3.1 g) and 28% methanolic sodium methoxide (8.6 ml) in methanol (100 ml) and the whole was stirred for 3 hours at ambient temperature. The solvent was removed by concentration. To the residue was added a mixture of ethyl acetate, tetrahydrofuran and water, and the mixture was adjusted to pH 2 with 6N-hydrochloric acid. The separated organic layer was washed with brine, dried over magnesium sulfate and evaporated in vacuo to give methyl 3-[3-(hydroxyiminomethyl)pyrrol-1-yl]benzoate (9.24 g) (oil).

IR (Film): 3170 (br), 1720 (br) cm$^{-1}$

NMR (DMSO-d$_6$, δ): 3.90 (3H, s), 6.50–6.54 and 6.68–6.72 (total 1H, each m), 7.31–7.77 (3H, m), 7.81–7.95 (2H, m), 7.98–8.06 (2H, m), 10.64 and 11.17 (total 1H, each s)

Preparation 33

The following compound was obtained according to a similar manner to that of Preparation 32.

Methyl 3-(2-hydroxyiminomethylpyrrol-1-yl)benzoate

IR (Film): 3150, 1720 cm$^{-1}$

NMR (DMSO-d$_6$, δ): 3.89 (3H, s), 6.29–6.34 and 6.34–6.40 (total 1H, each m), 6.61–6.66 and 7.28–7.32 (total 1H, each m), 7.03 and 7.85 (total 1H, each s), 7.12–7.17 and 7.16–7.20 (total 1H, each m), 7.64–7.75 (2H, m), 7.82–7.88 (1H, m), 7.96–8.12 (1H, m), 10.88 and 11.49 (total 1H, each s)

Preparation 34

Methyl 3-(2-formylpyrrol-1-yl)benzoate (5.0 g) was added to a mixture of hydroxylamine hydrochloride (1.5 g) and 28% methanolic sodium methoxide (4.2 ml) in methanol (50 ml) and the mixture was stirred for 4 hours at ambient temperature. The solvent was removed by concentration and the residue was dissolved in a mixture of ethyl acetate and water. The mixture was adjusted to pH 2 with 6N-hydrochloric acid. The separated organic layer was washed with brine, dried over magnesium sulfate and evaporated in vacuo. The residue was subjected to column chromatography on silica gel eluting with a mixture of chloroform and ethyl acetate (19:1). The first eluted fractions containing the desired product were collected and evaporated in vacuo and the residue was triturated with a mixture of diisopropyl ether and n-hexane to give methyl 3-[(E)-2-hydroxyiminomethylpyrrol-1-yl]benzoate (Compound A) (0.8 g). The further eluted fractions containing the desired product were collected and evaporated in vacuo to give methyl 3-[(Z)-2-hydroxyiminomethylpyrrol-1-yl]benzoate (Compound B) (1.43 g) as an oil.

Compound A mp: 87°–88° C.

IR (Nujol): 1720, 1590 cm$^{-1}$

NMR (DMSO-d$_6$, δ): 3.89 (3H, s), 6.29–6.34 (1H, m), 6.61–6.66 (1H, m), 7.12–7.17 (1H, m), 7.64–7.72 (2H, m), 7.82–7.88 (1H, m), 7.85 (1H, s), 7.96–8.08 (1H, m), 10.85 (1H, s)

MASS (m/z): 245 (M$^+$+1)

Compound B

IR (Film): 1705–1725, 1630, 1590 cm$^{-1}$

NMR (DMSO-d$_6$, δ): 3.89 (3H, s), 6.34–6.40 (1H, m), 7.03 (1H, s), 7.16–7.20 (1H, m), 7.28–7.32 (1H, m), 7.69–7.75 (2H, m), 7.82–7.85 (1H, m), 8.00–8.12 (1H, m), 11.45 (1H, s)

MASS (m/z): 245 (M$^+$+1)

Preparation 35

The mixture of methyl 3-(3-hydroxyiminomethylpyrrol-1-yl)benzoate (9.0 g) in acetic anhydride (45 ml) was heated under reflux for 3 hours under stirring and then the reaction mixture was concentrated in vacuo. To the residue was added a mixture of ethyl acetate and water, and the whole was adjusted to pH 8 with potassium carbonate. The separated organic layer was washed with water, dried over magnesium sulfate, and evaporated in vacuo. The residue was purified by column chromatography on silica gel eluting with chloroform. The eluted fractions containing the desired product were combined and evaporated in vacuo. The residue was triturated with a mixture of diisopropyl ether and n-hexane to give methyl 3-(3-cyanopyrrol-1-yl)benzoate (6.20 g).

mp: 105°–106° C.

IR (Nujol): 2230, 1725, 1590 cm$^{-1}$

NMR (DMSO-d$_6$, δ): 3.90 (3H, s), 6.73–6.79 (1H, m), 7.62–7.74 (2H, m), 7.91–7.99 (2H, m), 8.10–8.15 (1H, m), 8.32–8.37 (1H, m)

MASS (m/z): 227 (M$^+$+1)

Preparation 36

The following compound was obtained according to a similar manner to that of

Preparation 35.

Methyl 3-(2-cyanopyrrol-1-yl)benzoate mp: 89°–90° C.

IR (Nujol): 2220, 1715, 1590 cm$^{-1}$

NMR (DMSO-d$_6$, δ): 3.91 (3H, s), 6.49 (1H, dd, J=2.8 Hz, 3.9 Hz), 7.28 (1H, dd, J=1.6 Hz, 3.9 Hz), 7.65 (1H, dd, J=1.6 Hz, 2.8 Hz), 7.76 (1H, dd, J=8.0 Hz, 8.0 Hz), 7.85–7.92 (1H, m), 8.04–8.10 (2H, m)

Preparation 37

To a solution of methyl 3-acetoxymethyl-5-(pyrrol-1-yl)benzoate (4.68 g) in dichloromethane (94 ml) was added chlorosulfonyl isocyanate (2.1 ml) at −20° C. under nitrogen. After being stirred for 1 hour at −20° C., to the reaction mixture was added N,N-dimethylformamide (14.0 ml) at −20° C. After being stirred for 1 hour at −20° C. to −10° C., the reaction mixture was poured into water and the product was extracted with ethyl acetate. The extract was washed with brine and dried over magnesium sulfate. The solvent was evaporated in vacuo and the residue was purified by column chromatography on silica gel eluting with a mixture of hexane and ethyl acetate (5:1). The eluted fractions containing the desired product were collected and evaporated in vacuo to afford methyl 3-acetoxymethyl-5-(2-cyanopyrrol-1-yl)benzoate (4.26 g).

mp: 85°–86° C.

IR (Nujol): 2220, 1735, 1720 cm$^{-1}$

NMR (DMSO-d$_6$, δ): 2.11 (3H, s), 3.91 (3H, s), 5.24 (2H, s), 6.4–6.6 (1H, m), 7.2–7.3 (1H, m), 7.6–7.7 (1H, m), 7.9–8.1 (3H, m)

MASS (m/z): 299 (M$^+$+1)

Preparation 38

To the mixture of methyl 3-(2-dimethylaminomethyl-pyrrol-1-yl)benzoate (1.0 g) in dichloromethane (15 ml) was added 4N-hydrogen chloride in ethyl acetate solution (0.97 ml) under ice-cooling and the mixture was stirred for 5 minutes at the same temperature. To the mixture was added dropwise chlorosulfonyl isocyanate (0.4 ml) under ice-cooling and the mixture was stirred for 1 hour at the same temperature. To the mixture was added dropwise N,N-dimethylformamide (3.0 ml) under ice-cooling and the mixture was stirred for 1 hour at the same temperature. The reaction mixture was poured into a mixture of dichloromethane and water, and the separated aqueous layer was adjusted to pH 12 with 5N-sodium hydroxide solution. The aqueous layer was extracted with ethyl acetate. The extract was washed with brine, dried over magnesium sulfate and evaporated in vacuo to give methyl 3-(2-cyano-5-dimethylaminomethylpyrrol-1-yl)benzoate (1.1 g) as an oil.

IR (Nujol): 3450, 2220, 1728 cm$^{-1}$

NMR (DMSO-d$_6$): 2.04 (6H, s), 3.21 (2H, s), 3.90 (3H, s), 6.37 (1H, d, J=3.9 Hz), 7.17 (1H, d, J=3.9 Hz), 7.74 (1H, dd, J=7.9 Hz, 7.9 Hz), 7.78–7.86 (1H, m), 8.06–8.16 (2H, m)

Preparation 39

A solution of methyl 3-(2-methylthiophenyl)benzoate (1.4 g) in chloroform (21 ml) was stirred in an ice bath under nitrogen gas. m-Chloroperbenzoic acid (2.57 g) was slowly added thereto, and the mixture was stirred at room temperature for 5 hours. The reaction mixture was extracted with chloroform (70 ml). The extract was successively washed with an aqueous sodium iodide solution, an aqueous sodium thiosulfate solution, an aqueous sodium hydrogencarbonate solution and brine, and dried over magnesium sulfate. After evaporating the solvent, the crystalline residue was recrystallized from diethyl ether to afford methyl 3-(2-methylsulfonylphenyl)benzoate.

mp: 100°–102° C.

IR (Nujol): 1710, 1300, 1150, 950, 750 cm$^{-1}$

NMR (DMSO-d$_6$, δ): 2.87 (3H, s), 3.87 (3H, s), 7.44 (1H, dd, J=7.4 Hz, 1.4 Hz), 7.61–7.80 (4H, m), 7.96 (1H, dd, J=1.5 Hz, 1.5 Hz), 8.04 (1H, ddd, J=7.5 Hz, 1.6 Hz, 1.6 Hz), 8.12 (1H, dd, J=7.5 Hz, 1.5 Hz)

MASS (m/z): 291 (M$^+$+1)

Preparation 40

The mixture of methyl 3-(2-trichloroacetylpyrrol-1-yl)benzoate (10.0 g), benzyl alcohol (3.3 ml) and potassium carbonate (4.4 g) in N,N-dimethylformamide (30 ml) was stirred for 6 hours at ambient temperature. The reaction mixture was poured into water and the mixture was extracted with ethyl acetate. The extract was washed with water, dried over magnesium sulfate, and evaporated. The residue was purified by column chromatography on silica gel eluting with toluene. The eluted fractions containing the desired product were collected and evaporated in vacuo to give methyl 3-(2-benzyloxycarbonylpyrrol-1-yl)benzoate (8.35 g) as an oil.

IR (Film): 1700–1725 (br), 1590 cm$^{-1}$

NMR (DMSO-d$_6$, δ): 3.87 (3H, s), 5.12 (2H, s), 6.37 (1H, dd, J=2.7 Hz, 3.9 Hz), 7.14 (1H, dd, J=1.8 Hz, 3.9 Hz), 7.21–7.35 (6H, m), 7.57–7.69 (2H, m), 7.80–7.84 (1H, m), 7.93–8.02 (1H, m)

Preparation 41

The mixture of methyl 3-(pyrrol-1-yl)benzoate (20.0 g), dimethylamine hydrochloride (12.2 g) and paraformaldehyde (13.4 g) in ethanol (60 ml) was heated under reflux for 3 hours under stirring. The solvent was removed by concentration and the residue was added to the mixture of ethyl acetate and water. The mixture was adjusted to pH 12 with 5N-sodium hydroxide solution. The separated organic layer was washed with brine, dried over magnesium sulfate, and evaporated. The residue was purified by column chromatography on silica gel eluting with a mixture of chloroform and methanol (9:1, V/V). The eluted fractions containing the desired product were collected and evaporated in vacuo to give methyl 3-(2-dimethylaminomethylpyrrol-1-yl)benzoate (15.3 g) as an oil.

IR(Nujol): 1728, 1605, 1590 cm$^{-1}$

NMR (DMSO-d$_6$, 5): 2.13 (6H, s), 3.20 (2H, s), 3.88 (3H, s), 6.15–6.23 (2H, m), 7.04–7.10 (1H, m), 7.62 (1H, dd, J=7.9 Hz, 7.9 Hz), 7.80–7.88 (1H, m), 7.88–7.96 (1H, m), 8.29–8.34 (1H, m)

MASS (m/z): 259 (M$^+$+1)

Preparation 42

Methyl iodide (4.8 ml) was added dropwise to the mixture of methyl 3-(2-dimethylaminomethylpyrrol-1-yl)benzoate (10.0 g) and ethyl acetate (50 ml) at ambient temperature, and the mixture was stirred for 2 hours at the same temperature. The isolated precipitate was collected by filtration and dried to give methyl 3-(2-trimethylammoniomethylpyrrol-1-yl)benzoate iodide (13.52 g).

mp: 255–256° C. (dec.)

IR (Nujol): 3430, 1720, 1585 cm$^{-1}$

NMR (DMSO-d$_6$, 6): 2.76 (9H, s), 3.89 (3H, s), 7.54 (2H, s), 6.39 (1H, dd, J=2.9 Hz, 3.5 Hz), 6.69 (1H, dd, J=1.7 Hz, 3.5 Hz), 7.23 (1H, dd, J=1.7 Hz, 2.9 Hz), 7.65–7.80 (2H, m), 7.89–7.93 (1H, m), 8.00–8.10 (1H, m)

Preparation 43

To the mixture of methyl 3-(2-trimethylammoniomethyl-pyrrol- 1-yl)benzoate iodide (2.0 g) and 1,3-dimethyl-imidazolidin-2-one (6 ml) was added borane-pyridine complex (1.1 ml) and the mixture was stirred for 1.5 hours at 105° C. To the mixture was added dichloromethane, and the mixture was washed with water, 1N-hydrochloric acid and water successively. The mixture was dried over magnesium sulfate and evaporated in vacuo to give methyl 3-(2-methylpyrrol-1-yl)benzoate (1.01 g) as an oil.

IR (Nujol): 1725, 1588 cm$^{-1}$

NMR (DMSO-d$_6$, δ): 2.18 (3H, s), 3.89 (3H, s), 6.00–6.04 (1H, m), 6.09–6.15 (1H, m), 6.89–6.94 (1H, m), 7.55–8.10 (4H, m)

MASS (m/z): 216 (M$^+$+1)

Preparation 44

28% Ammonia aqueous solution (0.4 ml) was added to a mixture of methyl 3-(2-trichloroacetylpyrrol-1-yl)benzoate (1.0 g) and N,N-dimethylformamide (2 ml), and the mixture was stirred for 1.5 hours at ambient temperature. The mixture was poured into a mixture of ethyl acetate and water. The separated organic layer was washed with water, dried over magnesium sulfate and evaporated in vacuo. The residue was triturated with diisopropyl ether to give methyl 3-(2-carbamoylpyrrol-1-yl)benzoate (0.61 g).

mp: 157°–158° C.

IR (Nujol): 3400, 3300, 3200, 1715, 1650, 1610 cm$^{-1}$

NMR (DMSO-d$_6$, δ): 3.87 (3H, s), 6.22–6.29 (1H, m), 6.90–6.98 (2H, m), 7.09–7.14 (1H, m), 7.53–7.60 (2H, m), 7.63 (1H, s), 7.76 (1H, s), 7.87–7.96 (1H, m)

Preparation 45

1N-Sodium hydroxide solution (1.5 ml) was added to a mixture of methyl 3-(2-benzyloxycarbonylpyrrol-1-yl)benzoate (0.5 g) and dioxane (20 ml), and the mixture was stirred for 3 days at ambient temperature. The reaction mixture was poured into the mixture of ethyl acetate and water and the separated aqueous layer was adjusted to pH 1 with 6N-hydrochloric acid. The mixture was extracted with ethyl acetate and extract was washed with brine and dried over magnesium sulfate. The solvent was removed by concentration and the residue was triturated with n-hexane to give 3-(2-benzyloxycarbonylpyrrol-1-yl)benzoic acid (0.24 g).

mp: 161°–165° C.

IR (Nujol): 1710 cm$^{-1}$

NMR (DMSO-d$_6$, δ): 5.13 (2H, s), 6.36 (1H, dd, J=2.8 Hz, 3.9 Hz), 7.13 (1H, dd, J=1.7 Hz, 3.9 Hz), 7.21–7.37 (6H, m), 7.50–7.66 (2H, m), 7.78–7.83 (1H, m), 7.92–8.00 (1H, m), 13.10 (1H, m)

Preparation 46

The following compounds were obtained according to a similar manner to that of Preparation 45.

(1) 3-(3-Cyanopyrrol-1-yl)benzoic acid mp: 194°–196° C.

IR (Nujol): 2230, 1695, 1590 cm$^{-1}$

NMR (DMSO-d$_6$, δ): 6.76 (1H, dd, J=1.6 Hz, 3.1 Hz), 7.60–7.72 (2H, m), 7.87–7.98 (2H, m), 8.08–8.14 (1H, m), 8.31–8.37 (1H, m)

(2) 3-(2-Cyanopyrrol-1-yl)benzoic acid mp: 195°–196° C.

IR (Nujol): 2220, 1690–1705 (br), 1590 cm$^{-1}$

NMR (DMSO-d$_6$, δ): 6.48 (1H, dd, J=2.8 Hz, 3.9 Hz), 7.27 (1H, dd, J=1.6 Hz, 3.9 Hz), 7.64 (1H, dd, J=1.6 Hz, 2.8 Hz), 7.73 (1H, dd, J=8.1 Hz, 8.1 Hz), 7.81–7.89 (1H, m), 8.02–8.09 (2H, m)

MASS (m/z): 221 (M$^+$−1)

(3) 5-Cyano-3-(pyrrol-1-yl)benzoic acid mp: 181°–184° C.

IR (Nujol): 2230, 1700, 1600 cm$^{-1}$

NMR (DMSO-d$_6$, δ): 6.31–6.37 (2H, m), 7.55–7.62 (2H, m), 8.11 (1H, dd, J=1.4 Hz, 1.4 Hz), 8.31 (1H, dd, J=1.4 Hz, 2.3 Hz), 8.42 (1H, dd, J=1.4 Hz, 2.3 Hz)

Preparation 47

N-Chlorosuccinimide (2.7 g) was added to a mixture of methyl 3-(pyrrol-1-yl)benzoate (2.0 g) and N,N-dimethylformamide (20 ml) under ice-cooling and the mixture was stirred for 20 hours at ambient temperature. The reaction mixture was poured into a mixture of ethyl acetate and water, and the mixture was adjusted to pH 8 with potassium carbonate. The separated organic layer was washed with water, dried over magnesium sulfate and evaporated in vacuo to give methyl 3-(2,5-dichloropyrrol-1-yl)benzoate (2.44 g) as an oil.

IR (Film): 1725, 1590 cm$^{-1}$

NMR (DMSO-d$_6$, δ): 3.90 (3H, s), 6.40 (2H, s), 7.66–7.88 (3H, m), 8.09–8.18 (1H, m)

MASS (m/z): 270 (M$^+$+1)

Preparation 48

Phosphoryl chloride (5.5 ml) was dropwise added to N,N-dimethylformamide (4.6 ml) under ice-cooling and the mixture was stirred for 15 minutes at 40°–50° C. To the mixture was added a solution of methyl 3-(pyrrol-1-yl)benzoate (6.0 g) in N,N-dimethylformamide (30 ml) at ambient temperature and the whole was stirred for 3 hours at 110°–120° C. An ice-cooling mixture was poured into ice-water and the mixture was adjusted to pH 9 with potassium carbonate. The mixture was extracted with ethyl acetate. The extract was washed with brine, dried over magnesium sulfate and evaporated in vacuo. The residue was triturated with diisopropyl ether to give methyl 3-(2-formylpyrrol-1-yl)benzoate (5.31 g).

mp: 61°–64° C.

IR (Nujol): 1720, 1660, 1590 cm$^{-1}$

NMR (DMSO-d$_6$, δ): 3.89 (3H, s), 6.50 (1H, dd, J=2.6 Hz, 3.9 Hz), 7.28 (1H, dd, J=1.7 Hz, 3.9 Hz), 7.50–7.55 (1H, m), 7.65 (1H, dd, J=7.7 Hz, 7.7 Hz), 7.69–7.77 (1H, m), 7.88–7.92 (1H, m), 7.97–8.05 (1H, m), 9.54 (1H, s)

Preparation 49

The mixture of methyl 4-hydroxy-3-(pyrrol-1-yl)benzoate (4.0 g), acetone (40 ml) and p-toluenesulfonic acid (0.8 g) in toluene (80 ml) was heated under reflux for 15 hours under stirring. The solvent was removed by evaporation and to the residue was added a mixture of ethyl acetate and water. The mixture was adjusted to pH 8 with potassium carbonate and the separated organic layer was washed with brine, dried over magnesium sulfate and evaporated in vacuo. The residue was purified by column chromatography on silica gel eluting with a mixture of toluene and n-hexane (1:1, V/V). The eluted fractions containing the desired product were collected and evaporated in vacuo. The residue was triturated with a mixture of diisopropyl ether and n-hexane to give 8-methoxycarbonyl-4,4-dimethyl-4H-pyrrolo[2,1-c][1,4]-benzoxazine.

mp: 128°–129° C.

IR (Nujol): 1715 cm$^{-1}$

NMR (DMSO-d$_6$, δ): 1.58 (6H, s), 3.86 (3H, s), 6.10–6.17 (1H, m), 6.26–6.34 (1H, m), 7.14 (1H, d, J=8.4 Hz), 7.59–7.65 (1H, m), 7.71 (1H, dd, J=1.9 Hz, 8.4 Hz), 8.16 (1H, d, J=1.9 Hz)

MASS (m/z): 258 (M$^+$+1)

Preparation 50

Acetic anhydride (1.3 ml) was added to a mixture of aluminum chloride (2.7 g) and 1,2-dichloroethane (10 ml) under ice-cooling and the mixture was stirred for 20 minutes at the same temperature. To the mixture was added dropwise a mixture of methyl 3-(pyrrol-1-yl)benzoate (2.0 g) in dichloroethane (3 ml) for 10 minutes at 0° to 5° C., and the mixture was stirred for 3 hours at the same temperature. The reaction mixture was poured into an ice-water and the mixture was extracted with chloroform. The extract was washed with a saturated aqueous sodium bicarbonate solution and water. The organic layer was dried over magnesium sulfate and evaporated in vacuo to give methyl 3-(2-acetylpyrrol-1-yl)benzoate (0.94 g).

mp: 86°–87° C.

IR (Nujol): 1720, 1645 cm$^{-1}$

NMR (DMSO-d$_6$, δ): 2.42 (3H, s), 3.91 (3H, s), 6.64–6.70 (1H, m), 7.52–7.58 (1H, m), 7.68 (1H, dd, J=7.9 Hz, 7.9 Hz), 7.92 (1H, d, J=7.9 Hz), 7.96–8.04 (1H, m), 8.15–8.19 (1H, m), 8.31–8.35 (1H, m)

MASS (m/z): 244 (M$^+$+1)

Preparation 51

Trichloroacetyl chloride (15.5 ml) was added to a mixture of methyl 3-(pyrrol-1-yl)benzoate (14.0 g) and pyridine (16.9 ml) in 1,2-dichloroethane (70 ml) under ice-cooling and the mixture was stirred for 7 days at ambient temperature. The mixture was poured into a mixture of chloroform and water, and the mixture was adjusted to pH 1 with 6N-hydrochloric acid. The separated organic layer was washed with a saturated aqueous sodium bicarbonate solution and water. The mixture was dried over magnesium sulfate and evaporated in vacuo. The residue was triturated with diisopropyl ether to give methyl 3-(2-trichloroacetylpyrrol-1-yl)benzoate (21.23 g).

mp: 94°–95° C.

IR (Nujol): 1725, 1670, 1590 cm$^{-1}$

NMR (DMSO-d$_6$, δ): 3.89 (3H, s), 6.56 (1H, dd, J=2.6 Hz, 4.3 Hz), 7.60–7.71 (4H, m), 7.82 (1H, s), 8.01–8.10 (1H, m)

MASS (m/z): 346 (M$^+$+1)

Preparation 52

To a solution of 5-(pyrrol-1-yl)-3-methoxycarbonylbenzoic acid (9.37 g) in tetrahydrofuran (100 ml) was added triethylamine (6.4 ml) followed by slow addition of isobutyl chloroformate (5.9 ml) under nitrogen at −40° C. to −30° C. The reaction mixture was stirred below −20° C. for 45 minutes. Then, triethylamine hydrochloride was filtered off and washed with cold tetrahydrofuran, and the filtrate was added as quickly as possible to a suspension of sodium borohydride (4.35 g) in tetrahydrofuran-water (8:1, 80 ml) at 0° C. with vigorous stirring. The stirring was continued at ambient temperature for 5 hours, followed by acidification of the solution to pH 5. The tetrahydrofuran was removed under reduced pressure, and the product was extracted with ethyl acetate. The ethyl acetate extracts were washed with water and brine, dried over magnesium sulfate and evaporated under reduced pressure. The residue was purified by column chromatography on silica gel eluting with a mixture of chloroform and methanol (30:1). The eluted fractions containing the desired product were collected and evaporated in vacuo to give methyl 3-hydroxymethyl-5-(pyrrol-1-yl)benzoate (7.33 g).

mp: 83°–85° C.

IR (Nujol): 3200, 1710, 1600 cm$^{-1}$

NMR (DMSO-d$_6$, δ): 3.89 (3H, s), 4.63 (2H, d, J=5.8 Hz), 5.47 (1H, t, J=5.8 Hz), 6.2–6.4 (2H, m), 7.3–7.5 (2H, m), 7.7–8.0 (3H, m)

MASS (m/z): 232 (M$^+$+1)

Preparation 53

To a solution of methyl 3-hydroxymethyl-5-(pyrrol-1-yl)benzoate (2.0 g) in chloroform (30 ml) was added silver(I) oxide (8.0 g) and iodomethane (4.3 ml). The reaction mixture was stirred at 50° C. for 4.5 hours. After being cooled to room temperature, the slurry was filtered and the filtrate was evaporated in vacuo. The residue was purified by column chromatography on silica gel eluting with a mixture of hexane and ethyl acetate (10:1). The eluted fractions containing the desired product were collected and evaporated in vacuo to afford methyl 3-methoxymethyl-5-(pyrrol-1-yl)benzoate (1.72 g)) as an oil.

IR (Film): 2950, 1720, 1600 cm$^{-1}$

NMR (DMSO-d$_6$, δ): 3.35 (3H, s), 3.90 (3H, s), 4.54 (2H, s), 6.3–6.4 (2H, m), 7.4–7.5 (2H, m), 7.8–8.0 (3H, m)

MASS (m/z): 246 (M$^+$+1)

Preparation 54

To a solution of methyl 3-hydroxymethyl-5-(pyrrol-1-yl)benzoate (4.0 g) in pyridine (40 ml) was added acetic anhydride (4.9 ml) under ice cooling. After being stirred for 3 hours under ice cooling, the reaction mixture was poured into ice-water and the product was extracted with diethyl ether. The diethyl ether extracts were washed with water, 1N-hydrochloric acid and brine and dried over magnesium sulfate. The solvent was evaporated in vacuo and the residue was purified by column chromatography on silica gel eluting with a mixture of hexane and ethyl acetate (5:1). The eluted fractions containing the desired product were collected and evaporated in vacuo to afford methyl 3-acetoxymethyl-5-(pyrrol-1-yl)benzoate (4.68 g).

mp: 68°–70° C.

IR (Nujol): 1740, 1720, 1620, 1600 cm$^{-1}$

NMR (DMSO-d$_6$, δ): 2.11 (3H, s), 3.90 (3H, s), 5.19 (2H, s), 6.3–6.4 (2H, m), 7.4–7.5 (2H, m), 7.8–8.0 (3H, m)

MASS (m/z): 274 (M$^+$+1)

Preparation 55

The following compounds were obtained according to similar manners to those of Preparation 37 and 38.

(1) Methyl 3-(2-cyanopyrrol-1-yl)benzoate mp: 89°–90° C.

IR (Nujol): 2220, 1715, 1590 cm$^{-1}$

NMR (DMSO-d$_6$, δ): 3.91 (3H, s), 6.49 (1H, dd, J=2.8 Hz, 3.9 Hz), 7.28 (1H, dd, J=1.6 Hz, 3.9 Hz), 7.65 (1H, dd, J=1.6 Hz, 2.8 Hz), 7.76 (1H, dd, J=8.0 Hz, 8.0 Hz), 7.85–7.92 (1H, m), 8.04–8.10 (2H, m)

MASS (m/z): 227 (M$^+$+1)

(2) Methyl 3-(2-cyano-5-methylpyrrol-1-yl)benzoate mp: 82°–84° C.

IR (Nujol): 2220, 1715 cm$^{-1}$

NMR (DMSO-d$_6$, δ): 2.12 (3H, s), 3.90 (3H, s), 6.21 (1H, d, J=3.9 Hz), 7.11 (1H, d, J=3.9 Hz), 7.70–7.84 (2H, m), 7.92–7.96 (1H, m), 8.09–8.17 (1H, m)

MASS (m/z): 241 (M$^+$+1)

(3) Methyl 4-n-butyl-3-(2-cyanopyrrol-1-yl)benzoate

IR (Film): 2230, 1725 cm$^{-1}$

NMR (DMSO-d$_6$, δ): 0.76 (3H, t, J=7.2 Hz), 1.04–1.27 (2H, m), 1.27–1.47 (2H, m), 2.37–2.55 (2H, m), 3.88 (3H, s), 6.47 (1H, dd, J=2.7 Hz, 4.0 Hz), 7.22 (1H, dd, J=1.6 Hz, 4.0 Hz), 7.43 (1H, dd, J=1.6 Hz, 2.7 Hz), 7.66 (1H, d, J=8.1 Hz), 7.84 (1H, d, J=1.8 Hz), 8.07 (1H, dd, J=1.8 Hz, 8.1 Hz)

(4) Dimethyl 5-(2-cyanopyrrol-1-yl)isophthalate mp: 208° C.

IR (Nujol): 2220, 1727 cm$^{-1}$

NMR (DMSO-d$_6$, δ): 3.94 (6H, s), 6.48–6.54 (1H, m), 7.29–7.33 (1H, m), 7.72–7.76 (1H, m), 8.33 (2H, s), 8.53 (1H, s)

Preparation 56

A mixture of dimethyl 5-(pyrrol-1-yl)isophthalate (80.0 g) and potassium hydroxide (20.2 g) in methanol (3.1 l) was stirred for 62 hours at 68° C. After being cooled to room temperature, the solvent was evaporated in vacuo. The residue was dissolved in water and the solution was washed with ethyl acetate. The aqueous layer was acidified with hydrochloric acid (25.5 ml) and extracted with ethyl acetate. The organic layer was washed with brine and dried over magnesium sulfate. The solvent was evaporated in vacuo and the residue was triturated with diethyl ether to afford 3-methoxycarbonyl-5-(pyrrol-1-yl)benzoic acid (53.7 g).

mp: 178°–179° C.

IR (Nujol): 3050, 1720, 1680 cm$^{-1}$

NMR (DMSO-d$_6$, δ): 3.93 (3H, s), 6.3–6.4 (2H, m), 7.5–7.6 (2H, m), 8.2–8.4 (3H, m), 13.6 (1H, br s)

MASS (m/z): 244 (M$^+$−1)

Preparation 57

A mixture of dimethyl 5-(pyrrol-1-yl)isophthalate (1.0 g) and 4-(2-aminoethyl)morpholine (0.65 g) was heated at 120° C. for 2 hours. The residue was purified by column chromatography on silica gel (50 g) with chloroform-methanol (30:1) as an eluent. The fractions containing object product were combined and evaporated in vacuo. The crystalline residue was recrystallized from ethanol-ether to afford N-[2-(morpholin-4-yl)ethyl]-3-methoxycarbonyl-5-(pyrrol-1-yl)benzamide (353 mg).

mp: 144°–146° C.

IR (Nujol): 3250, 1725, 1635, 1250, 720 cm$^{-1}$

NMR (DMSO-d$_6$, δ): 2.30–2.60 (6H, m), 3.35–3.55 (2H, m), 3.55–3.70 (4H, m), 3.93 (3H, m), 6.30–6.40 (2H, m), 7.45–7.55 (2H, m), 8.15–8.27 (3H, m), 8.76 (1H, t, J=5.6 Hz)

MASS (m/z): 358 (M+1)

Preparation 58

The following compound was obtained according to a similar manner to that of Preparation 57.

N-[3-(morpholin4-yl)propyl]3-methoxycarbonyl-5-(pyrrol-1-yl)benzamide mp: 126°–127° C.

IR (Nujol): 3250, 1730, 1635, 1250, 720 cm$^{-1}$

NMR (DMSO-d$_6$, δ): 1.6–1.8 (2H, m), 2.3–2.4 (6H, m), 3.3–3.4 (2H, m), 3.5–3.6 (4H, m), 3.93 (3H, m), 6.32–6.35 (2H, m), 7.49–7.52 (2H, m), 8.15–8.17 (1H, m), 8.23–8.28 (2H, m), 8.79 (1H, t,J=5.4 Hz)

MASS (m/z): 372 (M+1)

Preparation 59

The following compounds were obtained according to similar manners to those of

Preparations 5 and 17.

(1) Methyl 2-methoxy-5-(pyrrol-1-yl)benzoate
mp: 96°–98° C.
IR (Nujol): 1730 cm$^{-1}$
NMR (DMSO-d$_6$, δ): 3.82 (3H, s), 3.85 (3H, s), 6.20–6.28 (2H, m), 7.23 (1H, d, J=9.1 Hz), 7.26–7.33 (2H, m), 7.67–7.78 (2H, m)
(+) APCI MASS (m/z): 232 [M+H]$^+$
Elemental Analysis Calcd. for C$_{13}$H$_{13}$NO$_3$: C 67.52, H 5.67, N 6.06 Found: C 67.45, H 5.75, N 6.04

(2) Methyl 2-hydroxy-5-(pyrrol-1-yl)benzoate
mp: 80°–81° C.
IR (Nujol): 3170, 1670, 1617 cm$^{-1}$
NMR (DMSO-d$_6$, δ): 3.91 (3H, s), 6.21–6.27 (2H, m), 7.09 (1H, d, J=8.8 Hz), 7.23–7.29 (2H, m), 7.73 (1H, dd, J=2.8 Hz, 8.8 Hz), 7.81 (1H, d, J=2.8 Hz), 10.40 (1H, s)
(+) APCI MASS (m/z): 218 [M+H]$^+$
Elemental Analysis Calcd. for C$_{12}$H$_{11}$NO$_3$: C 66.35, H 5.10, N 6.45 Found: C 66.63, H 5.16, N 6.45

(3) Methyl 2-nitro-5-(pyrrol-1-yl)benzoate
mp: 86°–87° C.
IR (Nujol): 1727, 1585, 1325 cm$^{-1}$
NMR (DMSO-d$_6$, δ): 3.91 (3H, s), 6.36–6.42 (2H, m), 7.61–7.70 (2H, m), 8.01 (1H, dd, J=2.6 Hz, 8.9 Hz), 8.06 (1H, d, J=2.6 Hz), 8.23 (1H, d, J=8.9 Hz)
Elemental Analysis Calcd. for C$_{12}$H$_{10}$N$_2$O$_4$: C 58.54, H 4.09, N 11.38 Found: C 58.66, H 3.90, N 11.21

(4) Methyl 5-(pyrrol-1-yl)-3-sulfamoyl benzoate
mp: 178°–179° C.
IR (Nujol): 3310, 3220, 1702, 1605, 1350, 1168 cm$^{-1}$
NMR (DMSO-d$_6$, δ): 3.94 (3H, s), 6.34–6.39 (2H, m), 7.48–7.54 (2H, m), 7.60 (2H, s), 8.17–8.28 (3H, m)

(5) Dimethyl 2-(pyrrol-1-yl)terephthalate
mp: 55°–57° C.
IR (Nujol): 1715 (br) cm$^{-1}$
NMR (DMSO-d$_6$, δ): 3.69 (3H, s), 3.91 (3H, s), 6.23–6.29 (2H, m), 6.95–7.01 (2H, m), 7.88 (1H, d, J=8.1 Hz), 7.91 (1H, d, J=1.6 Hz), 8.01 (1H, dd, J=1.6 Hz, 8.1 Hz)
Elemental Analysis Calcd. for C$_{14}$H$_{13}$NO$_4$: C 64.86, H 5.05, N 5.40 Found: C 64.57, H 5.15, N 5.38

(6) Methyl 4-acetylaminomethyl-3-(pyrrol-1-yl)benzoate
mp: 135°–137° C.
IR (Nujol): 3280, 1730, 1630 cm$^{-1}$
NMR (DMSO-d$_6$, δ): 1.88 (3H, s), 3.86 (3H, s), 4.17 (2H, d, J=5.8 Hz), 6.24–6.30 (2H, m), 7.00–7.06 (2H, m), 7.55 (1H, d, J=8.2 Hz), 7.75 (1H, d, J=1.7 Hz), 7.97 (1H, dd, J=1.7 Hz, 8.2 Hz), 8.38 (1H, t, J=5.8 Hz)
Elemental Analysis Calcd. for C$_{15}$H$_{16}$N$_2$O$_3$: C 66.16, H 5.92, N 10.29 Found: C 66.35, H 6.05, N 9.95

(7) Methyl 2-(pyrrol-1-yl)isonicotinate
mp: 51°–53° C.
IR (Nujol): 1724, 1605 cm$^{-1}$
NMR (DMSO-d$_6$, δ): 3.94 (3H, s), 6.31–6.37 (2H, m), 7.65 (1H, d, J=5.0 Hz), 7.74–7.80 (2H, m), 8.04 (1H, s), 8.62 (1H, d, J=5.0 Hz)
Elemental Analysis Calcd. for C$_{11}$H$_{10}$N$_2$O$_2$: C 65.34, H 4.98, N 13.85 Found C 65.24, H 4.74, N 13.59

(8) Methyl 4-(pyrrol-1-yl)pyridine-2-carboxylate
mp: 109°–111° C.
IR (Nujol): 3100, 1715, 1590 cm$^{-1}$
NMR (DMSO-d$_6$, δ): 3.92 (3H, s), 6.36–6.41 (2H, m), 7.68–7.74 (2H, m), 7.92 (1H, dd, J=2.4 Hz, 5.5 Hz), 8.21 (1H, d, J=2.4 Hz), 8.69 (1H, d, J=5.5 Hz)
(+) APCI MASS (m/z): 203 [M+H]$^+$ (9) Methyl 2-hydroxy-3-(pyrrol-1-yl)benzoate
mp: 41°–42° C.
IR (Nujol): 1683 cm$^{-1}$
NMR (DMSO-d$_6$, δ): 3.93 (3H, s), 6.19–6.26 (2H, m), 7.05 (1H, dd, J=7.9 Hz, 7.9 Hz), 7.08–7.17 (2H, m), 7.64 (1H, dd, J=1.7 Hz, 7.9 Hz), 7.79 (1H, dd, J=1.7 Hz, 7.9 Hz), 11.17 (1H, s)

(10) Methyl 4-hydroxymethyl-3-(pyrrol-1-yl)benzoate
IR (Film): 3420, 1720, 1575 cm$^{-1}$
NMR (DMSO-d$_6$, δ): 3.87 (3H, s), 4.44 (2H, d, J=5.4 Hz), 5.48 (1H, t, J=5.4 Hz), 6.23–6.29 (2H, m), 7.00–7.06 (2H, m), 7.75 (1H, d, J=1.7 Hz), 7.78 (1H, d, J=8.1 Hz), 8.00 (1H, dd, J=1.7 Hz, 8.1 Hz)

Preparation 60

The following each two stereoisomers were obtained according to a similar manner to that of Preparation 34.

(1)

(A) Methyl 3-[2-(E)-hydroxyiminoethyl)pyrrol-1-yl]benzoate
mp: 121°–122° C.
IR (Nujol): 1717 cm$^{-1}$
NMR (DMSO-d$_6$, δ): 2.10 (3H, s), 3.90 (3H, s), 6.54 (1H, dd, J=1.6 Hz, 3.0 Hz), 7.44–7.49 (1H, m), 7.63 (1H, dd, J=7.9 Hz, 7.9 Hz), 7.76–7.80 (1H, m), 7.84 (1H, d, J=7.9 Hz), 7.89–7.93 (1H, m), 8.09 (1H, d, J=1.6 Hz), 10.61 (1H, s)
Elemental Analysis Calcd. for C$_{14}$H$_{14}$N$_2$O$_3$: C 65.11, H 5.46, N 10.85 Found: C 65.26, H 5.54, N 10.78

(B) Methyl 3-[2-(Z)-1-hydroxyiminoethyl)pyrrol-1-yl]benzoate
mp: 120°–122° C.
IR (Nujol): 1717 cm$^{-1}$
NMR (DMSO-d$_6$, δ): 2.12 (3H, s), 3.90 (3H, s), 6.75–6.79 (1H, m), 7.46–7.51 (1H, m), 7.64 (1H, dd, J=7.9 Hz, 7.9 Hz), 7.84–7.97 (2H, m), 8.03–8.09 (2H, m), 10.73 (1H, s)
Elemental Analysis Calcd. for C$_{14}$H$_{14}$N$_2$O$_3$: C 65.11, H 5.46, N 10.85 Found: C 64.72, H 5.37, N 10.59

(2)

(A) Methyl 3-((E)-2-methoxyiminomethylpyrrol-1-yl)benzoate
IR (Film): 1728 cm$^{-1}$
NMR (DMSO-d$_6$, δ): 3.69 (3H, s), 3.89 (3H, s), 6.31–6.37 (1H, m), 6.68–6.74 (1H, m), 7.20–7.25 (1H, m), 7.64–7.70 (2H, m), 7.82–7.87 (1H, m), 7.89 (1H, s), 7.95–8.04 (1H, m)
(+) APCI MASS (m/z): 259 [M+H]$^+$ (B) Methyl 3-((Z)-2-methoxyiminomethylpyrrol-1-yl)benzoate
IR (Film): 1720, 1605 cm$^{-1}$
NMR (DMSO-d$_6$, δ): 3.89 (3H, s), 3.92 (3H, s), 6.36–6.42 (1H, m), 7.05 (1H, s), 7.18–7.27 (2H, m), 7.67–7.72 (2H, m), 7.81–7.86 (1H, m), 8.01–8.08 (1H, m)
(+) APCI MASS (m/z): 259 [M+H]$^+$ Preparation 61

The solution of methyl 3-(2-formylpyrrol-1-yl)benzoate (1.0 g) and benzyl (triphenylphosphoranylidene)acetate (1.8 g) in tetrahydrofuran (10 ml) were heated under reflux for 30 hours. After evaporating the solvent, the residue was purified by column chromatography on silica gel eluting with toluene. The fractions containing the desired product were collected and evaporated in vacuo to give methyl 3-[2-((E)-2-benzyloxycarbonylethenyl)pyrrol-1-yl]benzoate (0.77 g) as an oil.

IR (Film): 1700–1725 (br), 1620 cm$^{-1}$
NMR (DMSO-d$_6$, δ): 3.89 (3H, s), 5.13 (2H, s), 6.30 (1H, d, J=15.7 Hz), 6.38–6.44 (1H, m), 7.09–7.28 (3H, m), 7.34 (5H, s), 7.65–7.80 (2H, m), 7.84–7.88 (1H, m), 8.04–8.12 (1H, m)

Preparation 62

10% Palladium on carbon (0.25 g) was added to the solution of methyl 3-[2-((E)-2-benzyloxycarbonylethenyl)pyrrol-1-yl]benzoate (2.5 g) in methanol (50 ml) and the mixture was subjected to catalytic reduction at the ambient temperature under atmospheric pressure. The catalyst was removed by filtration and the filtrate was evaporated in vacuo. The residue was triturated with diisopropyl ether to give methyl 3-[2-(2-carboxyethyl)pyrrol-1-yl]benzoate (1.02 g).

mp: 126°–128° C.

IR (Nujol): 1728, 1703 cm$^{-1}$

NMR (DMSO-d$_6$, δ): 2.45 (2H, t, J=7 Hz), 2.73 (2H, t, J=7.0 Hz), 3.88 (3H, s), 6.00–6.07 (1H, m), 6.11–6.17 (1H, m), 6.87–6.92 (1H, m), 7.62–7.73 (2H, m), 7.84 (1H, s), 7.95–8.02 (1H, m)

Preparation 63

10% Palladium on carbon (0.5 g) was added to a solution of methyl 4-benzyloxycarbonylmethoxy3-(pyrrol-1-yl)benzoate (5.0 g) in methanol (50 ml) and tetrahydrofuran (20 ml) and the mixture was subjected to catalytic reduction at ambient temperature under atmospheric pressure. The catalyst was removed by filtration and filtrate was evaporated in vacuo. To the residue was added a mixture of ethyl acetate and water, and the mixture was adjusted to pH 8 with potassium carbonate. The separated aqueous layer was adjusted to pH 2 with 6N-hydrochloric acid and the mixture was extracted with ethyl acetate. The extract layer was washed with brine, dried over magnesium sulfate and evaporated in vacuo to give methyl 4-carboxymethoxy3-(pyrrol-1-yl)benzoate (2.26 g).

mp: 98°–102° C.

IR (Nujol): 1715, 1605 cm$^{-1}$

NMR (DMSO-d$_6$, δ): 3.84 (3H, s), 4.92 (2H, s), 6.20–6.26 (2H, m), 7.16–7.21 (2H, m), 7.26 (1H, d, J=8.6 Hz), 7.83 (1H, d, J=2.0 Hz), 7.88 (1H, dd, J=2.0 Hz, 8.6 Hz), 13.21 (1H, s)

Preparation 64

The following compound was obtained according to a similar manner to that of Preparation 4.

Methyl 5-amino-3-sulfamoylbenzoate mp: 163°–165° C.

IR (Nujol): 3480, 3380, 3280, 3220, 1700, 1330, 1165 cm$^{-1}$

NMR (DMSO-d$_6$, δ): 3.85 (3H, s), 5.89 (2H, s), 7.20–7.25 (1H, m), 7.30–7.37 (3H, m), 7.50–7.55 (1H, m)

Preparation 65

The mixture of methyl 5-cyano-3-(pyrrol-1-yl)benzoate (3.0 g), sodium azide (5.2 g) and ammonium chloride (4.3 g) in N,N-dimethylformamide (12 ml) was stirred for 4 hours at 120°–125° C. The mixture was added to the ice-water (100 ml) and to the mixture was added sodium nitrite (5.5 g). The mixture was adjusted to pH 1 with 6N-hydrochloric acid and stirred for 30 minutes. The mixture was extracted with ethyl acetate. The extract layer was washed with brine and dried over magnesium sulfate. The solvent was removed by concentration and the residue was triturated with diisopropyl ether to give methyl 3-(pyrrol-1-yl)-5-(1H-tetrazol-5-yl)benzoate (3.35 g).

mp: 217°–218° C.

IR (Nujol): 1720, 1600 cm$^{-1}$

NMR (DMSO-d$_6$, δ): 3.95 (3H, s), 6.34–6.40 (2H, m), 7.51–7.56 (2H, m), 8.16–8.22 (1H, m), 8.40–8.48 (2H, m)

Preparation 66

The following compound was obtained according to a similar manner to that of

Preparation 65.

Methyl 3-(1H-tetrazol-5-yl)benzoate mp: 178°–179° C.

IR (Nujol): 3150, 1692 cm$^{-1}$

NMR (DMSO-d$_6$, δ): 3.93 (3H, s), 7.78 (1H, dd, J=7.8 Hz, 7.8 Hz), 8.11–8.20 (1H, m), 8.28–8.38 (1H, m), 8.65 (1H, dd, J=1.5 Hz, 1.5 Hz)

(–) APCI MASS (m/z): 203 [M–H]$^-$

Elemental Analysis Calcd. for C$_9$H$_8$N$_4$O$_2$: C 52.94, H 3.95, N 27.44 Found: C 52.61, H 3.81, N 27.49

Preparation 67

The mixture of methyl 4-hydroxy-3-(pyrrol-1-yl)benzoate (1.5 g), 2-oxo-1,3-dioxolane (0.61 g) and tetraethylammonium iodide (0.38 g) was heated at 140° C. for 3 hours. The resultant mixture was dissolved in the solution of ethyl acetate and tetrahydrofuran. The solution was washed with water and dried over magnesium sulfate. Evaporation of the solvent gave the residue, which was purified by column chromatography on silica gel eluting with the solution of chloroform and ethyl acetate (9:1, V/V). The eluted fractions containing the desired product were collected and evaporated in vacuo to give methyl 4-(2-hydroxyethoxy)-3-(pyrrol-1-yl)benzoate (1.25 g) as an oil.

IR (Film): 3420, 1710, 1607 cm$^{-1}$

NMR (DMSO-d$_6$, δ): 3.67–3.80 (2H, m), 3.84 (3H, s), 4.19 (2H, t, J=4.8 Hz), 4.92 (1H, t, J=5.2 Hz), 6.18–6.25 (2H, m), 7.18–7.25 (2H, m), 7.34 (1H, d, J=8.7 Hz), 7.82 (1H, d, J=2.1 Hz), 7.88 (1H, dd, J=2.1 Hz, 8.7 Hz)

(+) APCI MASS (m/z): 262 [M+H]$^+$

Preparation 68

The following compound was obtained according to a similar manner to that of

Preparation 67.

Methyl 3-(2-hydroxyethoxy)-5-phenylbenzoate

IR (Neat): 3400, 1800, 1710, 1590 cm$^{-1}$

NMR (DMSO-d$_6$, δ): 3.74–3.80 (2H, m), 3.89 (3H, s), 3.97–4.14 (2H, m), 4.90–4.96 (1H, m), 7.46–7.78 (8H, m)

(+) APCI MASS (m/z): 273 [M+H]$^+$

Preparation 69

Benzylbromide (2.9 ml) was added to the mixture of methyl 4-hydroxy-3-(pyrrol-1-yl)benzoate (5.0 g) and potassium t-butoxide (2.7 g) in N,N-dimethylformamide (40 ml) under ice-cooling and the mixture was stirred for 5 hours at ambient temperature. The reaction mixture was poured into water and extracted with ethyl acetate. The extract layer was washed with brine and dried over magnesium sulfate. The solvent was removed by concentration. The residue was crystallized from the mixture of toluene and diisopropyl ether and collected by filtration to give methyl 4-benzyloxy3-(pyrrol-1-yl)benzoate (4.2 g).

mp: 103°–104° C.

IR (Nujol): 1710, 1605 cm$^{-1}$

NMR (DMSO-d$_6$, δ): 3.84 (3H, s), 5.28 (2H, s), 6.18–6.24 (2H, m), 7.08–7.15 (2H, m), 7.30–7.47 (6H, m), 7.83 (1H, d, J=2.1 Hz), 7.92 (1H, dd, J=2.1 Hz, 8.6 Hz)

Preparation 70

The following compounds were obtained according to a similar manner to that of

Preparation 69.

(1) Methyl 4-methoxy-3-(pyrrol-1-yl)benzoate mp: 74°–75° C.

IR (Nujol): 1712, 1698, 1605 cm$^{-1}$

NMR (DMSO-d$_6$, δ): 3.86 (3H, s), 3.90 (3H, s), 6.19–6.25 (2H, m), 7.05–7.10 (2H, m), 7.34 (1H, d, J=8.7 Hz), 7.80 (1H, d, J=2.1 Hz), 7.94 (1H, dd, J=2.1 Hz, 8.7 Hz)

Elemental Analysis Calcd. for C$_{13}$H$_{13}$NO$_3$: C 67.52, H 5.67, N 6.06 Found: C 67.68, H 5.82, N 6.05

(2) Methyl 4-benzyloxycarbonylmethoxy-3-(pyrrol-1-yl) benzoate

IR (Film): 1720 (br), 1605 cm$^{-1}$

NMR (DMSO-d$_6$, δ): 3.85 (3H, s), 5.10 (2H, s), 5.21 (2H, s), 6.18–6.24 (2H, m), 7.14–7.20 (2H, m), 7.30 (1H, d, J=8.9 Hz), 7.34–7.42 (5H, m), 7.81–7.90 (2H, m)

Preparation 71

The following compounds were obtained according to similar manners to those of Preparations 37 and 38.

(1) 8-Methoxycarbonyl1-cyano-4,4-dimethyl-4H-pyrrolo[2,1-c][1,4]benzoxazine mp: 114°–116° C.

IR (Nujol): 2220, 1720 cm$^{-1}$

NMR (DMSO-d$_6$, δ): 1.62 (6H, s), 3.88 (3H, s), 6.44 (1H, d, J=4.0 Hz), 7.26 (1H, d, J=8.5 Hz), 7.36 (1H, d, J=4.0 Hz), 7.86 (1H, dd, J=1.9 Hz, 8.5 Hz), 8.68 (1H, d, J=1.9 Hz)

(2) Methyl 3-(2-cyanothiophen-3-yl)benzoate mp: 87°–88° C.

IR (Nujol): 2200, 1720, 740 cm$^{-1}$

NMR (DMSO-d$_6$, δ): 3.90 (3H, s), 7.65 (1H, d, J=5.1 Hz), 7.72 (1H, dd, J=7.8, 7.8 Hz), 8.00–8.10 (2H, m), 8.18 (1H, d, J=5.1 Hz), 8.30 (1H, s)

(+) APCI MASS (m/z): 244 [M+H]$^+$

Elemental Analysis Calcd. for $C_{13}H_9NO_2S$: C 64.18, H 3.73, N 5.76 Found: C 64.16, H 3.50, N 5.67

(3) Methyl 3-(2-cyanofuran-3-yl)benzoate mp: 114°–115° C.

IR (Nujol): 2220, 1720, 1500, 1420, 1260 cm$^{-1}$

NMR (DMSO-d$_6$, δ): 3.91 (3H, s), 7.37 (1H, d, J=1.9 Hz), 7.72 (1H, dd, J=7.8, 7.8 Hz), 8.01–8.08 (2H, m), 8.20 (1H, d, J=1.9 Hz), 8.33 (1H, s)

(+) APCI MASS (m/z): 228 [M+H]$^+$ (4) 6-Methoxycarbonyl-1-cyano-4H-pyrrolo[2,1-c][1,4]benzoxazine mp: 141°–144° C.

IR (Nujol): 2210, 1725 cm$^{-1}$

NMR (DMSO-d$_6$, δ): 3.84 (3H, s), 5.29 (2H, s), 6.37 (1H, d, J=4.0 Hz), 7.31 (1H, d, J=8.0 Hz, 8.0 Hz), 7.36 (1H, d, J=4.0 Hz), 7.64 (1H, dd, J=1.5 Hz, 8.0 Hz), 8.13 (1H, dd, J=1.5 Hz, 8.0 Hz)

(+) APCI MASS (m/z): 255 (M+H)$^+$

Preparation 72

The following compound was obtained according to a similar manner to that of Preparation 41.

8-Methoxycarbonyl-1-dimethylaminomethyl-4,4-dimethyl-4H-pyrrolo[2,1-c][1,4]benzoxazine IR (Film): 1715 (br), 1610, 1590 cm$^{-1}$ NMR (DMSO-d$_6$, δ): 1.56 (6H, s), 2.29 (6H, s), 3.35 (2H, s), 3.85 (3H, s), 6.06 (1H, d, J=3.5 Hz), 6.21 (1H, d, J=3.5 Hz), 7.14 (1H, d, J=8.4 Hz), 7.73 (1H, dd, J=2.0 Hz, 8.4 Hz), 8.91 (1H, d, J=2.0 Hz)

(+) APCI MASS (m/z): 315 [M+H]$^+$

Preparation 73

The following compounds were obtained according to a similar manner to that of Preparation 2.

(1) Methyl 4-chloro-5-nitro-3-sulfamoyl benzoate mp: 138°–139° C.

IR (Nujol): 3380, 3280, 1728, 1600, 1350, 1168 cm$^{-1}$

NMR (DMSO-d$_6$, δ): 3.94 (3H, s), 8.14 (2H, s), 8.68 (1H, d, J=2.1 Hz), 8.73 (1H, d, J=2.1 Hz)

(2) Methyl 3-(5-aminopyrazol-1-yl)benzoate mp: 160°–162° C.

IR (Nujol): 3370, 3290, 3200, 1700, 1633 cm$^{-1}$

NMR (DMSO-d$_6$, δ): 3.89 (3H, s), 5.46 (2H, s), 5.52 (1H, d, J=1.8 Hz), 7.34 (1H, d, J=1.8 Hz), 7.63 (1H, dd, J=7.9 Hz, 7.9 Hz), 7.83–7.97 (2H, m), 8.17–8.23 (1H, m)

(3) Methyl 3-(3-nitrophenyl)benzoate mp: 90°–91° C.

IR (Nujol): 1720, 1535, 1350 cm$^{-1}$

NMR (DMSO-d$_6$, δ): 3.91 (3H, s), 7.68 (1H, dd, J=7.8 Hz, 7.8 Hz), 7.79 (1H, dd, J=8.0 Hz, 8.0 Hz), 8.0–8.3 (5H, m), 8.44 (1H, dd, J=2.0 Hz, 2.0 Hz)

(+) APCI MASS (m/z): 258 [M+H]$^+$ (4) Methyl 3-(2-chlorophenyl)benzoate mp: 46°–48° C.

IR (Nujol): 1720, 1300, 1240, 1110 cm$^{-1}$

NMR (DMSO-d$_6$, δ): 3.88 (3H, s), 7.44–7.48 (3H, m), 7.58–7.76 (3H, m), 7.98–8.04 (2H, m)

(+) APCI MASS (m/z): 247 [M+H]$^+$ (5) Methyl 3-(3-fluorophenyl)benzoate

IR (Neat): 1720, 1590, 1430, 1250, 1180 cm$^{-1}$

NMR (DMSO-d$_6$, δ): 3.91 (3H, s), 7.21–7.31 (1H, m), 7.52–7.68 (4H, m), 7.99 (2H, ddd, J=8.0 Hz, 1.7 Hz, 1.7 Hz), 8.21 (1H, dd, J=1.7 Hz, 1.7 Hz)

(+) APCI MASS (m/z): 231 [M+H]$^+$ (6) Methyl 3-(4-fluorophenyl)benzoate mp: 52°–54° C.

IR (Neat): 1720, 1600, 1510, 1440, 1300, 1110 cm$^{-1}$

NMR (DMSO-d$_6$, δ): 3.90 (3H, s), 7.25–7.38 (2H, m), 7.66 (1H, dd, J=7.5 Hz, 7.5 Hz), 7.71–7.80 (2H, m), 7.91–7.99 (2H, m), 8.17 (1H, dd, J=1.7 Hz, 1.7 Hz)

(+) APCI MASS (m/z): 231 [M+H]$^+$ (7) Methyl 3-(3-trifluoromethylphenyl)benzoate IR (Neat): 1720, 1440, 1330, 1280, 1240, 1110 cm$^{-1}$ NMR (DMSO-d$_6$, δ): 3.92 (3H, s), 7.62–7.81 (3H, m), 8.00–8.06 (4H, m), 8.23 (1H, dd, J=1.7 Hz, 1.7 Hz)

(+) APCI MASS (m/z): 281 [M+H]$^+$ (8) Methyl 3-(3-chlorophenyl)benzoate

IR (Neat): 1720, 1590, 1560, 1300, 1240, 1110 cm$^{-1}$

NMR (DMSO-d$_6$, δ): 3.91 (3H, s), 7.48–7.57 (2H, m), 7.59–7.69 (2H, m), 7.75 (1H, dd, J=1.6 Hz, 1.6 Hz), 7.95–8.01 (2H, m), 8.19 (1H, dd, J=1.6 Hz, 1.6 Hz)

(+) APCI MASS (m/z): 247 [M+H]$^+$ (9) Methyl 3-(furan-3-yl)benzoate

IR (Neat): 1720, 1610, 1510, 1430, 1250 cm$^{-1}$

NMR (DMSO-d$_6$, δ): 3.89 (3H, s), 7.04 (1H, dd, J=1.7 Hz, 0.9 Hz), 7.55 (1H, dd, J=7.7 Hz, 7.7 Hz), 7.79 (1H, dd, J=1.7 Hz, 1.7 Hz), 7.83–7.94 (2H, m), 8.16 (1H, dd, J=1.7 Hz, 0.9 Hz), 8.32 (1H, s)

(+) APCI MASS (m/z): 203 [M+H]$^+$

(10) Methyl 3-(3-methylphenyl)benzoate

IR (Film): 1720, 1435, 1310, 1250 cm$^{-1}$

NMR (DMSO-d$_6$, δ): 2.40 (3H, s), 3.90 (3H, s), 7.20–7.26 (1H, m), 7.34–7.65 (4H, m), 7.92–7.98 (2H, m), 8.16–8.19 (1H, m)

(+) APCI MASS (m/z): 227 [M+H]$^+$

(11) Methyl 3-(2-fluorophenyl)benzoate

IR (Film): 1720, 1310, 1240, 1110 cm$^{-1}$

NMR (DMSO-d$_6$, δ): 3.89 (3H, s), 7.30–7.70 (5H, m), 7.80–8.12 (3H, m)

(+) APCI MASS (m/z): 231 [M+H]$^+$

Preparation 74

A solution of methyl 4-hydroxy-3-(pyrrol-1-yl)benzoate (15.0 g), pyridine (8.4 ml) and acetic anhydride (9.8 ml) in dichloromethane (75 ml) was stirred for 15 hours at ambient temperature. To the reaction mixture was added the mixture of dichloromethane and water and the mixture was adjusted to pH 8 with 20% aqueous potassium carbonate solution. The separated organic layer was washed with 1N-hydrochloric acid and water respectively. The organic layer was dried over magnesium sulfate and evaporated in vacuo to give methyl 4-acetoxy-3-(pyrrol-1-yl)benzoate (15.9 g).

mp: 49°–51° C.

IR (Nujol): 1770, 1722 cm$^{-1}$

NMR (DMSO-d$_6$, δ): 2.20 (3H, s), 3.89 (3H, s), 6.25–6.31 (2H, m), 7.02–7.08 (2H, m), 7.50 (1H, d, J=9.0 Hz), 7.92–8.02 (2H, m)

Preparation 75

To a solution of phosphorus oxychloride (8.3 ml) and N,N-dimethylformamide (70 ml) was added methyl 4-acetoxy-3-(pyrrol-1-yl)benzoate (11.7 g) at ambient temperature and the mixture was stirred for 20 hours at the same temperature. The reaction mixture was poured into water and extracted with ethyl acetate. The extract layer was washed with water, dried over magnesium sulfate and evaporated in vacuo. The residue was dissolved in tetrahydrofuran. To the solution was added 28% methanolic sodium methoxide (9.7 ml) under ice-cooling and the mixture was stirred for 30 minutes at the same temperature. To the mixture was added acetic acid (6 ml) and evaporated in vacuo. To the residue was added a mixture of ethyl acetate and water, and adjusted to pH 7 with 20% aqueous potassium carbonate solution. The separated organic layer was washed with water, dried over magnesium sulfate and evaporated in vacuo. The residue was crystallized from toluene, collected by filtration and the precipitate was washed with ether to give methyl 3-(2-formylpyrrol-1-yl)-4-hydroxybenzoate (7.89 g).

mp: 147°–148° C.

IR (Nujol): 1715, 1640, 1600 cm$^{-1}$

NMR (DMSO-d$_6$, δ): 3.81 (3H, s), 6.40–6.46 (1H, m), 7.05–7.20 (2H, m), 7.25–7.33 (1H, m), 7.75 (1H, s), 7.83–7.93 (1H, m), 9.01 (1H, s), 11.02 (1H, s)

Preparation 76

Sodium borohydride (0.46 g) was added to a solution of methyl 3-(2-formylpyrrol-1-yl)-4-hydroxybenzoate (3.0 g) in tetrahydrofuran (30 ml) and the mixture was stirred for 1 hour at ambient temperature. The reaction mixture was added to the mixture of ethyl acetate and water and adjusted to pH 7.5 with 6N-hydrochloric acid. The separated organic layer was washed with water, dried over magnesium sulfate and evaporated in vacuo to give methyl 4-hydroxy-3-(2-hydroxymethylpyrrol-1-yl)benzoate (2.54 g).

mp: 152°–153° C.

IR (Nujol): 3400, 1695, 1603 cm$^{-1}$

NMR (DMSO-d$_6$, δ): 3.80 (3H, s), 4.21 (2H, s), 6.05–6.15 (2H, m), 6.70–6.76 (1H, m), 7.09 (1H, d, J=8.5 Hz), 7.79 (1H, d, J=2.1 Hz), 7.85 (1H, dd, J=2.1 Hz, 8.5 Hz)

Preparation 77

Diethyl azodicarboxylate (2.3 ml) was added dropwise to the mixture of methyl 4-hydroxy-3-(2-hydroxymethylpyrrol-1-yl)benzoate (2.5 g) and triphenylphosphine (4.0 g) in tetrahydrofuran (50 ml) under ice-cooling and the mixture was stirred for 2 hours at ambient temperature. The mixture was poured into the mixture of ethyl acetate and water. The separated organic layer was washed with brine and dried over magnesium sulfate. Evaporation of the solvent gave the residue, which was purified by column chromatography on silica gel eluting with chloroform. The eluted fractions containing the desired product were collected and evaporated in vacuo to give 8-methoxycarbonyl 4H-pyrrolo[2,1-c][1,4]-benzoxazine (0.61 g).

mp: 60°–62° C.

IR (Nujol): 1710 cm$^{-1}$

NMR (DMSO-d$_6$, δ): 3.87 (3H, s), 5.26 (2H, s), 6.08–6.14 (1H, m), 6.28–6.36 (1H, m), 7.18 (1H, d, J=8.5 Hz), 7.61–7.67 (1H, m), 7.70 (1H, dd, J=2.0 Hz, 8.5 Hz), 8.16 (1H, d, J=2.0 Hz)

Elemental Analysis Calcd. for $C_{13}H_{11}NO_3$: C 68.11, H 4.84, N 6.11 Found: C 67.83, H 4.92, N 6.12

Preparation 78

To the mixture of pyrrole (2.3 ml) and 60% sodium hydride (1.3 g) in N,N-dimethylformamide (50 ml) was added methyl 3-(bromomethyl)benzoate (5.0 g) under ice-cooling and the mixture was stirred for 3 hours at ambient temperature. The reaction mixture was poured into water and extracted with ethyl acetate. The extract layer was washed with water, dried over magnesium sulfate and evaporated to give methyl 3-(pyrrol-1-yl)methylbenzoate (4.14 g) as an oil.

IR (Film): 1715 cm$^{-1}$

NMR (DMSO-d$_6$, δ) 3.83 (3H, s), 5.19 (2H, s), 6.01–6.06 (2H, mn), 6.81–6.86 (2H, m), 7.40–7.58 (2H, m), 7.77 (1H, s), 7.86 (1H, d, J=6.7 Hz)

Preparation 79

The following compound was obtained according to a similar manner to that of Preparation 12.

Methyl 3-(3-dimethylaminopropenoyl)benzoate mp: 70°–73° C.

IR (Nujol): 1720, 1630 cm$^{-1}$

NMR (DMSO-d$_6$, δ): 2.95 (3H, s), 3.18 (3H, s), 3.89 (3H, s), 5.86 (1H, d, J=12.2 Hz), 7.60 (1H, dd, J=7.7 Hz, 7.7 Hz), 7.80 (1H, d, J=12.2 Hz), 8.02–8.11 (1H, m), 8.13–8.23 (1H, m), 8.41–8.46 (1H,

Preparation 80

The following compound was obtained according to a similar manner to that of Preparation 13.

Methyl 3-(pyrazol-3-yl)benzoate mp: 107°–108° C.

IR (Nujol): 3160, 1720 cm$^{-1}$

NMR (DMSO-d$_6$, δ): 3.89 (3H, s), 6.78–6.83 (1H, m), 7.57 (1H, dd, J=7.7 Hz, 7.7 Hz), 7.83 (1H, s), 7.89 (1H, d, J=7.7 Hz), 8.08 (1H, d, J=7.7 Hz), 8.42 (1H, s), 13.02 (1H, s)

Preparation 81

The mixture of methyl 3-(3-dimethylaminopropenoyl) benzoate (1.4 g), formamidine-acetate (2.8 g) and 28% methanolic sodium methoxide (5.2 ml) in methanol (38 ml) was heated under reflux for 64 hours under stirring. The solvent was removed by concentration and to the residue was added water. The mixture was adjusted to pH 9 with 20% aqueous potassium carbonate solution and the mixture was extracted with ethyl acetate. The extract layer was washed with brine, dried over magnesium sulfate and evaporated in vacuo. The residue was triturated with the solution of diisopropyl ether and n-hexane and the precipitate was collected by filtration to give methyl 3-(pyrimidin-4-yl) benzoate (0.8 g).

mp: 69°–71° C.

IR (Nujol): 1722, 1580 cm$^{-1}$

NMR (DMSO-d$_6$, δ): 3.92 (3H, s), 7.73 (1H, dd, J=7.8 Hz, 7.8 Hz), 8.14 (1H, d, J=7.8 Hz), 8.20 (1H, d, J=5.4 Hz), 8.48 (1H, d, J=7.8 Hz), 8.80 (1H, s), 8.93 (1H, d, J=5.4 Hz), 9.31 (1H, s)

(+) APCI MASS (m/z): 215 [M+H]$^+$

Elemental Analysis Calcd. for $C_{12}H_{10}N_2O_2$: C 67.28, H 4.70, N 13.08 Found C 67.00, H 4.68, N 12.93

Preparation 82

The following compounds were obtained according to a similar manner to that of Preparation 18.

(1) 2-Chlorophenyl-dihydroxyborane mp: 158°–160° C.

IR (Nujol): 3250, 1590 cm$^{-1}$

NMR (DMSO-d$_6$, δ): 7.22–7.43 (4H, m), 8.31 (2H, s)

(2) 3-Fluorophenyl-dihydroxyborane
mp: 213°–215° C.
IR (Nujol): 1580, 1350, 1190 cm$^{-1}$
NMR (DMSO-d$_6$, δ): 7.17–7.27 (1H, m), 7.35–7.64 (2H, m), 7.72 (1H, d, J=7.2 Hz)
(3) 4-Fluorophenyl-dihydroxyborane
mp: 254°–256° C.
IR (Nujol): 1600, 1400, 1220, 1150 cm$^{-1}$
NMR (DMSO-d$_6$, δ): 7.06–7.24 (2H, m), 7.81–8.03 (2H, m)
(4) 3-Chlorophenyl-dihydroxyborane
mp: 177°–179° C.
IR (Nujol): 1590, 1410 cm$^{-1}$
NMR (DMSO-d$_6$, δ) 7.33–7.50 (2H, m), 7.71–7.84 (2H, m)
(5) 3-Furyl-dihydroxyborane
mp: 128°–130° C.
IR (Nujol): 3200, 1560, 1500, 1320 cm$^{-1}$
NMR (DMSO-d$_6$, δ): 6.64 (1H, dd, J=1.6, 0.6 Hz), 7.62 (1H, dd, J=1.6 Hz, 1.3 Hz), 7.84 (1H, dd, J=1.3 Hz, 0.6 Hz), 7.91 (2H, s)
(6) 3-(4,4-Dimethyl-4,5-dihydrooxazol-2-yl)phenyldihydroxyborane
mp: 105°–107° C.
IR (Nujol): 3300 (br), 1640, 1360, 1180 cm$^{-1}$
NMR (DMSO-d$_6$, δ) 1.30 (6H, s), 4.11 (2H, s), 7.39–7.54 (1H, m), 7.82–8.38 (2H, m)
Preparation 83
The following compounds were obtained according to a similar manner to that of Preparation 20.
(1) 3-(2-Chlorophenyl)benzoic acid
mp: 185°–187° C.
IR (Nujol): 1670, 1320, 1250 cm$^{-1}$
NMR (DMSO-d$_6$, δ): 7.44–7.48 (3H, m), 7.57–7.73 (3H, m), 7.98–8.03 (2H, m), 13.16 (1H, br s)
(−) APCI MASS (m/z): 231 [M−H]$^-$
(2) 3-(3-Fluorophenyl)benzoic acid
mp: 145°–147° C.
IR (Nujol): 1680, 1580, 1320, 1260 cm$^{-1}$
NMR (DMSO-d$_6$, δ): 7.21–7.29 (1H, m), 7.52–7.66 (4H, m), 7.94–8.01 (2H, m), 8.21 (1H, dd, J=1.7, 1.7 Hz), 13.16 (1H, br s)
(+) APCI MASS (m/z): 217 [M+H]$^+$
(3) 3-(4-Fluorophenyl)benzoic acid
mp: 181°–183° C.
IR (Nujol): 1690, 1310, 1230 cm$^{-1}$
NMR (DMSO-d$_6$, δ): 7.27–7.38 (2H, m), 7.60 (1H, dd, J=7.7, 7.7 Hz), 7.71–7.80 (2H, m), 7.88–7.97 (2H, m), 8.16 (1H, dd, J=1.6, 1.6 Hz), 13.12 (1H, s)
(−) APCI MASS (m/z): 215 [M−H]$^{-1}$
(4) 3-(3-Trifluoromethylphenyl)benzoic acid
mp: 138°–140° C.
IR (Nujol): 1680, 1340, 1120 cm$^{-1}$
NMR (DMSO-d$_6$, δ): 7.59 (1H, dd, J=7.7 Hz, 7.7 Hz), 7.67–7.79 (2H, m), 7.90–8.04 (4H, m), 8.28 (1H, s)
(−) APCI MASS (m/z): 264 [M−2H]$^-$
(5) 3-(3-Chlorophenyl)benzoic acid
mp: 178°–180° C.
IR (Nujol): 1680, 1310, 1250 cm$^{-1}$
NMR (DMSO-d$_6$, δ): 7.48–7.71 (4H, m), 7.77 (1H, dd, J=1.9 Hz, 1.9 Hz), 7.94–8.01 (2H, m), 8.19 (1H, dd, J=1.8 Hz, 1.8 Hz)
(−) APCI MASS (m/z): 231 [M−H]$^-$
(6) 3-(Furan-3-yl)benzoic acid
mp: 145°–147° C.
IR (Nu jol): 1680, 1580, 1370, 1290 cm$^{-1}$
NMR (DMSO-d$_6$, δ): 7.03 (1H, dd, J=1.6 Hz, 1.0 Hz), 7.53 (1H, dd, J=7.7 Hz, 7.7 Hz), 7.79 (1H, dd, J=1.6 Hz, 1.6 Hz), 7.83–7.91 (2H, m), 8.16 (1H, dd, J=1.6 Hz, 1.0 Hz), 8.31 (1H, s), 13.07 (1H, s)
(+) APCI MASS (m/z): 189 [M+H]$^+$
(7) 3-(2-Fluorophenyl)benzoic acid
mp: 144°–146° C.
IR (Nujol): 1680, 1250, 745 cm$^{-1}$
NMR (DMSO-d$_6$, δ): 7.29–7.67 (5H, m), 7.79–7.84 (1H, m), 7.96–8.02 (1H, m), 8.10–8.12 (1H, m)
(8) 3-(3-Methylphenyl)benzoic acid
mp: 123°–125° C.
IR (Nujol): 1680, 1305, 1280, 750 cm$^{-1}$
NMR (DMSO-d$_6$, δ): 2.40 (3H, s), 7.20–7.65 (5H, m), 7.88–7.97 (2H, m), 8.16–8.19 (1H, m), 13.09 (1H, s)
Preparation 84
The following compounds were obtained according to a similar manner to that of Preparation 26.
(1) Methyl 3-(pyridin-2-yl)benzoate
IR (Film): 1720, 1580 cm$^{-1}$
NMR (DMSO-d$_6$, δ): 3.91 (3H, s), 7.41–7.47 (1H, m), 7.66 (1H, dd, J=7.6 Hz, 7.6 Hz), 7.91–8.03 (1H, m), 8.00–8.10 (2H, m), 8.30–8.40 (1H, m), 8.69–8.76 (2H, m)
(+) APCI MASS (m/z): 214 [M+H]$^+$
(2) Methyl 3-(pyridin-3-yl)benzoate
IR (Film): 1720, 1580 cm$^{-1}$
NMR (DMSO-d$_6$, δ): 3.91 (3H, s), 7.47–7.58 (1H, m), 7.68 (1H, dd, J=7.7 Hz, 7.7 Hz), 7.97–8.07 (2H, m), 8.08–8.18 (1H, m), 8.23 (1H, dd, J=1.6 Hz, 1.6 Hz), 8.63 (1H, dd, J=1.6 Hz, 4.8 Hz), 8.93 (1H, dd, J=0.7 Hz, 2.4 Hz)
(+) APCI MASS (m/z): 214 [M+H]$^+$
(3) Dimethyl 5-[2-(4,4-dimethyl-4,5-dihydrooxazol-2-yl)phenyl]isophthalate
mp: 89°–90° C.
IR (Nujol): 1725, 1660, 1235 cm$^{-1}$
NMR (DMSO-d$_6$, δ): 1.15 (6H, s), 3.81 (2H, s), 3.91 (6H, s), 7.49–7.76 (4H, m), 8.14 (2H, s), 8.46 (1H, s)
(+) APCI MASS (m/z): 368 [M+H]$^+$
(4) 4,4-Dimethyl-2-[3-(2-nitrophenyl)phenyl]-4,5-dihydrooxazole
IR (Neat): 2960, 1730, 1640, 1520 cm$^{-1}$
NMR (DMSO-d$_6$, δ) 1.29 (6H, s), 4.13 (2H, s), 7.51–7.72 (4H, m), 7.76–7.80 (2H, m), 7.91 (1H, ddd, J=7.1 Hz, 1.7 Hz, 1.7 Hz), 8.04 (1H, dd, J=7.9 Hz, 1.3 Hz)
(+) APCI MASS (m/z): 297 [M+H]$^+$
(5) Methyl 3-[3-(4,4-dimethyl-4,5-dihydrooxazol-2-yl)-phenyl]benzoate
mp: 53°–55° C.
IR (Neat): 2950, 1720, 1650, 1440, 1300 cm$^{-1}$
NMR (DMSO-d$_6$, δ): 1.32 (6H, s), 3.91 (3H, s), 4.15 (2H, s), 7.61 (1H, dd, J=7.7 Hz, 7.7 Hz), 7.66 (1H, dd, J=7.7 Hz, 7.7 Hz), 7.86–7.92 (2H, m), 7.97–8.03 (2H, m), 8.11 (1H, dd, J=1.6 Hz, 1.6 Hz), 8.19 (1H, dd, J=1.7 Hz, 1.7 Hz)
(+) APCI MASS (m/z): 310 [M+H]$^+$
Elemental Analysis Calcd. for $C_{19}H_{19}NO_3$ C 73.77, H 6.19, N 4.53 Found C 73.89, H 6.40, N 4.34
Preparation 85
The following compound was obtained according to a similar manner to that of Preparation 28.
(1) Dimethyl 5-(2-cyanophenyl)isophthalate
mp: 185°–187° C.
IR (Nujol): 2225, 1720, 1240, 990, 755 cm$^{-1}$
NMR (DMSO-d$_6$, δ) 3.94 (6H, s), 7.63–7.90 (4H, m), 8.01 (1H, d, J=7.8 Hz), 8.37 (2H, H), 8.58 (1H, s)
(+) APCI MASS (m/z): 296 [M+H]$^+$
(2) Methyl 3-(3-cyanophenyl)benzoate
mp: 82°–84° C.
IR (Nujol): 2230, 1720, 1250 cm$^{-1}$
NMR (DMSO-d$_6$, δ) :3.90 (3H, s), 7.67 (1H, dd, J=7.6 Hz, 7.6 Hz), 7.70 (1H, dd, J=7.6 Hz, 7.6 Hz), 7.89 (1H, ddd, J=7.6 Hz, 1.4 Hz, 1.4 Hz), 7.98–8.10 (3H, m), 8.22–8.26 (2H, m)

(+) APCI MASS (m/z): 238 [M+H]+

Elemental Analysis Calcd. for $C_{15}H_{11}NO_2$: C 75.94, H 4.67, N 5.90 Found C 75.91, H 4.74, N 5.89

Preparation 86

The following compound was obtained according to a similar manner to that of Preparation 30.

Methyl 3-dimethylcarbamoyl-5-(pyrrol-1-yl)benzoate

IR (Film): 3450, 3130, 2950, 1720, 1630 cm$^{-1}$

NMR (DMSO-d$_6$, δ) 2.93 (3H, s), 3.02 (3H, s), 3.91 (3H, s), 6.3–6.4 (2H, m), 7.5–7.6 (2H, m), 7.7–7.8 (1H, m), 7.9–8.0 (1H, m), 8.1–8.2 (1H, m)

(+) APCI MASS (m/z): 273 [M+H]+

Preparation 87

Methyl 3-formyl-5-(pyrrol-1-yl)benzoate (2.0 g) was added to a mixture of hydroxylamine hydrochloride (0.61 g) and 28% methanolic sodium methoxide (1.8 ml) in methanol (20 ml) and the whole was stirred for 22 hours at ambient temperature. The reaction mixture was poured into a mixture of ethyl acetate and water. The organic layer was successively washed with brine and dried over magnesium sulfate. The solvent was evaporated in vacuo and the residue was purified by column chromatography on silica gel eluting with a mixture of chloroform and ethyl acetate (20:1). The eluted fractions containing the desired product were collected and evaporated in vacuo to give methyl 3-hydroxyiminomethyl-5-(pyrrol-1-yl)benzoate (1.69 g).

mp: 154°–155° C.

IR (Nujol): 3250, 1720, 1600 cm$^{-1}$

NMR (DMSO-d$_6$, δ): 3.91 (3H, s), 6.3–6.4 (2H, m), 7.4–7.5 (2H, m), 8.0–8.3 (4H, m), 11.59 (1H, s)

(+) APCI MASS (m/z): 245 [M+H]+

Elemental Analysis Calcd. for $C_{13}H_{12}N_2O_3$: C 63.93, H 4.95, N 11.47 Found: C 64.02, H 5.15, N 11.46

Preparation 88

The following compound was obtained according to a similar manner to that of Preparation 52.

Methyl 3-hydroxymethyl-5-phenylbenzoate mp: 89°–90° C.

IR (Nujol): 3475, 1720, 1250, 760 cm$^{-1}$

NMR (DMSO-d$_6$, δ): 3.89 (3H, s), 4.65 (2H, d, J=5.8 Hz), 5.43 (1H, t, J=5.8 Hz), 7.37–7.55 (3H, m), 7.67–7.72 (2H, m), 7.87 (1H, s), 7.95 (1H, s), 8.05 (1H, s)

(+) APCI MASS (m/z): 243 [M+H]+

Preparation 89

The following compound was obtained according to a similar manner to that of Preparation 56.

3-Methoxycarbonyl-5-phenylbenzoic acid mp: 170°–172° C.

IR (Nujol): 1720, 1685, 750 cm$^{-1}$

NMR (DMSO-d$_6$, δ) 3.93 (3H, s), 7.4–7.6 (3H, m), 7.7–7.8 (2H, m), 8.38–8.41 (2H, m), 8.47 (1H, s), 13.44 (1H, s)

(+) APCI MASS (m/z): 257 [M+H]+

Preparation 90

The mixture of 3-hydrazinobenzoic acid (5.0 g) and ethyl 2-ethoxymethylene-2-cyanoacetate (5.6 g) in ethanol (50 ml) was heated under reflux for 2 hours under stirring, and then the mixture was evaporated in vacuo. To the residue was added a mixture of ethyl acetate and water, and the mixture was adjusted to pH 8 with 20% aqueous potassium carbonate solution. The separated aqueous layer was adjusted to pH 4 with 6N-hydrochloric acid and extracted with ethyl acetate. The extract layer was washed with water, dried over magnesium sulfate and evaporated in vacuo. The residue was triturated with a solution of ethyl acetate and diisopropyl ether and the precipitate was collected by filtration to give 3-(5-amino-4-ethoxycarbonylpyrazol-1-yl)benzoic acid (6.0 g).

mp: 172°–174° C.

IR (Nujol): 3360, 3250, 1688, 1605 cm$^{-1}$

NMR (DMSO-d$_6$, δ): 1.28 (3H, t, J=7.1 Hz), 4.23 (2H, q, J=7.1 Hz), 6.46 (2H, s), 7.67 (1H, dd, J=7.8 Hz, 7.8 Hz), 7.75 (1H, s), 7.81 (1H, d, J=7.8 Hz), 7.96 (1H, d, J=7.8 Hz), 8.08 (1H, s), 13.27 (1H, s)

Preparation 91

The mixture of 3-(5-amino-4-ethoxycarbonylpyrazol-1-yl)benzoic acid (5.9 g) and sodium hydroxide (2.1 g) in water (15 ml) was stirred for 2 hours at 80° C. To the reaction mixture was added water and the mixture was adjusted to pH 3.5 with 6N-hydrochloric acid. The isolated precipitate was collected by filtration washed with water and dried to give 3-(5-amino-4-carboxypyrazol-1-yl)benzoic acid (5.1 g).

mp: 194°–196° C.

IR (Nujol): 3540, 3420, 3200, 1678 cm$^{-1}$

NMR (DMSO-d$_6$, δ): 6.41 (2H, s), 7.66 (1H, t, J=7.8 Hz, 7.8 Hz), 7.72 (1H, s), 7.82 (1H, d, J=7.8 Hz), 7.95 (1H, d, J=7.8 Hz), 8.08 (1H, s), 12.88 (1H, s)

Preparation 92

The mixture of 3-(5-amino-4-carboxypyrazol-1-yl)benzoic acid (19.4 g) in diglyme (200 ml) was heated under reflux for 6 hours. To the mixture was added a mixture of ethyl acetate and water, and adjusted to pH 9 with 20% aqueous potassium carbonate solution. The separated aqueous layer was adjusted to pH 3.5 with 6N-hydrochloric acid and the mixture was extracted with a solution of ethyl acetate and tetrahydrofuran. The extract layer was washed with brine, dried over magnesium sulfate and evaporated in vacuo to give 3-(5-aminopyrazol-1-yl)benzoic acid (7.59 g).

mp: 155°–156° C.

IR (Nujol): 3300, 3210, 1700, 1635 cm$^{-1}$

NMR (DMSO-d$_6$, δ): 5.43 (2H, s), 5.51 (1H, d, J=1.8 Hz), 7.33 (1H, d, J=1.8 Hz), 7.60 (1H, dd, J=7.8 Hz, 7.8 Hz), 7.82–7.91 (2H, m), 8.15–8.21 (1H, m), 13.15 (1H, s)

(+) APCI MASS (m/z): 204 [M+H]+

Preparation 93

Potassium tert-butoxide (6.4 g) was added to a solution of dimethyl isophthalate (10.0 g) in acetonitrile (90 ml) at ambient temperature and the mixture was stirred for 1 hour at 60°–64° C. The reaction mixture was added to a solution of conc. hydrochloric acid (4.7 ml) in water (150 ml) and extracted with ethyl acetate. The extract layer was washed with water and dried over magnesium sulfate. Evaporation of the solvent gave a residue, which was purified by column chromatography on silica gel eluting with chloroform. The eluted fractions containing the desired product were collected and evaporated in vacuo to give methyl 3-(cyanoacetyl)benzoate (4.72 g).

mp: 48°–52° C.

IR (Nujol): 2250, 1723, 1693, 1600 cm$^{-1}$

NMR (DMSO-d$_6$, δ): 3.91 (3H, s), 4.85 (2H, s), 7.73 (1H, dd, J=7.6 Hz, 7.6 Hz), 8.10–8.32 (2H, m), 8.43 (1H, s)

Preparation 94

To the stirring mixture of methyl 3-(cyanoacetyl)benzoate (2.0 g), triethylamine (1.4 ml), triethylamine hydrochloride (1.4 g) and 40% aqueous methylamine (0.93 ml) was added chloroacetone (0.86 ml) at ambient temperature and the mixture was stirred for 2 hours at the same temperature. To the reaction mixture was added ethyl acetate and the mixture was washed with water. The organic layer was dried over magnesium sulfate and evaporated in vacuo. The residue was recrystallized from ethanol to give methyl 3-(3-cyano-1,5-dimethylpyrrol-2-yl)benzoate (1.6 g).

mp: 125°–126° C.

IR (Nujol): 2220, 1720 cm$^{-1}$

NMR (DMSO-$d_6$, δ): 2.26 (3H, s), 3.47 (3H, s), 3.89 (3H, s), 6.37 (1, s), 7.64–7.82 (2H, m), 8.00 (1H, s), 8.02–8.10 (1H, m)

(+) APCI MASS (m/z): 255 [M+H]$^+$

Preparation 95

To a solution of dimethyl 5-hydroxyisophthalate (5.0 g), 4-dimethylaminopyridine (0.45 g), and 2,6-lutidine in dichloromethane (60 ml) at −30° C. was added dropwise bis(trifluoromethanesulfonic)anhydride (4.8 ml). After stirring for 20 minutes at −30° C., the cooling bath was removed and the reaction mixture was stirred for 3 hours at ambient temperature. Saturated aqueous solution of ammonium chloride was added to the reaction mixture, the separated aqueous layer was extracted twice with methylene chloride. The combined extracts were dried over magnesium sulfate and evaporated in vacuo. The residue was dissolved in ethyl acetate (100 ml) and washed successively with water, 10% hydrochloric acid, saturated sodium bicarbonate solution, brine and dried over magnesium sulfate. The solvent was evaporated in vacuo and the residue was crystallized from n-hexane and diethyl ether to afford dimethyl 5-(trifluoromethylsulfonyloxy)isophthalate (5.59 g).

mp: 73°–74° C.

IR (Nujol): 1725, 1135, 990 cm$^{-1}$

NMR (DMSO-$d_6$, δ): 3.94 (6H, s), 8.27 (2H, s), 8.52 (1H, s)

(+) APCI MASS (m/z): 343 [M+H]$^+$

Preparation 96

The following compound was obtained according to a similar manner to that of Preparation 95.

Methyl 5-benzyloxy-3-(trifluoromethylsulfonyloxy)benzoate

IR (Neat): 1720, 1580, 1300, 1220, 1130 cm$^{-1}$

NMR (DMSO-$d_6$, δ): 3.89 (3H, s), 5.26 (2H, s), 7.31–7.57 (7H, m), 7.64–7.66 (1H, m)

(+) APCI MASS (m/z): 391 [M+H]$^+$

Preparation 97

A mixture of dimethyl 5-(trifluoromethylsulfonyloxy)isophthalate (2.3 g), dihydroxy-phenylborane (1.23 g) and triethylamine (2.0 4 g) in N,N-dimethylformamide (30 ml) was heated at 100° C. and stirred for 3 hours under nitrogen. After evaporating the solvent, the residue was dissolved in a mixture of dichlomethane (100 ml) and water. The organic layer was successively washed with aqueous 10% sodium carbonate solution and brine, dried over magnesium sulfate and evaporated in vacuo. The residue was crystallized from hexane to afford dimethyl 5-phenylisophthalate (1.07 g).

mp: 91°–92° C.

IR (Nujol): 1730, 1235, 745 cm$^{-1}$

NMR (DMSO-$d_6$, δ): 3.93 (6H, s), 7.4–7.6 (3H, m), 7.7–7.8 (2H, m), 8.39 (2H, s), 8.44 (1H, s)

(+) APCI MASS (m/z): 271 [M+H]$^+$

Preparation 98

The following compound was obtained according to a similar manner to that of Preparation 97.

Methyl 3-benzyloxy-5-phenylbenzoate mp: 83°–84° C.

IR (Nujol): 1720, 1590, 1340, 1240 cm$^{-1}$

NMR (DMSO-$d_6$, δ): 3.88 (3H, s), 5.27 (2H, s), 7.32–7.60 (10H, m), 7.69 (1H, dd, J=1.4 Hz, 1.4 Hz), 7.73 (1H, dd, J=1.4 Hz, 1.4 Hz), 7.80 (1H, dd, J=1.4 Hz, 1.4 Hz)

(+) APCI MASS (m/z): 319 [M+H]$^+$

Preparation 99

10% Palladium on carbon (0.4 g) was added to a solution of methyl 3-(3-nitrophenyl)benzoate (2.0 g) in methanol (30 ml) and the mixture was subjected to catalytic hydrogenation at ambient temperature under atmospheric pressure. After one hour, the catalyst was removed by filtration and the filtrate was evaporated in vacuo. The residue was crystallized from diethyl ether to afford methyl 3-(3-aminophenyl)benzoate (1.45 g).

mp: 63°–65° C.

IR (Nujol): 3400, 1705, 1220, 755 cm$^{-1}$

NMR (DMSO-$d_6$, δ): 3.89 (3H, s), 6.60–6.66 (1H, m), 6.80–6.95 (2H, m), 7.15 (1H, dd, J=7.8 Hz, 7.8 Hz), 7.59 (1H, dd, J=7.8, 7.8 Hz), 7.80–7.95 (2H, m), 8.10–8.13 (1H, m)

Preparation 100

4,4-Dimethyl-2-[3-(2-nitrophenyl)phenyl]4,5-dihydrooxazole (1.7 g) was heated to reflux for 19 hours in 95% methanolic sulfuric acid (28.7 ml) (prepared by mixing methanol (15 ml), concentrated sulfuric acid (1.15 ml), and water (1.44 ml) and bringing the total volume to 28.7 ml with additional methanol). After cooling, the solution was concentrated to ca. 7 ml and poured into ether (60 ml). The ethereal solution was washed with aqueous potassium carbonate solution and brine,then dried over magnesium sulfate and concentrated in vacuo to yield methyl 3-(2-nitrophenyl)benzoate as a yellow solid.

mp: 88°–90° C.

IR (Nujol): 1720, 1520 cm$^{-1}$

NMR (DMSO-$d_6$, δ): 3.88 (3H, s), 7.58–7.82 (5H, m), 7.89 (1H, S), 8.00–8.04 (2H, m)

(+) APCI MASS (m/z): 258 [M+H]$^+$

Preparation 101

The following compound was obtained according to a similar manner to that of Preparation 100.

Methyl 3-[3-(methoxycarbonyl)phenyl]benzoate mp: 99°–101° C.

IR (Nujol): 1730, 1320, 1260, 1240 cm$^{-1}$

NMR (DMSO-$d_6$, δ): 3.91 (6H, s), 7.66 (2H, dd, J=7.8 Hz, 7.8 Hz), 8.01 (4H, dd, J=7.8 Hz, 1.8 Hz), 8.20 (2H, dd, J=1.6 Hz, 1.6 Hz)

(+) APCI MASS (m/z): 271 [M+H]$^+$

Preparation 102

To a solution of methyl 3-benzyloxy-5-phenylbenzoate (10 g) in acetic acid (300 ml) was added 10% palladium on carbon (1 g), and the mixture was subjected to catalytic hydrogenation at 80° C. under atmospheric pressure. The catalyst was removed by filtration and the filtrate was evaporated in vacuo. To the residue were added ethyl acetate and water, and adjusted to pH 5 with potassium carbonate. The separated organic layer was washed with brine, dried over magnesium sulfate and evaporated in vacuo to give methyl 3-hydroxy-5-phenylbenzoate.

mp: 108°–110° C.

IR (Nujol): 3400, 1710, 1590, 1350, 1250 cm$^{-1}$

NMR (DMSO-$d_6$, δ): 3.87 (3H, s), 7.29 (1H, dd, J=1.7 Hz, 1.7 Hz), 7.36–7.53 (4H, m), 7.62–7.67 (3H, m), 10.05 (1H, s)

(+) APCI MASS (m/z): 229 [M+H]$^+$

Preparation 103

A mixture of methyl 3-hydroxymethyl-5-(pyrrol-1-yl)benzoate (20.0 g) and manganese dioxide (100.0 g) in dichloromethane (0.5 l) was stirred for 22 hours at room temperature. The manganese dioxide was filtered off and the filtrate was evaporated in vacuo. The residue was pulverized from diisopropyl ether and petroleum ether to give methyl 3-formyl-5-(pyrrol-1-yl)benzoate (17.6 g).

mp: 85°–86° C.

IR (Nujol): 1710, 1600 cm$^{-1}$

NMR (DMSO-$d_6$, δ): 3.94 (3H, s), 6.3–6.4 (2H, m), 7.5–7.6 (2H, m), 8.2–8.4 (3H, m), 10.12 (1H, s)

(+) APCI MASS (m/z): 230 [M+H]$^+$

Preparation 104

To a mixture of methyl 3-amino-5-(pyrrol-1-yl)benzoate (1.0 g) and pyridine (0.41 ml) in dichloromethane (20 ml) was added bromoacetyl bromide (0.44 ml) under ice cooling. After stirring for 6 hours at room temperature, the reaction mixture was poured into the mixture of ethyl acetate and ice-water. The organic layer was successively washed with brine and dried over magnesium sulfate. The solvent was evaporated in vacuo and the residue was pulverized from diethyl ether to give methyl 3-bromoacetylamino-5-(pyrrol-1-yl)benzoate (1.51 g).

mp: 154°–157° C.

IR (Nujol): 3250, 1715, 1650, 1600 cm$^{-1}$

NMR (DMSO-d$_6$, δ): 3.90 (3H, s), 4.09 (2H, s), 6.3–6.4 (2H, m), 7.3–7.4 (2H, m), 7.7–7.8 (1H, m), 8.0–8.1 (2H, m), 10.78 (1H, s)

(+) APCI MASS (m/z): 337, 339 [M+H]$^+$

Preparation 105

A mixture of methyl 3-bromoacetylamino-5-(pyrrol-1-yl)benzoate (0.5 g) and morpholine (0.28 ml) in dichloromethane (5 ml) and tetrahydrofuran (7 ml) was stirred for 17 hours at room temperature. The reaction mixture was poured into the mixture of ethyl acetate and water. The organic layer was successively washed with brine and dried over magnesium sulfate. The solvent was evaporated in vacuo and the residue was purified by column chromatography on silica gel eluting with chloroform. The eluted fractions containing the desired product were collected and evaporated in vacuo to give methyl 3-morpholinoacetylamino-5-(pyrrol-1-yl)benzoate (0.48 g).

mp: 108°–109° C.

IR (Nujol): 1725, 1690, 1605 cm$^{-1}$

NMR (DMSO-d$_6$, δ): 2.4–2.6 (4H, m), 3.18 (2H, s), 3.6–3.8 (4H, m), 3.89 (3H, s), 6.3–6.4 (2H, m), 7.2–7.3 (2H, m), 7.7–7.8 (1H, m), 8.1–8.3 (2H, m), 10.08 (1H, s)

(+) APCI MASS (m/z): 344 [M+H]$^+$

Preparation 106

The following compound was obtained according to a similar manner to that of Preparation 105.

Methyl 3-diethylaminoacetylamino-5-(pyrrol-1-yl)benzoate mp: 103°–105° C.

IR (Nujol): 3250, 2960, 1720, 1685, 1600 cm$^{-1}$

NMR (DMSO-d$_6$, δ): 1.03 (6H, t, J=7.1 Hz), 2.62 (4H, q, J=7.1 Hz), 3.19 (2H, s), 3.89 (3H, s), 6.2–6.4 (2H, m), 7.3–7.4 (2H, m), 7.73 (1H, s), 8.13 (1H, s), 8.31 (1H, s), 10.01 (1H, s)

(+) APCI MASS (m/z): 330 [M+H]$^+$

Preparation 107

To a mixture of methyl 3-amino-5-(pyrrol-1-yl)benzoate (2.0 g) and triethylamine (1.4 ml) in dichloromethane (130 ml) was added bis(trifluoromethanesulfonic)anhydride (1.7 ml) at −78° C. The reaction mixture was allowed to warm to room temperature and poured into the mixture of ethyl acetate and water. The organic layer was successively washed with brine and dried over magnesium sulfate. The solvent was evaporated in vacuo and the residue was pulverized from petroleum ether to give methyl 3-trifluoromethylsulfonylamino-5-(pyrrol-1-yl)benzoate (3.17 g).

mp: 147°–148° C.

IR (Nujol): 3150, 1705, 1600 cm$^{-1}$

NMR (DMSO-d$_6$, δ): 3.91 (3H, s), 6.3–6.4 (2H, m), 7.4–7.5 (2H, m), 7.6–8.0 (3H, m)

(+) APCI MASS (m/z): 349 [M+H]$^+$

Preparation 108

The following compound was obtained according to a similar manner to that of Preparation 107.

Methyl 3-(3-trifluoromethylsulfonylaminophenyl)benzoate mp: 103°–104° C.

IR (Nujol): 3200, 1705, 960, 750 cm$^{-1}$

NMR (DMSO-d$_6$, δ): 3.90 (3H, s), 7.31–7.36 (1H, m), 7.50–7.72 (4H, m), 7.9–8.05 (2H, m), 8.14–8.17 (1H, m)

(+) APCI MASS (m/z): 360 [M+H]$^+$

Preparation 109

A mixture of methyl 3-formyl-5-(pyrrol-1-yl)benzoate (3.0 g), malonic acid (2.73 g), piperidine (0.3 ml) and pyridine (30 ml) was stirred for 1 hour at 80° C. After being cooled to room temperature, the reaction mixture was poured into water. The solution was acidified to pH 1 and extracted with ethyl acetate. The extract was washed with water and brine and dried over magnesium sulfate. The solvent was evaporated in vacuo and the residue was purified by column chromatography on silica gel eluting with the mixture of chloroform and methanol (15:1). The eluted fractions containing the desired product were collected and evaporated in vacuo to give methyl 3-((E)-2-carboxyethenyl)-5-(pyrrol-1-yl)benzoate (2.43 g).

mp: 210°–211° C.

IR (Nujol): 1720, 1630, 1590 cm$^{-1}$

NMR (DMSO-d$_6$, δ): 3.90 (3H, s), 6.3–6.4 (2H, m), 6.81 (1H, d, J=16.0 Hz), 7.5–7.6 (2H, m), 7.65 (1H, d, J=16.0 Hz), 7.9–8.3 (3H, m)

(+) APCI MASS (m/z): 272 [M+H]$^+$

Preparation 110

To a mixture of methyl 3-((E)-2-carboxyethenyl)-5-(pyrrol-1-yl)benzoate (1.9 g) and nickel(II) chloride in methanol (40 ml) was added portionwise sodium borohydride (1.24 g). After stirring for 7 hours at room temperature, the reaction mixture was filtered and poured into water, followed by acidification of the solution to pH 2. The resulting precipitate was collected by filtration and washed with water to give methyl 3-(2-carboxyethyl)-5-(pyrrol-1-yl)benzoate (1.72 g).

mp: 129°–130° C.

IR (Nujol): 1720, 1700, 1600 cm$^{-1}$

NMR (DMSO-d$_6$, δ): 2.64 (2H, t, J=7.4 Hz), 2.95 (2H, t, J=7.4 Hz), 3.88 (3H, s), 6.3–6.4 (2H, m), 7.4–7.5 (2H, m), 7.7–7.9 (3H, m), 12.19 (1H, br s)

(+) APCI MASS (m/z): 274 [M+H]$^+$

Elemental Analysis Calcd. for $C_{15}H_{15}NO_4$: C 65.93, H 5.53, N 5.13 Found: C 65.88, H 5.68, N 5.05

Preparation 111

The mixture of methyl 3-(2-formylpyrrol-1-yl)benzoate (3.0 g), malonic acid (2.7 g), pyridine (30 ml) and piperidine (0.3 ml) was stirred for 3 hours at 90°–100° C. The reaction mixture was poured into water, and the mixture was adjusted to pH 1 with 6N-hydrochloric acid. The mixture was extracted with a mixture of ethyl acetate and tetrahydrofuran. The extract layer was washed with brine, dried over magnesium sulfate and evaporated in vacuo. The residue was recrystallized from ethanol to give methyl 3-[2-((E)-2-carboxyethenyl)pyrrol-1-yl)benzoate.

mp: 201°–203° C.

IR (Nujol): 1728, 1673, 1610 cm$^{-1}$

NMR (DMSO-d$_6$, δ): 3.89 (3H, s), 6.12 (1H, d, J=15.7 Hz), 6.35–6.39 (1H, m), 7.00–7.04 (1H, m), 7.17 (1H, d, J=15.7 Hz), 7.29 (1H, s), 7.60–7.80 (2H, m), 7.84 (1H, s), 8.04–8.11 (1H, m), 12.11 (1H, s)

Preparation 112

A mixture of methyl 3-(2-carboxyethyl)-5-(pyrrol-1-yl)benzoate (1.5 g), diphenylphosphoryl azide (1.25 ml) and triethylamine (0.8 ml) in tert-butyl alcohol (20 ml) was refluxed for 7 hours. After being cooled to room temperature, the reaction mixture was poured into a mixture of ethyl acetate and water. The organic layer was successively washed with 1N-hydrochloric acid, water and brine and dried over magnesium sulfate. The solvent was evaporated in vacuo and the residue was purified by column chromatography on silica gel eluting with chloroform. The eluted fractions containing the desired product were collected and evaporated in vacuo to give methyl 3-(2-tert-butoxycarbonylaminoethyl-5-(pyrrol-1-yl)benzoate (0.89 g).

mp: 82°–83° C.

IR (Nujol): 3350, 1725, 1685, 1600 cm$^{-1}$

NMR (DMSO-d$_6$, δ) 1.32 (9H, s), 2.7–2.9 (2H, m), 3.1–3.3 (2H, m), 3.88 (3H, s), 6.2–6.3 (2H, m), 6.8–7.0 (1H, m), 7.4–7.5 (2H, m), 7.6–7.9 (3H, m)

(+) APCI MASS (m/z): 345 [M+H]$^+$

Preparation 113

A mixture of methyl 3-formyl-5-(pyrrol-1-yl)benzoate (1.66 g), 2-aminoethanol (0.88 ml) and molecular sieves 4A (1.7 g) in methanol (40 ml) was stirred for 6 hours at room temperature. Then, to the reaction mixture was added sodium borohydride (0.55 g). After stirring for 3 hours at room temperature, the reaction mixture was poured into saturated aqueous sodium hydrogencarbonate solution and filtered. The filtrate was evaporated in vacuo and the residue was purified by column chromatography on silica gel eluting with a mixture of chloroform and methanol (20:1). The eluted fractions containing the desired product were collected and evaporated in vacuo to give methyl 3-(2-hydroxyethylaminomethyl)-5-(pyrrol-1-yl)benzoate (0.80 g).

mp: 85°–87° C.

IR (Nujol): 3150, 1715, 1600 cm$^{-1}$

NMR (DMSO-d$_6$, δ): 2.32 (1H, br s), 2.58 (2H, t, J=5.8 Hz), 3.4–3.6 (2H, m), 3.82 (2H, s), 3.89 (3H, s), 4.4–4.6 (1H, m), 6.2–6.4 (2H, m), 7.4–7.5 (2H, m), 7.8–8.0 (3H, m)

(+) APCI MASS (m/z): 275 [M+H]$^+$

Preparation 114

The following compound was obtained according to a similar manner to that of Preparation 113.

Methyl 3-dimethylaminomethyl-5-(pyrrol-1-yl)benzoate

IR (Nujol): 2590, 2565, 2555, 1720, 1600 cm$^{-1}$

NMR (DMSO-d$_6$, δ): 2.19 (6H, s), 3.51 (2H, s), 3.89 (3H, s), 6.2–6.4 (2H, m), 7.4–7.5 (2H, m), 7.7–8.0 (3H, m)

(+) APCI MASS (m/z): 259 [M+H]$^+$

Preparation 115

To a solution of methyl 3-nitro-5-(pyrrol-1-yl)benzoate (35.8 g) in concentrated hydrochloric acid (79 ml) and methanol (73 ml) was added portionwise iron (48.6 g). After stirring for 3.5 hours at room temperature, the reaction mixture was poured into a mixture of ethyl acetate and water and filtered. The organic layer was successively washed with water and brine and dried over magnesium sulfate. The solvent was evaporated in vacuo and the residue was pulverized from petroleum ether and diisopropyl ether to give methyl 3-amino-5-(pyrrol-1-yl)benzoate (22.7 g).

mp: 116°–118° C.

IR (Nujol): 3430, 3330, 1710, 1620, 1600 cm$^{-1}$

NMR (DMSO-d$_6$, δ): 3.84 (3H, s), 5.65 (2H, br s), 6.2–6.3 (2H, m), 6.9–7.3 (5H, m)

(+) APCI MASS (m/z): 217 [M+H]$^+$

Preparation 116

To a mixture of methyl 3-(2-hydroxyethylaminomethyl)-5-(pyrrol-1-yl)benzoate (0.8 g) and triethylamine (0.48 ml) was added benzyl chloroformate (0.46 ml) under ice cooling. After stirring for 2 hours under ice cooling, the reaction mixture was poured into the mixture of ethyl acetate and water. The organic layer was washed with brine and dried over magnesium sulfate. The solvent was evaporated in vacuo and the residue was purified by column chromatography on silica gel eluting with the mixture of chloroform and methanol (15:1). The eluted fractions containing the desired product were collected and evaporated in vacuo to give methyl 3-[N-benzyloxycarbonyl-N-(2-hydroxyethyl)aminomethyl]-5-(pyrrol-1-yl)benzoate (1.11 g).

IR (Film): 3420, 2950, 1715, 1695, 1600 cm$^{-1}$

NMR (DMSO-d$_6$, δ): 3.3–3.6 (4H, m), 3.88 (3H, s), 4.63 (2H, s), 4.79 (1H, t, J=5.2 Hz), 5.1–5.2 (2H, m), 6.3–6.4 (2H, m), 7.1–7.5 (7H, m), 7.6–7.8 (2H, m), 7.93 (1H, s)

(+) APCI MASS (m/z): 409 [M+H]$^+$

Preparation 117

The following compound was obtained according to a similar manner to that of Preparation 74.

Methyl 2-acetoxy-3-(pyrrol-1-yl)benzoate

IR (Film): 1765, 1725, 1585 cm$^{-1}$

NMR (DMSO-d$_6$, δ): 2.17 (3H, s), 3.84 (3H, s), 6.23–6.29 (2H, m), 6.96–7.02 (2H, m), 7.52 (1H, dd, J=7.9 Hz, 7.9 Hz), 7.76 (1H, dd, J=1.6 Hz, 7.9 Hz), 7.92 (1H, dd, J=1.6 Hz, 7.9 Hz)

Preparation 118

The following compound was obtained according to a similar manner to that of Preparation 75.

Methyl 3-(2-formylpyrrol-1-yl)-2-hydroxybenzoate mp: 79°–82° C.

IR (Nujol): 1660 cm$^{-1}$

NMR (DMSO-d$_6$, δ): 3.94 (3H, s), 6.42–6.49 (1H, m), 7.07 (1H, dd, J=7.9 Hz, 7.9 Hz), 7.14–7.21 (1H, m), 7.28–7.33 (1H, m), 7.61 (1H, dd, J=1.7 Hz, 7.9 Hz), 7.88–7.96 (1H, m), 9.43 (1H, s), 10.89 (1H, s)

Preparation 119

The following compound was obtained according to a similar manner to that of Preparation 76.

Methyl 2-hydroxy-3-(2-hydroxymethylpyrrol-1-yl)benzoate

IR (Film): 1670 cm$^{-1}$

NMR (DMSO-d$_6$, δ): 3.94 (3H, s), 4.23 (2H, d, J=5.1 Hz), 4.71 (1H, t, J=5.1 Hz), 6.06–6.16 (2H, m), 6.73–6.79 (1H, m), 7.05 (1H, t, J=7.9 Hz, 7.9 Hz), 7.61 (1H, dd, J=1.7 Hz, 7.9 Hz), 7.88 (1H, dd, J=1.7 Hz, 7.9 Hz), 10.90 (1H, s)

Preparation 120

The following compound was obtained according to a similar manner to that of Preparation 77.

6-Methoxycarbonyl-4H-pyrrolo[2,1-c][1,4]benzoxazine

IR (Film): 1725 cm$^{-1}$

NMR (DMSO-d$_6$, δ): 3.82 (3H, s), 5.23 (2H, s), 6.07–6.13 (1H, m), 6.28–6.36 (1H, m), 7.14 (1H, dd, J=7.9 Hz, 7.9 Hz), 7.42–7.66 (2H, m), 7.88 (1H, dd, J=1.6 Hz, 7.9 Hz)

(+) APCI MASS (m/z): 230 [M+H]$^+$

Preparation 121

The mixture of methyl 3-aminobenzoate (110.0 g) and 2,5-dimethoxytetrahydrofuran (141.4 ml) in acetic acid (330 ml) was heated under reflux for 50 minutes under stirring and the solvent was removed by concentration in vacuo. To the residue was added a mixture of ethyl acetate and water, and adjusted to pH 8 with potassium carbonate. The separated organic layer was washed with water and dried over magnesium sulfate. Evaporation of a solvent gave a residue, which was purified by column chromatography on silica gel eluting with chloroform. The eluted fractions containing the desired product were collected and evaporated in vacuo to give methyl 3-(pyrrol-1-yl)benzoate (112.84 g) as an oil.

IR (Film): 1720, 1590 cm$^{-1}$

NMR (DMSO-d$_6$, δ): 3.91 (3H, s), 6.30–6.38 (2H, m), 7.40–7.48 (2H, m), 7.59 (1H, dd, J=7.9 Hz, 7.9 Hz), 7.80–7.92 (2H, m), 8.05 (1H, dd, J=1.9 Hz, 1.9 Hz)

Preparation 122

Chlorosulfonyl isocyanate (18.2 ml) was dropwise added to a solution of methyl 3-(pyrrol-1-yl)benzoate (35.0 g) in dichloromethane (350 ml) at −10°~20° C. and the mixture was stirred for 1 hour at the same temperature. To the mixture was dropwise added N,N-dimethylformamide (105 ml) at the same temperature and the mixture was stirred for 1 hour at 0°–5° C. The reaction mixture was poured into water. The separated organic layer was washed with saturated aqueous sodium bicarbonate solution and water. The organic solution was dried over magnesium sulfate and evaporated in vacuo to give methyl 3-(2-cyanopyrrol-1-yl)benzoate (30.67 g).

mp: 89°–90° C.

IR (Nujol): 2220, 1715, 1590 cm$^{-1}$

NMR (DMSO-d$_6$, δ): 3.91 (3H, s), 6.49 (1H, dd, J=2.8 Hz, 3.9 Hz), 7.28 (1H, dd, J=1.6 Hz, 3.9 Hz), 7.65 (1H, dd, J=1.6 Hz, 2.8 Hz), 7.76 (1H, dd, J=8.0 Hz, 8.0 Hz), 7.85–7.92 (1H, m), 8.04–8.10 (2H, m)

(+) APCI MASS (m/z): 227 (M+H)$^+$

Elemental Analysis Calcd. for C$_{13}$H$_{10}$N$_2$O$_2$: C 69.02, H 4.46, N 12.38 Found C 68.69, H 4.46, N 12.26

EXAMPLE 1

28% Methanolic sodium methoxide (6.2 ml) was added to a solution of guanidine hydrochloride (3.2 g) in dry methanol (40.0 ml) and the mixture was stirred for 30 minutes at ambient temperature. To the mixture was added methyl 3-methylsulfonyl-5-(pyrrol-1-yl)benzoate (1.9 g) and the mixture was stirred for 7 hours at the same temperature. The solvent was removed by concentration and the residue was added to a mixture of ethyl acetate, tetrahydrofuran and water. The separated organic layer was washed with brine and dried over magnesium sulfate. The residue was obtained by evaporating a solvent, and purified by column chromatography on alumina eluting with a mixture of chloroform and methanol (19:1, V/V). The fractions containing the desired product were collected and evaporated in vacuo. The residue was recrystallized from a mixture of methanol and diisopropyl ether to give 2-[3-methylsulfonyl-5-(pyrrol-1-yl)benzoyl]guanidine (0.44 g).

mp: 235°–236° C.

IR (Nujol): 3500, 3440, 3340, 3240, 1635, 1600, 1320, 1135 cm$^{-1}$

NMR (DMSO-d$_6$, δ): 3.34 (3H, s), 6.30–6.40 (2H, m), 6.60–8.50 (4H, br), 7.47–7.57 (2H, m), 8.10–8.17 (1H, m), 8.40–8.48 (2H, m)

MASS (m/z): 306 (M$^+$)

EXAMPLE 2

The following compounds were obtained according to a similar manner to that of Example 1.

(1) 2-[{5-(Pyrrol-1-yl)pyridin-3-yl}carbonyl]guanidine
mp: 147°–150° C. (dec.)
IR (Nujol): 3400, 3300, 1590, 725 cm$^{-1}$
NMR (DMSO-d$_6$, δ) 6.30–6.40 (2H, m), 7.40–7.50 (2H, m), 8.39 (1H, dd, J=2.7, 1.7 Hz), 8.94 (1H, d, J=2.7 Hz)., 9.06 (1H, d, J=1.7 Hz), 6.4–7.4 (2H, br), 7.6–8.4 (2H, br)
MASS (m/z): 229 (M$^+$)

(2) 2-[{5-(3-Methyl-1,2,4-oxadiazol-5-yl)pyridin-3-yl}carbonyl]guanidine
mp: 219°–221° C.
IR (Nujol): 3400, 3310, 1660, 1520 cm$^{-1}$
NMR (DMSO-d$_6$, δ): 2.46 (3H, s), 8.96 (1H, t, J=2.1 Hz), 9.28 (1H, d, J=2.1 Hz), 9.38 (1H, d, J=2.1 Hz)
MASS (m/z): 247 (M$^+$+1)

(3) 2-[2-Methoxy-5-methylsulfonyl-3-(pyrrol-1-yl)benzoyl]guanidine
mp: 180°–183° C. (dec.)
IR (Nujol): 3410, 3300, 1675, 1605 cm$^{-1}$
NMR (DMSO-d$_6$, δ): 3.28 (3H, s), 3.56 (3H, s), 6.29 (2H, s), 7.16 (2H, s), 6.6–7.4 (2H, br), 7.81 (1H, d, J=2.3 Hz), 7.90 (1H, d, J=2.3 Hz), 7.5–8.3 (2H, br)

(4) 2-[3-Nitro-5-(pyrrol-1-yl)benzoyl]guanidine
mp: 211° C.
IR (Nujol) 1710, 1530, 1355, 1335, 1260 cm$^{-1}$
NMR (DMSO-d$_6$, δ): 6.36 (2H, m), 7.55 (2H, m), 6.6–7.4 (2H, br), 7.8–8.4 (2H, br), 8.40–8.45 (1H, m), 8.50–8.55 (1H, m), 8.65–8.70 (1H, m)
MASS (m/z): 274 (M$^+$+1)

(5) 2-[3-Methoxycarbonyl-5-(pyrrol-1-yl)benzoyl]guanidine
mp: 248°–250° C.
IR (Nujol): 3450, 3400, 3325, 1715, 1630, 720 cm$^{-1}$
NMR (DMSO-d$_6$, δ): 3.91 (3H, s), 6.32 (2H, m), 7.41 (2H, m), 8.08–8.10 (1H, m), 8.37–8.40 (1H, m), 8.50–8.60 (1H, m)
MASS (m/z): 287 (M$^+$+1)

(6) 2-[3-Phenoxybenzoyl]guanidine hydrochloride
mp: 144°–145° C.
IR (Nujol): 3340, 1700, 1360, 1260, 990, 860 cm$^{-1}$
NMR (DMSO-d$_6$, δ): 7.05–7.12 (3H, m), 7.15–7.50 (3H, m), 7.60–7.70 (2H, m), 7.95–8.10 (1H, m), 8.63 (2H, br s), 8.77 (2H, br s), 12.11 (1H, s)

(7) 2-[3-(3-Thienyl)benzoyl]guanidine hydrochloride
mp: 224°–225° C.
IR (Nujol): 3350, 1690, 1280, 745, 720 cm$^{-1}$
NMR (DMSO-d$_6$, δ): 7.6–7.8 (3H, m), 7.96–8.20 (3H, m), 8.57 (2H, s), 8.62 (1H, s), 8.88 (2H, s), 12.28 (1H, s)
MASS (m/z): 246 (M$^+$+1)

(8) 2-[3-(Pyrazol-1-yl)benzoyl]guanidine
mp: 155°–157° C.
IR (Nujol): 3430, 3330, 3200, 3100, 1670, cm$^{-1}$
NMR (DMSO-d$_6$, δ): 6.13–8.70 (4H, br), 6.55 (1H, dd, J=1.8 Hz, 2.4 Hz), 7.51 (1H, dd, J=7.9 Hz, 7.9 Hz), 7.76 (1H, d, J=1.4 Hz), 7.83–7.95 (1H, m), 7.99 (1H, d, J=7.9 Hz), 8.49 (1H, d, J=2.4 Hz), 8.54 (1H, d, J=1.8 Hz)

(9) 2-[3-(Pyrrol-1-yl)benzoyl]guanidine
mp: 172°–173° C.
IR (Nujol): 3310, 3120, 1665, 1635, 1600 cm$^{-1}$
NMR (DMSO-d$_6$, δ): 6.13–8.60 (4H, br), 6.22–6.35 (2H, m), 7.28–7.39 (2H, m), 7.47 (1H, dd, J=7.8 Hz, 7.8 Hz), 7.64 (1H, d, J=7.8 Hz), 7.94 (1H, d, J=7.8 Hz), 8.17 (1H, s)
MASS (m/z): 229 (M$^+$+1)
Elemental Analysis Calcd. for C$_{12}$H$_{12}$N$_4$O: C 63.15, H 5.30, N 24.55 Found: C 62.95, H 5.29, N 24.39

(10) 2-[3-(1H-Tetrazol-1-yl)benzoyl]guanidine
mp: 227°–230° C.
IR (Nujol): 3410, 3325, 3280, 3220, 3125, 1655, 1600 cm$^{-1}$
NMR (DMSO-d$_6$, δ): 6.37–8.60 (4H, br), 7.68 (1H, dd, J=7.9 Hz, 7.9 Hz), 7.98 (1H, d, J=7.9 Hz), 8.23 (1H, d, J=7.9 Hz), 8.55 (1H, dd, J=1.7 Hz, 1.7 Hz), 10.16 (1H, s)

(11) 2-[3-(Pyrrol-1-yl)benzoyl]guanidine
mp: 172°–173° C.
IR (Nujol): 3310, 3120, 1665, 1635, 1600 cm$^{-1}$
NMR (DMSO-d$_6$, δ): 6.13–8.60 (4H, br), 6.22–6.35 (2H, m), 7.28–7.39 (2H, m), 7.47 (1H, dd, J=7.8 Hz, 7.8 Hz), 7.64 (1H, d, J=7.8 Hz), 7.94 (1H, d, J=7.8 Hz), 8.17 (1H, s)
MASS (m/z): 229 (M$^+$+1)

(12) 2-[{5-(Pyrazol-3-yl)pyridin-3-yl}carbonyl]guanidine
mp: 264°–265° C.
IR (Nujol): 3440, 3310, 3170, 3100, 1690 cm$^{-1}$ NMR (DMSO-$d_6$, δ): 6.37–8.40 (4H, br), 6.85 (1H, d, J=2.3 Hz), 7.84 (1H, d, J=2.3 Hz), 8.74 (1H, dd, J=2.0 Hz, 2.0 Hz), 9.06 (1H, d, J=2.0 Hz), 9.11 (1H, d, J=2.0 Hz), 13.11 (1H, br s)

MASS (m/z): 231 ($M^+$+1)

Elemental Analysis Calcd. for $C_{10}H_{10}N_6O$: C 52.17, H 4.38, N 36.50 Found: C 52.22, H 4.50, N 36.31

(13) 2-[3,5-Di(pyrrol-1-yl)benzoyl]guanidine mp: 220°–221° C.

IR (Nujol): 3480, 3430, 3300, 3200, 1630, 1600 $cm^{-1}$

NMR (DMSO-$d_6$, δ): 6.28–6.39 (4H, m), 6.50–8.40 (4H, br), 7.45–7.53 (4H, m), 7.82 (1H, dd, J=2.1 Hz, 2.1 Hz), 8.03 (2H, d, J=2.1 Hz)

MASS (m/z): 294 ($M^+$+1)

Elemental Analysis Calcd. for $C_{16}H_{15}N_5O$: C 65.52, H 5.15, N 23.88 Found: C 65.79, H 5.22, N 23.60

(14) 2-[3-(2,5-Dimethylpyrrol-1-yl)benzoyl]guanidine mp: 204°–205° C.

IR (Nujol): 3430, 3350, 3300, 1650, 1630, 1600 $cm^{-1}$

NMR (DMSO-$d_6$, δ): 1.95 (6H, s), 5.80 (2H, s), 6.00–8.30 (4H, br), 7.32–7.39 (1H, m), 7.53 (1H, dd, J=7.7 Hz, 7.7 Hz), 7.92 (1H, dd, J=1,7 Hz, 1.7 Hz), 8.06–8.12 (1H, m)

MASS (m/z): 257 (M+1)

Elemental Analysis Calcd. for $C_{14}H_{16}N_4O$: C 65.61, H 6.29, N 21.86 Found: C 65.77, H 6.54, N 21.70

(15) 2-[2-(Pyrrol-1-yl)benzoyl]guanidine mp: 172°–173° C.

IR (Nujol): 3380, 1655, 1595 $cm^{-1}$

NMR (DMSO-$d_6$, δ): 6.10–6.18 (2H, m), 6.35–8.20 (4H, br), 6.94–7.03 (2H, m), 7.25 (1H, dd, J=1.6 Hz, 7.1 Hz), 7.30–7.48 (3H, m)

MASS (m/z): 229 ($M^+$+1)

(16) 2-[3-Methylsulfonyl-4-piperidino-5-(pyrrol-1-yl)benzoyl]guanidine mp: 178°–179° C.

IR (Nujol): 3425, 3350, 3170, 1650, 1590, 1140 $cm^{-1}$

NMR (DMSO-$d_6$, δ): 0.80–1.80 (6H, m), 2.10–2.48 (2H, m), 2.95–3.28 (2H, m), 3.40 (3H, S), 6.22–6.32 (2H, m), 6.40–8.40 (4H, br), 6.92–7.02 (2H, m), 8.14 (1H, d, J=2.0 Hz), 8.70 (1H, d, J=2.0 Hz)

MASS (m/z): 389 ($M^+$)

EXAMPLE 3

To a solution of guanidine hydrochloride (2.7 g) in methanol (12 ml) was added sodium methoxide (5.13 g, 28% in methanol) and the mixture was stirred for 15 minutes under nitrogen. To this mixture was added a solution of methyl 3-phenylbenzoate (1.20 g) in methanol (2 ml) and the mixture was stirred for 6 hours. The reaction mixture was poured into a mixture of ethyl acetate (100 ml) and water (50 ml). The organic layer was successively washed with 5N-sodium hydroxide aqueous solution and brine, dried over magnesium sulfate and evaporated in vacuo. The residue was purified by column chromatography on alumina (100 ml) and eluted with chloroform-methanol (10:1). The fractions containing the desired product were collected and evaporated in vacuo. The residue was crystallized from 4N-hydrogen chloride-ethyl acetate. The crystalline was recrystallized from ethanol to afford 2-[3-phenylbenzoyl]guanidine hydrochloride (274.0 mg).

mp: 168°–169° C.

IR (Nujol): 3325, 1700, 1630, 1260, 740 $cm^{-1}$

NMR (DMSO-$d_6$, δ): 7.4–7.6 (3H, m), 7.70 (1H, dd, J=7.8, 7.8 Hz), 7.8–7.9 (2H, m), 8.0–8.1 (2H, m), 8.40–8.45 (1H, m), 8.58 (2H, br), 8.82 (2H, br), 12.25 (1H, s)

MASS (m/z): 240 ($M^+$+1)

EXAMPLE 4

The following compound was obtained according to a similar manner to that of Example 3.

4,4-Dimethyl-6-diaminomethyleneaminocarbonyl-8-methylsulfonyl-4H-pyrrolo[2,1-c][1,4]benzoxazine hydrochloride mp: 165°–166° C.

IR (Nujol): 3370, 3280, 3200, 1695, 1320, 1130 $cm^{-1}$

NMR (DMSO-$d_6$, δ): 1.64 (6H, s), 3.57 (3H, s), 6.22 (1H, dd, J=1.3 Hz, 3.2 Hz), 6.38 (1H, dd, J=3.2 Hz, 3.2 Hz), 7.74 (1H, dd, J=1.3 Hz, 3.2 Hz), 7.98 (1H, d, J=2.1 Hz), 8.39 (1H, d, J=2.1 Hz), 8.45–8.85 (4H, m), 12.01 (1H, s)

MASS (m/z): 363 ($M^+$+1 of free compound)

EXAMPLE 5

To a solution of 6-carboxy-8-chloro-4,4-dimethyl-4H-pyrrolo[2,1-c][1,4]benzoxazine (0.7 g) and triethylamine (0.39 ml) in tetrahydrofuran (7 ml) and pyridine (14 ml) was added isobutyl chloroformate (0.38 g) under ice cooling. After being stirred for 2 hours at 7°–10° C., guanidine (0.3 g) was added to the reaction mixture and the whole was stirred for 8 hours at room temperature. The reaction mixture was poured into a mixture of ethyl acetate (100 ml) and water (100 ml). The organic layer was washed successively with 10% potassium carbonate aqueous solution, brine, dried over magnesium sulfate and evaporated in vacuo. The residue was treated with hydrogen chloride-ethanol to afford 8-chloro-4,4-dimethyl-6-diaminomethyleneaminocarbonyl-4H-pyrrolo[2,1-c][1,4]benzoxazine hydrochloride mp: 150° C.

IR (Nujol): 3350, 1690, 730 $cm^{-1}$

NMR (DMSO-$d_6$, δ): 1.60 (6H, s), 6.17 (1H, dd, J=3.4 Hz, 1.3 Hz), 6.33 (1H, dd, J=3.4 Hz, 3.4 Hz), 7.51 (1H, d, J=2.4 Hz), 7.63 (1H, dd, J=3.4 Hz, 1.3 Hz), 8.11 (1H, d, J=2.4 Hz), 8.4–8.9 (4H, m), 11.77 (1H, s)

EXAMPLE 6

4N-Hydrogen chloride-dioxane (3.0 ml) was added to a mixture of 2-[3-(1H-tetrazol-1-yl)benzoyl]guanidine (1.4 g) in methanol (30 ml) and the mixture was stirred for 1 hour at ambient temperature. To the mixture was added diisopropyl ether (30 ml) and the precipitate was collected by filtration. The precipitate was recrystallized from methanol to give 2-[3-(1H-tetrazol-1-yl)benzoyl]guanidine hydrochloride (1.05 g).

mp: 250°–251° C.

IR (Nujol): 3390, 3230, 3080, 1715, 1605 $cm^{-1}$

NMR (DMSO-$d_6$, δ): 7.89 (1H, dd, J=8.0 Hz, 8.0 Hz), 8.28 (1H, d, J=8.0 Hz), 8.32 (1H, d, J=8.0 Hz), 8.53–8.90 (5H, m), 10.28 (1H, s), 12.36 (1H, s)

MASS (m/z): 232 ($M^+$+1 of free compound)

EXAMPLE 7

The following compound was obtained according to a similar manner to that of Example 6.

(1) 2-[3-(Pyrazol-1-yl)benzoyl]guanidine hydrochloride mp: 252°–253° C.

IR (Nujol): 3360, 3270, 1700, 1620, 1585 $cm^{-1}$

NMR (DMSO-$d_6$, δ): 6.57–6.67 (1H, m), 7.73 (1H, dd, J=8.0 Hz, 8.0 Hz), 7.83 (1H, d, J=1.6 Hz), 8.00–8.10 (1H, m), 8.17–8.26 (1H, m), 8.55–8.73 (3H, m), 8.73–8.90 (3H, m), 12.28 (1H, s)

MASS (m/z): 230 ($M^+$+1 of free compound)

(2) 2-[3-(Pyrrol-1-yl)benzoyl]guanidine hydrochloride
mp: 215°–216° C.

IR (Nujol): 3350, 3100, 1700, 1690, 1625 cm$^{-1}$

NMR (DMSO-d$_6$, δ): 6.28–6.38 (2H, m), 7.60–7.75 (3H, m), 7.90–8.63 (2H, m), 8.45 (1H, s), 8.61 (2H, s), 8.88 (2H, s), 12.43 (1H, s)

Elemental Analysis Calcd. for C$_{12}$H$_{12}$N$_4$O.HCl: C 54.45, H 4.95, N 21.17, Cl 13.39 Found: C 54.52, H 5.04, N 21.11, Cl 13.22

EXAMPLE 8

To a solution of guanidine hydrochloride (62.1 g) in N,N-dimethylformamide (150 ml) was added 28% sodium methoxide in methanol (106 ml) under nitrogen. After being stirred for 30 minutes at room temperature, to the reaction mixture was added a solution of methyl 3-hydroxymethyl-5-(pyrrol-1-yl)benzoate (30.0 g) in N,N-dimethylformamide (150 ml). After being stirred for 21 hours at room temperature, the reaction mixture was poured into water (1.5 l) with stirring. The resulting precipitate was collected by filtration, washed with water and purified by column chromatography on silica gel eluting with a mixture of chloroform and methanol (10:1). The eluted fractions containing the desired product were collected and evaporated in vacuo. The residue was dissolved in ethanol (70 ml) and crystallized from slight excess 4N-hydrogen chloride-ethyl acetate. The crystalline was recrystallized from an aqueous ethanol to afford 2-[3-hydroxymethyl-5-(pyrrol-1-yl)benzoyl]guanidine hydrochloride (7.3 g).

mp: 198°–199° C.

IR (Nujol): 3350, 3100, 1720 cm$^{-1}$

NMR (DMSO-d$_6$, δ): 4.64 (2H, s), 6.3–6.4 (2H, m), 7.6–7.7 (2H, m), 7.86 (2H, m), 8.34 (1H, m), 8.59 (2H, br s), 8.84 (2H, br s), 12.32 (1H, s)

MASS (m/z): 259 (M$^+$+1)

EXAMPLE 9

The following compounds were obtained according to similar manners to those of Examples 1, 3 and 8.
(1) 2-[3-(2-Methylphenyl)benzoyl]guanidine hydrochloride
mp: 187°–189° C.

IR (Nujol): 1680, 1560, 1230, 740 cm$^{-1}$

NMR (DMSO-d$_6$, δ): 2.26 (3H, s), 7.28–7.34 (4H, m), 7.63–7.74 (2H, m), 8.07 (1H, s), 8.14 (1H, ddd, J=6.7 Hz, 2.1 Hz, 2.1 Hz), 8.58 (2H, br s), 8.75 (2H, br s), 12.04 (1H, m)

MASS (m/z): 254 (M$^+$+1)
(2) 2-[3-(2,5-Dichloropyrrol-1-yl)benzoyl]guanidine
mp: 201°–204° C.

IR (Nujol): 3460, 3300, 3180, 1630, 1595 cm$^{-1}$

NMR (DMSO-d$_6$, δ): 6.20–6.83 (4H, m), 6.36 (2H, s), 7.45 (1H, d, J=7.7 Hz), 7.60 (1H, dd, J=7.7 Hz), 7.99 (1H, s), 8.18 (1H, d, J=7.7 Hz)
(3) 2-[3-(2-Acetylpyrrol-1-yl)benzoyl]guanidine IR (Nujol): 3100–3300, 1600–1660 cm$^{-1}$ NMR (DMSO-d$_6$, δ): 2.41 (3H, s), 6.30–8.30 (4H, br), 6.65–6.70 (1H, m), 7.38–7.45 (1H, m), 7.53 (1H, dd, J=7.8 Hz, 7.8 Hz), 7.75 (1H, d, J=7.8 Hz), 8.04 (1H, d, J=7.8 Hz), 8.15–8.18 (1H, m), 8.21–8.24 (1H, m)
(4) 2-[4-n-Butyl-3-(pyrrol-1-yl)benzoyl]guanidine
mp: 163°–165° C.

IR (Nujol): 3400, 3170, 1635, 1590 cm$^{-1}$

NMR (DMSO-d$_6$, δ): 0.77 (3H, t, J=7.1 Hz), 1.05–1.45 (4H, m), 2.42–2.53 (2H, m), 6.10–8.40 (4H, br), 6.19–6.25 (2H, m), 6.85–6.90 (2H, m), 7.38 (1H, d, J=7.9 Hz), 7.92–8.03 (2H, m)

(5) 2-[4-Methyl-3-(pyrrol-1-yl)benzoyl]guanidine
mp: 182°–185° C.

IR (Nujol): 3400, 3170, 1635, 1590 cm$^{-1}$

NMR (DMSO-d$_6$, δ): 2.19 (3H, s), 6.10–8.40 (4H, br), 6.20–6.25 (2H, m), 6.90–6.95 (2H, m), 7.37 (1H, d, J=8.3 Hz), 7.91–8.00 (2H, m)
(6) 2-[3-(2-Carbamoylpyrrol-1-yl)benzoyl]guanidine
mp: 155°–156° C.

IR (Nujol): 3450, 3360, 1655, 1600 cm$^{-1}$

NMR (DMSO-d$_6$, δ): 6.21 (1H, dd, J=2.8 Hz, 3.7 Hz), 6.38–8.20 (6H, br), 6.90 (1H, dd, J=1.7 Hz, 3.7 Hz), 7.00–7.05 (1H, m), 7.27–7.36 (1H, m), 7.43 (1H, dd, J=7.6 Hz, 7.6 Hz), 7.91–7.95 (1H, m), 7.95–8.03 (1H, m)
(7) 2-[3-[(Z)-2-Hydroxyiminomethylpyrrol-1-yl]benzoyl]guanidine
mp: 131°–132° C.

IR (Nujol): 3380, 3100, 1650, 1600 cm$^{-1}$

NMR (DMSO-d$_6$, δ): 6.20–8.70 (4H, br), 6.33–6.39 (1H, m), 7.02 (1H, s), 7.11–7.16 (1H, m), 7.28–7.34 (1H, m), 7.46–7.64 (2H, m), 8.00–8.20 (2H, m), 11.45 (1H, s)
(8) 2-[3-[(E)-2-Hydroxyiminomethylpyrrol-1-yl]benzoyl]guanidine
mp: 158°–159° C.

IR (Nujol): 3440, 3300, 3130, 1660, 1600 cm$^{-1}$

NMR (DMSO-d$_6$, δ): 6.15–8.40 (4H, m), 6.26–6.32 (1H, m), 6.60–6.64 (1H, m), 7.08–7.11 (1H, m), 7.44 (1H, d, J=7.8 Hz), 7.53 (1H, dd, J=7.8 Hz, 7.8 Hz), 7.77 (1H, s), 8.01 (1H, s), 8.09 (1H, d, J=7.8 Hz), 10.84 (1H, s)
(9) 2-[3-(2-Dimethylaminomethylpyrrol-1-yl)benzoyl]guanidine
mp: 91°–94° C.

IR (Nujol): 3370, 3200, 1650, 1595 cm$^{-1}$

NMR (DMSO-d$_6$, δ): 2.08 (6H, s), 3.22 (2H, s), 6.12–6.18 (1H, m), 6.30–8.40 (4H, br), 7.47 (1H, d, J=7.8 Hz, 7.8 Hz), 7.65 (1H, d, J=7.8 Hz), 8.03 (1H, d, J=7.8 Hz), 8.15 (1H, s)
(10) 2-[3-(2-Cyanopyrrol-1-yl)benzoyl]guanidine
mp: 136°–138° C.

IR (Nujol): 3390, 2220, 1637 cm$^{-1}$

NMR (DMSO-d$_6$, δ): 6.30–8.40 (4H, br), 6.46 (1H, dd, J=2.8 Hz, 3.9 Hz), 7.24 (1H, dd, J=1.6 Hz, 3.9 Hz), 7.56 (1H, dd, J=1.6 Hz, 2.8 Hz), 7.58–7.69 (2H, m), 8.11–8.19 (2H, m)
(11) 2-[4-n-Butyl-3-(2-cyanopyrrol-1-yl)benzoyl]guanidine IR (Film): 3350, 2230, 1660–1590 (br) cm$^{-1}$ NMR (DMSO-d$_6$, δ): 0.76 (3H, t, J=7.2 Hz), 1.05–1.46 (4H, m), 2.30–2.55 (2H, m), 6.20–8.70 (4H, br), 6.44 (1H, dd, J=2.7 Hz, 3.9 Hz), 7.15–7.22 (1H, dd, J=1.5 Hz, 3.9 Hz), 7.36–7.41 (1H, dd, J=1.5 Hz, 2.7 Hz), 7.50 (1H, d, J=8.0 Hz), 8.01 (1H, d, J=1.5 Hz), 8.13 (1H, dd, J=1.5 Hz, 8.0 Hz)
(12) 2-[3-[(4-Hydroxypiperidin-1-yl)carbonyl]-5-(pyrrol-1-yl)benzoyl]guanidine
mp: 227°–228° C.

IR (Nujol): 3400, 1630, 1610 cm$^{-1}$

NMR (DMSO-d$_6$, δ): 1.2–2.0 (4H, m), 3.0–4.2 (5H, m), 4.82 (1H, d, J=3.4 Hz), 6.2–6.4 (2H, m), 7.3–7.5 (2H, m), 7.6–7.7 (1H, m), 7.8–7.9 (1H, m), 8.1–8.2 (1H, m)

MASS (m/z): 356 (M$^+$+1)
(13) 2-[3-Carboxy-5-(pyrrol-1-yl)benzoyl]guanidine
mp: >250° C.

IR (Nujol): 3370, 1680, 1580 cm$^{-1}$

NMR (DMSO-d$_6$, δ): 6.2–6.4 (2H, m), 7.4–7.5 (2H, m), 8.1–8.2 (1H, m), 8.3–8.4 (1H, m), 8.8–8,9 (1H, m)

MASS (m/z): 273 (M$^+$+1)
(14) 2-[3-[(4-Methylpiperazin-1-yl)carbonyl]-5-(pyrrol-1-yl)benzoyl]guanidine dihydrochloride
mp: 220°–221° C.

IR (Nujol): 3300, 1700, 1640, 1600 cm$^{-1}$

NMR (DMSO-d$_6$, δ): 2.78 (3H, s), 3.0–3.8 (8H, m), 6.3–6.4 (2H, m), 7.7–7.8 (2H, m), 7.9–8.1 (2H, m), 8.5–8.6 (1H, m), 8.70 (2H, br s), 8.91 (2H, br s)

MASS (m/z): 355 (M⁺+1)

(15) 2-[3-Methoxymethyl-5-(pyrrol-1-yl)benzoyl]guanidine hydrochloride
mp: 193°–194° C.
IR (Nujol): 3340–3100, 1690, 1620, 1600 cm⁻¹
NMR (DMSO-d₆, δ): 3.36 (3H, s), 4.55 (2H, s), 6.3–6.4 (2H, m), 7.6–7.7 (2H, m), 7.8–7.9 (2H, mn), 8.3–8.4 (1H, m), 8.61 (2H, br s), 8.85 (2H, br s), 12.39 (1H, s)
MASS (m/z): 273 (M⁺+1)

(16) 2-[5-(2-Cyanopyrrol-1-yl)-3-hydroxymethylbenzoyl]guanidine hydrochloride
mp: 246°–247° C.
IR (Nujol): 3150, 2220, 1710 cm⁻¹
NMR (DMSO-d₆, δ): 4.68 (2H, s), 6.5–6.6 (1H, m), 7.2–7.4 (1H, m), 7.7–7.8 (1H, m), 7.8–7.9 (1H, m), 8.1–8.2 (1H, m), 8.2–8.3 (1H, m), 8.69 (4H, br s), 12.28 (1H, s)
MASS (m/z): 284 (M⁺+1)

(17) 2-[3-[(2-Dimethylaminoethyl)carbamoyl]-5-(pyrrol-1-yl)benzoyl]guanidine
mp: 140°–145° C.
IR (Nujol): 3400, 1640, 1580 cm⁻¹
NMR (DMSO-d₆, δ): 2.25 (6H, s), 2.4–2.6 (2H, m), 3.3–3.5 (2H, m), 6.3–6.4 (2H, m), 7.4–7.5 (2H, m), 8.0–8.1 (1H, m), 8.2–8.3 (1H, m), 8.4–8.5 (1H, m), 8.64 (1H, t, J=5.6 Hz)
MASS (m/z): 343 (M⁺+1)

(18) 2-[3-(2-Cyano-5-dimethylaminomethylpyrrol-1-yl)benzoyl]guanidine dihydrochloride
mp: 135°–138° C.
IR (Nujol): 3300, 2230, 1700 cm⁻¹
NMR (DMSO-d₆, δ): 2.57 (6H, s), 4.28 (2H, s), 6.95 (1H, d, J=4.0 Hz), 7.32 (1H, d, J=4.0 Hz), 7.86 (1H, dd, J=7.9 Hz, 7.9 Hz), 7.96 (1H, d, J=7.9 Hz), 8.34–8.42 (2H, m), 8.70 (2H, s), 8.85 (2H, s), 10.94 (1H, s), 12.52 (1H, s)
MASS (m/z): 311 (M⁺+1 of free compound)

(19) 2-[3-(2-Methylpyrrol-1-yl)benzoyl]guanidine hydrochloride
mp: 213°–214° C.
IR (Nujol): 3350, 1700 cm⁻¹
NMR (DMSO-d₆, δ): 2.23 (3H, s), 6.00–6.04 (1H, m), 6.10–6.16 (1H, m), 7.00–7.05 (1H, m), 7.68–7.80 (2H, m), 8.03–8.11 (2H, m), 8.56 (2H, s), 8.67 (2H, s), 12.07 (1H, s)
MASS (m/z): 243 (M⁺+1 of free compound)

(20) 2-[3-(4-Cyanophenyl)benzoyl]guanidine hydrochloride
mp: 243°–245° C.
IR (Nujol): 3350, 2230, 1710 cm⁻¹
NMR (DMSO-d₆, δ): 7.75 (1H, dd, J=7.7 Hz, 7.7 Hz), 7.98 (2H, d, J=8.6 Hz), 8.08–8.15 (4H, m), 8.54 (1H, s), 8.56 (2H, br s), 8.77 (2H, br s), 12.27 (1H, s)
MASS (m/z): 265 (M⁺+1)

(21) 2-[3-(2-Methylsulfonylphenyl)benzoyl]guanidine hydrochloride
mp: 236°–238° C.
IR (Nujol): 3200, 1710, 1560, 1300, 1230, 1140, 960, 760 cm⁻¹
NMR (DMSO-d₆, δ): 2.93 (3H, s), 7.48 (1H, dd, J=7.2 Hz, 1.6 Hz), 7.62–7.85 (4H, m), 8.10–8.14 (2H, m), 8.23 (1H, d, J=7.7 Hz), 8.59 (2H, br s), 8.77 (2H, br s), 12.17 (1H, s)
MASS (m/z): 318 (M⁺+1)

(22) 2-[3-(2-Trifluoromethylphenyl)benzoyl]guanidine hydrochloride
mp: 141°–143° C.
IR (Nujol): 3300, 1700, 1230, 1110, 740 cm⁻¹
NMR (DMSO-d₆, δ): 7.51 (1H, d, J=7.5 Hz), 7.62–7.82 (4H, m), 7.88 (1H, d, J=7.6 Hz), 8.02 (1H, s), 8.20–8.25 (1H, m), 8.57 (2H, br s), 8.67 (2H, br s), 11.99 (1H, s)

MASS (m/z): 308 (M⁺+1)

(23) 2-[3-(2-Methoxyphenyl)benzoyl]guanidine hydrochloride
mp: 182°–183° C.
IR (Nujol): 3340, 1700, 1250, 1020, 730 cm⁻¹
NMR (DMSO-d₆, δ): 3.79 (3H, s), 7.03–7.17 (2H, m), 7.36–7.47 (2H, m), 7.62 (1H, dd, J=7.9 Hz, 7.9 Hz), 7.84 (1H, d, J=7.9 Hz), 8.11 (1H, d, J=7.9 Hz), 8.18 (1H, s), 8.61 (2H, br s), 8.79 (2H, br s), 12.10 (1H, s)
MASS (m/z): 270 (M⁺+1)

(24) 2-[3-(2-Naphthyl)benzoyl]guanidine hydrochloride
mp: 132°–134° C.
IR (Nujol): 1700, 1560, 1250, 750 cm⁻¹
NMR (DMSO-d₆, δ): 7.55–7.59 (2H, m), 7.75 (1H, dd, J=7.8 Hz, 7.8 Hz), 7.96–8.22 (6H, m), 8.49 (1H, s), 8.55 (2H, br s), 8.61 (1H, s), 8.78 (2H, br s), 12.20 (1H, s)
MASS (m/z): 290 (M⁺+1)

(25) 2-[3-(1-Naphthyl)benzoyl]guanidine hydrochloride
mp: 208°–210° C.
IR (Nujol): 3300, 1700, 1250, 1230, 720 cm⁻¹
NMR (DMSO-d₆, δ): 7.52–7.88 (7H, m), 8.00–8.07 (2H, m), 8.20–8.30 (2H, m), 8.66 (2H, br s), 8.79 (2H, br s), 12.17 (1H, s)
MASS (m/z): 290 (M⁺+1)

(26) 2-[3-(3-Methoxyphenyl)benzoyl]guanidine hydrochloride
mp: 166°–167° C.
IR (Nujol): 3250, 1700, 1250, 1030, 730 cm⁻¹
NMR (DMSO-d₆, δ): 3.87 (3H, s), 6.96–7.04 (1H, m), 7.36–7.42 (3H, m), 7.68 (1H, dd, J=7.8 Hz, 7.8 Hz), 8.01–8.10 (2H, m), 8.50 (1H, s), 8.62 (2H, br s), 8.89 (2H, br s), 12.38 (1H, s)
MASS (m/z): 270 (M⁺+1)

(27) 2-[3-(2-Morpholinoethylcarbamoyl)-5-(pyrrol-1-yl)benzoyl]guanidine dihydrochloride
mp: 195°–198° C. (dec.)
IR (Nujol): 1695, 1250, 720 cm⁻¹
NMR (DMSO-d₆, δ): 3.0–4.1 (10H, m), 6.30–6.36 (2H, m), 7.79–7.81 (2H, m, 8.35 (1H, s), 8.53 (1H, s), 8.63 (1H, s), 8.80 (2H, s), 9.34 (1H, m), 10.85 (1H, br s), 12.47 (1H, s)
MASS (m/z): 385 (M+1)

(28) 2-[3-(Thiophen-2-yl)benzoyl]guanidine hydrochloride
mp: 225°–226° C.
IR (Nujol): 3350, 1700, 1280, 725 cm⁻¹
NMR (DMSO-d₆, δ): 7.15–7.25 (1H, m), 7.60–7.70 (2H, m), 7.80–7.85 (1H, m), 7.95–8.05 (2H, m), 8.48–8.50 (1H, m), 8.59 (2H, br), 8.81 (2H, br), 12.21 (1H, s)
MASS (m/z): 246 (M+1)

(29) 2-[3-(Thiazol-2-yl)benzoyl]guanidine dihydrochloride
mp: 236°–239° C. (dec.)
IR (Nujol): 3375, 1700, 1455, 750 cm⁻¹
NMR (DMSO-d₆, δ): 7.84 (1H, t, J=7.8 Hz, 7.8 Hz), 7.91 (1H, d, J=3.2 Hz), 8.01 (1H, d, J=3.2 Hz), 8.25–8.32 (2H, m), 8.63–8.65 (1H, m), 8.75 (2H, br), 8.83 (2H, br), 12.34 (1H, s)
MASS (m/z): 247 (M+1)

(30) 2-[3-Chloro-5-(pyrrol-1-yl)benzoyl]guanidine hydrochloride
mp: 244°–245° C.
IR (Nujol): 1690, 1580, 720 cm⁻¹
NMR (DMSO-d₆, δ): 6.30–6.34 (2H, m), 7.68–7.73 (2H, m), 7.87 (1H, dd, J=1.5 Hz, 1.5 Hz), 8.11 (1H, dd, J=1.5 Hz, 1.5 Hz), 8.40 (1H, dd, J=1.5 Hz, 1.5 Hz), 8.58 (2H, br s), 8.77 (2H, br s), 12.42 (1H,br s)
MASS (m/z): 263 (M+1)

(31) 2-[3-Acetyl-5-(pyrrol-1-yl)benzoyl]guanidine hydrochloride mp: 292°–293° C. (dec.)

IR (Nujol): 1690, 1240, 1080, 870 cm$^{-1}$

NMR (DMSO-d$_6$, δ) 2.75 (3H, s), 6.3–6.4 (2H, m), 7.7–7.8 (2H, m), 8.34 (1H, s), 8.40 (1H, s), 8.62 (1H, s), 8.63 (2H, br s), 8.83 (2H, br s), 12.55 (1H, s)

MASS (m/z): 271 (M+1)

(32) 2-[3-(4-Methoxyphenyl)benzoyl]guanidine hydrochloride mp: 242°–243° C.

IR (Nujol): 1690, 1295, 830 cm$^{-1}$

NMR (DMSO-d$_6$, δ): 3.81 (3H, s), 7.06 (2H, d, J=8.8 Hz), 7.65 (1H, dd, J=7.9 Hz, 7.9 Hz), 7.81 (2H, d, J=8.8 Hz), 7.95–8.05 (2H, m), 8.41 (1H, dd, J=1.7 Hz), 8.56 (2H, br s), 8.81 (2H, br s), 12.20 (1H, s)

MASS (m/z): 270 (M+1)

(33) 2-[3-(3-Morpholinopropylcarbamoyl)-5-(pyrrol-1-yl) benzoyl]guanidine dihydrochloride mp: 195°–197° C. (dec.)

IR (Nujol): 1700, 1650, 1240 cm$^{-1}$

NMR (DMSO-d$_6$, δ): 1.9–2.2 (2H, m), 2.9–3.3 (4H, m), 3.3–3.55 (4H, m), 3.7–4.1 (4H, m), 6.3–6.4 (2H, m), 7.7–7.8 (2H, m), 8.37 (1H, s), 8.41 (1H, s) 8.61 (1H, s), 8.72 (2H, s), 8.85 (2H, s), 9.16 (1H, t, J=5.6 Hz), 10.96 (1H, br s), 12.55 (1H, s)

MASS (m/z): 399 (M+1)

(34) 2-[2-Naphthoyl]guanidine hydrochloride mp: 276°–279° C. (dec.)

IR (Nujol): 1690, 1620, 1200 cm$^{-1}$

NMR (DMSO-d$_6$, δ): 7.6–7.8 (2H, m), 8.0–8.2 (4H, m), 8.67 (2H, s), 8.88 (2H, s), 8.96 (1H, s), 12.33 (1H, s)

MASS (m/z): 214 (M+1)

(35) 2-[3-(2-Cyanophenyl)benzoyl]guanidine hydrochloride mp: 204°–205° C.

IR (Nujol): 2225, 1690, 720 cm$^{-1}$

NMR (DMSO-d$_6$, δ): 7.6–7.9 (4H, m), 8.00 (1H, dd, J=7.2 Hz, 7.2 Hz), 8.20–8.35 (2H, m), 8.60 (2H, br s), 8.77 (2H, br s), 12.25 (1H, s)

MASS (m/z): 265 (M+1)

(36) 4,4-Dimethyl-8-(diaminomethyleneaminocarbonyl)-4H-pyrrolo[2,1-c][1,4]benzoxazine hydrochloride mp: 276°–277° C.

IR (Nujol): 3480, 3180, 1692, 1630 cm$^{-1}$

NMR (DMSO-d$_6$, δ): 1.60 (6H, s), 6.15 (1H, dd, J=1.4 Hz, 3.2 Hz), 6.33 (1H, dd, J=3.2 Hz, 3.2 Hz), 7.23 (1H, d, J=8.6 Hz), 7.77 (1H, dd, J=1.4 Hz, 3.2 Hz), 7.83 (1H, dd, J=2.1 Hz, 8.6 Hz), 8.47 (2H, s), 8.71 (1H, d, J=2.1 Hz), 8.79 (2H, s), 12.13 (1H, s)

MASS (m/z): 285 (M$^+$+1 of free compound)

EXAMPLE 10

Methyl 3-(2-cyano-5-methylpyrrol-1-yl)benzoate (0.8 g) was added to the mixture of guanidine hydrochloride (1.6 g) and 28% methanolic sodium methoxide (3.0 ml) in N,N-dimethylformamide (8.0 ml) and the mixture was stirred for 4 hours at ambient temperature. The mixture was poured into the mixture of ethyl acetate and water. The separated organic layer was washed with water, dried over magnesium sulfate and evaporated in vacuo. The residue was dissolved in methanol (10 ml) and to the mixture was added methanesulfonic acid (0.4 ml). The mixture was stirred for 30 minutes and then diisopropyl ether was added thereto. The isolated precipitate was collected by filtration and recrystallized from methanol-water to give 2-[3-(2-cyano-5-methylpyrrol-1-yl)benzoyl]guanidine methanesulfonate (0.98 g).

mp: 233°–234° C.

IR (Nujol): 3300, 2220, 1713, 1165, 1045 cm$^{-1}$

NMR (DMSO-d$_6$, δ): 2.15 (3H, s), 2.34 (3H, s), 6.26 (1H, d, J=3.9 Hz), 7.14 (1H, d, J=3.9 Hz), 7.83–7.89 (2H, m), 7.96–7.99 (1H, m), 8.07–8.14 (1H, m), 8.14–8.60 (4H, br s), 11.34 (1H, s)

MASS (m/z): 268 (M$^+$+1 of free compound)

EXAMPLE 11

The following compound was obtained according to a similar manner to that of Example 10.

2-[3-Hydroxymethyl-5-(pyrrol-1-yl)benzoyl]guanidine methanesulfonate mp: 171°–172° C.

IR (Nujol): 3330, 3120, 1690, 1600 cm$^{-1}$

NMR (DMSO-d$_6$, δ): 2.42 (3H, s), 4.66 (2H, s), 6.3–6.4 (2H, m), 7.4–7.5 (2H, m), 7.7–8.0 (3H, m), 8.43 (4H, br s), 11.41 (1H, s)

MASS (m/z): 259 (M$^+$+1)

EXAMPLE 12

28% Sodium methoxide in methanol (8.6 ml) was added to guanidine hydrochloride (4.7 g) in dry N,N-dimethylformamide (14 ml), and the mixture was stirred for 20 minutes at ambient temperature. To the mixture was added dimethyl 5-(2-cyanopyrrol-1-yl)isophthalate (1.4 g) and the mixture was stirred for 4 hours at the same temperature. The reaction mixture was poured into a water (150 ml) under stirring. The isolated precipitate was collected by filtration, washed with water and dried to give 2-[3-(2-cyanopyrrol-1-yl)-5-(diaminomethyleneaminocarbonyl) benzoyl]guanidine (0.88 g).

mp: 251°–253° C.

IR (Nujol): 3340 (br), 2220, 1690, 1640 cm$^{-1}$

NMR (DMSO-d$_6$, δ): 6.03–8.70 (8H, br), 6.42–6.49 (1H, m), 7.20–7.26 (1H, m), 7.54–7.59 (1H, m), 8.22 (2H, s), 8.85 (1H, s)

EXAMPLE 13

The following compound was obtained according to a similar manner to that of Example 12.

2-[3-(Diaminomethyleneaminocarbonyl)-5-(pyrrol-1-yl) benzoyl]guanidine dihydrochloride mp: 257° C. (dec.)

IR (Nujol): 1700, 1575, 1070 cm$^{-1}$

NMR (DMSO-d$_6$, δ): 6.34–6.37 (2H, m), 7.90–7.93 (2H, m), 8.37 (1H, s), 8.66 (2H, br s), 8.79 (4H, br s), 12.58 (1H, s)

MASS (m/z): 314 (M+1)

EXAMPLE 14

2-Chloro-1-methylpyridinium iodide (3.6 g) was added to a mixture of 5-cyano-3-(pyrrol-1-yl)benzoic acid (2.0 g), guanidine hydrochloride (2.7 g) and triethylamine (7.2 ml) in N,N-dimethylformamide (30 ml), and the mixture was stirred for 4 hours at ambient temperature. The reaction mixture was added to a mixture of ethyl acetate, tetrahydrofuran and water, and adjusted to pH 10 with potassium carbonate. The separated organic layer was washed with brine and dried over magnesium sulfate. The solvent was removed by concentration and the residue was triturated with ether to give 2-[5-cyano-3-(pyrrol-1-yl)benzoyl] guanidine (1.49 g).

mp: 198°–200° C.

IR (Nujol): 3480, 3400, 3300, 2230, 1620, 1600 cm$^{-1}$

NMR (DMSO-d$_6$, δ): 6.20–8.60 (4H, m), 6.32–6.36 (2H, m), 7.47–7.51 (2H, m), 8.24 (2H, s), 8.43 (1H, s)

EXAMPLE 15

The following compounds were obtained according to a similar manner to that of Example 14.

(1) 2-[3-(2-Cyanopyrrol-1-yl)benzoyl]guanidine mp: 136°–138° C.

IR (Nujol): 3390, 2220, 1637 cm$^{-1}$

NMR (DMSO-d$_6$, δ): 6.30–8.40 (4H, br), 6.46 (1H, dd, J=2.8 Hz, 3.9 Hz), 7.24 (1H, dd, J=1.6 Hz, 3.9 Hz), 7.56 (1H, dd, J=1.6 Hz, 2.8 Hz), 7.58–7.69 (2H, m), 8.11–8.19 (2H, m)

(2) 2-[3-(3-Cyanopyrrol-1-yl)benzoyl]guanidine mp: 203°–205° C.

IR (Nujol): 3420, 3300, 3140, 2220, 1655, 1630, 1660 cm$^{-1}$

NMR (DMSO-d$_6$, δ): 6.40–8.20 (4H, br), 6.72–6.76 (1H, m), 7.47–7.75 (3H, m), 8.00–8.10 (1H, m), 8.18–8.23 (2H, m)

(3) 2-[3-(2-Benzyloxycarbonylpyrrol-1-yl)benzoyl]guanidine

IR (Film): 3400, 1705, 1630 cm$^{-1}$

NMR (DMSO-d$_6$, δ): 5.12 (2H, s), 6.28–8.35 (4H, br), 6.34 (1H, dd, J=2.7 Hz, 3.9 Hz), 7.10 (1H, dd, J=1.8 Hz, 3.9 Hz), 7.20–7.51 (8H, m), 7.98–8.02 (1H, m), 8.03–8.09 (1H, m)

(4) 2-[4-Phenylbenzoyl]guanidine hydrochloride mp: 270°–272° C. (dec.)

IR (Nujol): 3300, 1685, 1260, 745 cm$^{-1}$

NMR (DMSO-d$_6$, δ): 7.40–7.65 (3H, m), 7.70–7.90 (2H, m), 7.92 (2H, d, J=8.5 Hz), 8.26 (2H, d, J=8.5 Hz), 8.63 (2H, s), 8.84 (2H, s), 12.14 (1H, s)

MASS (m/z): 240 (M+1)

EXAMPLE 16

The following compounds were obtained according to a similar manner to that of Example 6.

(1) 2-[3-[(Z)-2-Hydroxyiminomethylpyrrol-1-yl]benzoyl]guanidine hydrochloride mp: 176°–178° C. (dec.)

IR (Nujol): 3320, 3100, 1705, 1630 cm$^{-1}$

NMR (DMSO-d$_6$, δ): 6.36–6.42 (1H, m), 7.11 (1H, s), 7.28–7.36 (2H, m), 7.72–7.81 (2H, m), 8.12 (1H, s), 8.19–8.25 (1H, m), 8.72 (2H, s), 8.79 (2H, s), 12.36 (1H, s)

MASS (m/z): 272 (M$^+$+1 of free compound)

(2) 2-[3-[(E)-2-Hydroxyiminomethylpyrrol-1-yl]benzoyl]guanidine hydrochloride mp: 207°–208° C. (dec.)

IR (Nujol): 3250, 3100, 1695 cm$^{-1}$

NMR (DMSO-d$_6$, δ): 6.36–6.42 (1H, m), 7.09 (1H, s), 7.25–7.35 (2H, m), 7.73–7.82 (2H, m), 8.08 (1H, s), 8.15–8.22 (1H, s), 8.50–8.80 (4H, m), 11.47 (1H, s), 12.17 (1H, s)

MASS (m/z): 272 (M$^+$+1 of free compound)

(3) 2-[3-(2-Dimethylaminomethylpyrrol-1-yl)benzoyl]guanidine dihydrochloride mp: 210°–211° C. (dec.)

IR (Nujol): 3350, 3080, 1690–1705 (br), 1630 cm$^{-1}$

NMR (DMSO-d$_6$, δ): 2.49 (6H, s), 4.32 (2H, s), 6.32–6.38 (1H, m), 6.70–6.75 (1H, m), 7.20–7.25 (1H, m), 7.68–7.80 (2H, m), 8.15–8.25 (2H, m), 8.76 (2H, s), 8.89 (2H, s), 10.49 (1H, s), 12.56 (1H, s)

MASS (m/z): 286 (M$^+$+1 of free compound)

(4) 2-[3-(2,5-Dichloropyrrol-1-yl)benzoyl]guanidine hydrochloride mp: 204°–205° C.

IR (Nujol): 3330, 3240, 3100, 1685 cm$^{-1}$

NMR (DMSO-d$_6$, δ): 6.41 (2H, s), 7.71–7.89 (2H, m), 8.06 (1H, s), 8.37 (1H, d, J=7.3 Hz), 8.67 (2H, s), 8.71 (2H, s), 12.20 (1H, s)

MASS (m/z): 297 (M$^+$+1 of free compound)

(5) 2-[3-(2-Carbamoylpyrrol-1-yl)benzoyl]guanidine hydrochloride mp: 155°–158° C.

IR (Nujol): 3300, 3120, 1700, 1650, 1585 cm$^{-1}$

NMR (DMSO-d$_6$, δ): 6.27 (1H, dd, J=2.9 Hz, 3.6 Hz), 6.70–8.20 (2H, br), 6.97 (1H, dd, J=1.6 Hz, 3.6 Hz), 7.23–7.28 (1H, m), 7.54–7.67 (2H, m), 8.01 (1H, s), 8.07–8.15 (1H, m), 8.66 (2H, s), 8.77 (2H, s), 12.22 (1H, s)

MASS (m/z): 272 (M$^+$+1 of free compound)

(6) 2-[3-(2-Acetylpyrrol-1-yl)benzoyl]guanidine hydrochloride mp: 87°–89° C.

IR (Nujol): 3100–3300 (br), 1690, 1630 cm$^{-1}$

NMR (DMSO-d$_6$, δ): 2.43 (3H, s), 6.68 (1H, dd, J=1.6 Hz, 3.1 Hz), 7.68–7.79 (2H, m), 7.99 (1H, d, J=8.1 Hz), 8.08 (1H, d, J=8.1 Hz), 8.49–8.70 (4H, m), 8.81 (2H, s), 12.38 (1H, s)

MASS (m/z): 271 (M$^+$+1 of free compound)

(7) 2-[3-(2-Cyanopyrrol-1-yl)benzoyl]guanidine hydrochloride mp 220°–221° C.

IR (Nujol): 3300, 3080, 1700, 1615, 1585 cm$^{-1}$

NMR (DMSO-d$_6$, δ): 6.52 (1H, dd, J=2.9 Hz, 3.9 Hz), 7.30 (1H, dd, J=1.5 Hz, 3.9 Hz), 7.75–7.88 (2H, m), 7.91–8.01 (2H, m), 8.18–8.26 (2H, m), 8.30–8.34 (1H, m), 8.65 (2H, s), 8.77 (2H, s), 12.42 (1H, s)

MASS (m/z): 254 (M$^+$+1 of free compound)

(8) 2-[3-(3-Cyanopyrrol-1-yl)benzoyl]guanidine hydrochloride mp: 259°–261° C.

IR (Nujol): 3350, 3100, 2230, 1700, 1610, 1590 cm$^{-1}$

NMR (DMSO-d$_6$, δ): 6.79 (1H, dd, J=1.5 Hz, 3.0 Hz), 7.75 (1H, dd, J=8.0 Hz, 8.0 Hz), 7.80–7.85 (1H, m), 7.99–8.10 (2H, m), 8.43–8.51 (2H, m), 8.56 (2H, s), 8.75 (2H, s), 12.35 (1H, s)

MASS (m/z): 254 (M$^+$+1 of free compound)

(9) 2-[4-n-Butyl-3-(2-cyanopyrrol-1-yl)benzoyl]guanidine hydrochloride mp: 193°–194° C.

IR (Nujol): 3260, 3120, 2220, 1710, 1610 cm$^{-1}$

NMR (DMSO-d$_6$, δ) 0.76 (3H, t, J=7.2 Hz), 1.05–1.27 (2H, m), 1.30–1.45 (2H, m), 2.39–2.55 (2H, m), 6.48 (1H, dd, J=2.7 Hz, 4.0 Hz), 7.24 (1H, dd, J=1.6 Hz, 4.0 Hz), 7.44 (1H, dd, J=1.6 Hz, 2.7 Hz), 7.74 (1H, d, J=8.1 Hz), 7.08 (1H, d, J=1.8 Hz), 8.29 (1H, dd, J=1.8 Hz, 8.1 Hz), 8.47–8.75 (4H, m), 12.10 (1H, s)

MASS (m/z): 310 (M$^+$+1 of free compound)

(10) 2-[4-n-Butyl-3-(pyrrol-1-yl)benzoyl]guanidine hydrochloride mp: 188°–189° C.

IR (Nujol): 3370, 3260, 1700, 1670, 1610 cm$^{-1}$

NMR (DMSO-d$_6$, δ) 0.77 (3H, t, J=7.1 Hz), 1.06–1.45 (4H, m), 2.50–2.65 (2H, m), 6.24–6.28 (2H, m), 6.98–7.03 (2H, m), 7.61 (1H, d, J=8.1 Hz), 7.97 (1H, s), 8.12 (1H, d, J=8.1 Hz), 8.64 (2H, s), 8.75 (2H, s), 12.17 (1H, s)

MASS (m/z): 285 (M$^+$+1 of free compound)

(11) 2-[4-Methyl-3-(pyrrol-1-yl)benzoyl]guanidine hydrochloride mp: 251°–252° C.

IR (Nujol): 3100, 1690, 1610 cm$^{-1}$

NMR (DMSO-d$_6$, δ): 2.30 (3H, s), 6.24–6.30 (2H, m), 7.05–7.11 (2H, m), 7.60 (1H, d, J=8.1 Hz), 7.98 (1H, d, J=1.8 Hz), 8.05 (1H, dd, J=1.8 Hz, 8.1 Hz), 8.59 (2H, s), 8.71 (2H, s), 12.11 (1H, s)

MASS (m/z): 243 (M$^+$+1 of free compound)

(12) 2-[5-Cyano-3-(pyrrol-1-yl)benzoyl]guanidine hydrochloride mp: 267°–268° C. (dec.)

IR (Nujol): 3400, 3250, 3130, 2230, 1700, 1610 cm$^{-1}$

NMR (DMSO-d$_6$, δ): 6.33–6.38 (2H, m), 7.72–7.78 (2H, m), 8.25 (1H, s), 8.50 (1H, s), 8.65 (2H, s), 8.72 (1H, s), 8.79 (2H, s), 12.62 (1H, s)

MASS (m/z): 254 (M$^+$+1 of free compound)

EXAMPLE 17

Conc. sulfuric acid (0.42 ml) was added to a mixture of 2-[3-(2-cyanopyrrol-1-yl)benzoyl]guanidine (2.0 g) and methanol (20 ml), and the mixture was stirred for 30 minutes at ambient temperature. To the mixture was added ethyl acetate (20 ml), and the isolated precipitate was collected by filtration. The precipitate was recrystallized from methanol-water to give 2-[3-(2-cyanopyrrol-1-yl) benzoyl]guanidine hemisulfate (1.53 g).

mp 170°–171° C.

IR (Nujol): 3300, 3110, 2220, 1720, 1690, 1610, 1100 cm$^{-1}$

NMR (DMSO-d$_6$, δ): 6.48 (1H, dd, J=2.8 Hz, 3.9 Hz), 7.00–8.40 (4H, br), 7.27 (1H, dd, J=1.6 Hz, 3.9 Hz), 7.61 (1H, dd, J=1.6 Hz, 2.8 Hz), 7.66–7.84 (2H, m), 8.07–8.14 (2H, m)

EXAMPLE 18

A solution of fumaric acid (0.46 g) in methanol (10 ml) was added to a solution of 2-[3-(2-cyanopyrrol-1-yl)benzoyl]guanidine (1.0 g) in methanol (10 ml) and the whole was stirred for 1 hour at ambient temperature. The isolated precipitate was collected by filtration and the precipitate was recrystallized from methanol-water to give 2-[3-(2-cyanopyrrol-1-yl)benzoyl]guanidine fumarate (1.03 g).

mp: 216°–217° C.

IR (Nujol): 3360, 3130, 2220, 1730, 1705, 1610 cm$^{-1}$

NMR (DMSO-d$_6$, δ): 6.46 (1H, dd, J=2.8 Hz, 3.9 Hz), 6.55–8.60 (4H, br), 6.61 (2H, s), 7.24 (1H, dd, J=1.6 Hz, 3.9 Hz), 7.57 (1H, dd, J=1.6 Hz, 2.8 Hz), 7.61–7.71 (2H, m), 8.11–8.19 (2H, m)

EXAMPLE 19

The following compounds were obtained according to similar manners to those of Examples 6, 17 and 18.

(1) 2-[3-(2-Cyanopyrrol-1-yl)benzoyl]guanidine hemicitrate mp: 158°–160° C.

IR (Nujol): 3330, 2220, 1700, 1610, 1590 cm$^{-1}$

NMR (DMSO-d$_6$, δ): 2.55–2.77 (2H, m), 6.47 (1H, dd, J=2.8 Hz, 3.9 Hz), 6.77–8.60 (4H, br), 7.24 (1H, dd, J=1.6 Hz, 3.9 Hz), 7.56 (1H, dd, J=1.6 Hz, 2.8 Hz), 7.59–7.75 (2H, m), 8.10–8.19 (2H, m)

(2) 2-[3-(2-Cyanopyrrol-1-yl)benzoyl]guanidine maleate mp: 211°–213° C.

IR (Nujol): 3400, 3250, 3100, 2220, 1705, 1685 cm$^{-1}$

NMR (DMSO-d$_6$, δ): 6.10 (2H, s), 6.51 (1H, dd, J=2.8 Hz, 3.9 Hz), 7.29 (1H, dd, J=1.6 Hz, 3.9 Hz), 7.62 (1H, dd, J=1.6 Hz, 2.8 Hz), 7.80 (1H, dd, J=8.2 Hz, 8.2 Hz), 7.85–7.94 (1H, m), 8.04–8.12 (2H, m), 8.19 (4H, s)

EXAMPLE 20

Methanesulfonic acid (0.5 ml) was added to a solution of 2-[3-(2-cyanopyrrol-1-yl)-5-(diaminomethyleneaminocarbonyl)benzoyl]guanidine (0.8 g) in methanol (16 ml) and the whole was stirred for 1 hour at ambient temperature. The isolated precipitate was collected by filtration and recrystallized from water to give 2-[3-(2-cyanopyrrol-1-yl)-5-(diaminomethyleneaminocarbonyl)benzoyl]guanidine dimethanesulfonate (0.65 g).

mp: 250°–251° C.

IR (Nujol): 3350, 3100, 2220, 1725, 1600, 1210, 1050 cm$^{-1}$

NMR (DMSO-d$_6$, δ): 2.43 (6H, s), 6.57 (1H, dd, J=2.9 Hz, 3.9 Hz), 7.36 (1H, dd, J=1.6 Hz, 3.9 Hz), 7.77 (1H, dd, J=1.6 Hz, 2.9 Hz), 8.30–8.80 (4H, m), 8.41 (2H, s), 8.55 (1H, s), 11.67 (2H, s)

MASS (m/z): 339 (M$^+$+1 of free compound)

EXAMPLE 21

The following compounds were obtained according to a similar manner to that of Example 20.

(1) 2-[3-(2-Cyanopyrrol-1-yl)benzoyl]guanidine methanesulfonate.

mp: 200°–201° C.

IR (Nujol) 3350, 3100, 2220, 1720, 1585, 1165, 1045 cm$^{-1}$

NMR (DMSO-d$_6$, δ): 2.36 (3H, s), 6.49–6.55 (1H, m), 7.27–7.33 (1H, m), 7.64–7.67 (1H, m), 7.84 (1H, dd, J=7.7 Hz, 7.7 Hz), 7.96 (1H, d, J=7.7 Hz), 8.00–8.10 (2H, m), 8.20–8.60 (4H, m), 11.42 (1H, s)

(2) 2-[3-(Pyrrol-1-yl)benzoyl]guanidine methanesulfonate mp: 216° C.

IR (Nujol): 3350, 3150, 1700, 1695, 1685, 1180, 1050 cm$^{-1}$

NMR (DMSO-d$_6$, δ): 2.38 (3H, s), 6.31–6.36 (2H, m), 7.45–7.50 (2H, m), 7.69 (1H, dd, J=7.8 Hz, 7.8 Hz), 7.79 (1H, d, J=7.8 Hz), 7.95 (1H, d, J=7.8 Hz), 8.07 (1H, s), 8.40 (4H, s), 11.39 (1H, s)

EXAMPLE 22

To a solution of 2-[3-nitro-5-(pyrrol-1-yl)benzoyl]guanidine (0.3 g) in a mixture of methanol (10 ml) and tetrahydrofuran (5 ml) was added 10% palladium-charcoal (50% in water) and the whole was hydrogenated at ambient temperature under an atmospheric pressure. The catalyst was filtered off and the filtrate was evaporated in vacuo. The residue was dissolved in ethanol and treated with slight excess 4N-hydrogen chloride in ethyl acetate to afford 2-[3-amino-5-(pyrrol-1-yl)benzoyl]guanidine dihydrochloride (310 mg).

mp: 269°–270° C. (dec.)

IR (Nujol): 3340, 1685, 1355, 715 cm$^{-1}$

NMR (DMSO-d$_6$, δ): 6.29–6.31 (2H, m), 7.37–7.41 (2H, m), 7.52–7.56 (2H, m), 8.00–8.05 (1H, m), 8.65 (2H, br), 8.88 (2H, br), 12.33 (1H, br)

MASS (m/z): 244 (M+1)

EXAMPLE 23

10% Palladium-carbon (0.2 g) was added to a mixture of 2-[3-(2-benzyloxycarbonylpyrrol-1-yl)benzoyl]guanidine (1.2 g) in methanol and the mixture was hydrogenated at ambient temperature under an atmospheric pressure. After the mixture was added to water, and the mixture was adjusted to pH 10 with potassium carbonate. The catalyst was removed by filtration and the filtrate was evaporated in vacuo. The residue was dissolved in a mixture of water and ethyl acetate and the separated aqueous layer was adjusted to pH 5 with 6N-hydrochloric acid. The isolated precipitate was collected by filtration and the precipitate was recrystallized from a mixture of methanol, dioxane and diisopropyl ether to give 2-[3-(2-carboxypyrrol-1-yl) benzoyl]guanidine (0.41 g).

mp: 213° C. (dec.)

IR (Nujol): 3270, 1690 cm$^{-1}$

NMR (DMSO-d$_6$, δ): 6.15–8.50 (4H, m), 6.29 (1H, dd, J=2.7 Hz, 3.8 Hz), 6.99 (1H, dd, J=1.8 Hz, 3.8 Hz), 7.17 (1H, dd, J=1.8 Hz, 2.7 Hz), 7.36–7.51 (2H, m), 7.97–8.09 (2H, m)

MASS (m/z): 273 (M$^+$+1)

EXAMPLE 24

Methyl 3-(3-trifluoromethylsulfonylaminophenyl)-benzoate (1.7 g) was added to the mixture of guanidine hydrochloride (2.26 g) and 28% methanolic sodium methoxide (4.1 ml) in N,N-dimethylformamide (17 ml) and the reaction mixture was stirred for 6 hours at ambient temperature. After evaporating the solvent, the residue was poured into the mixture of ethyl acetate (50 ml) and water (50 ml). The mixture was adjusted to pH 6.2 with 10% hydrochloric acid. The crystalline product was collected by filtration, washed successively with water and methanol and dried in vacuo to afford 2-[3-(3-trifluoromethylsulfonylaminophenyl) benzoyl]guanidine (0.28 g).

mp: 259°–260° C. (dec.)

IR (Nujol): 3375, 3250, 1705, 1010 cm$^{-1}$

NMR (DMSO-d$_6$, δ): 7.04–7.32 (4H, m), 7.67 (1H, dd, J=8.0 Hz, 7.5 Hz), 7.87–7.93 (2H, m), 8.12 (1H, s), 8.23 (4H, s)

(+) APCI MASS (m/z): 387 [M+H]$^+$

EXAMPLE 25

The following compounds were obtained according to similar manners to those of Examples 1, 3, 8, 10, 14 and 24.

(1) 2-[2-Methoxy-5-(pyrrol-1-yl)benzoyl]guanidine
mp: 208°–209° C.
IR (Nujol): 3400, 1662, 1590 cm$^{-1}$
NMR (DMSO-d$_6$, δ): 3.75 (3H, s), 6.10–8.30 (4H, br), 6.18–6.24 (2H, m), 7.03 (1H, d, J=8.6 Hz), 7.18–7.24 (2H, m), 7.38–7.51 (2H, m)

(2) 2-[2-Hydroxy-5-(pyrrol-1-yl)benzoyl]guanidine
mp: 191°–193° C.
IR (Nujol): 3370, 3180, 1668, 1610 cm$^{-1}$
NMR (DMSO-d$_6$, δ): 6.18–6.24 (2H, m), 6.70–8.90 (4H, br), 6.87 (1H, d, J=8.7 Hz), 7.14–7.20 (2H, m), 7.48 (1H, dd, J=3.0 Hz, 8.7 Hz), 7.86 (1H, d, J=3.0 Hz), 14.75 (1H, s)
(+) APCI MASS (m/z): 245 [M+H]$^+$
Elemental Analysis Calcd. for C$_{12}$H$_{12}$N$_4$O$_2$: C 59.01, H 4.95, N 22.94 Found C 59.16, H 5.04, N 22.59

(3) 2-[2-Nitro-5-(pyrrol-1-yl)benzoyl]guanidine
mp: 212°–213° C.
IR (Nujol): 3420, 1655, 1600, 1585, 1355 cm$^{-1}$
NMR (DMSO-d$_6$, δ): 6.20–8.50 (4H, br), 6.32–6.38 (2H, m), 7.51–7.57 (2H, m), 7.76 (1H, dd, J=2.5 Hz, 8.7 Hz), 7.83 (1H, d, J=2.5 Hz), 7.95 (1H, d, J=8.7 Hz)

(4) 2-[3-[2-((E)-1-Hydroxyiminoethyl)pyrrol-1-yl]benzoyl]guanidine
mp: 210°–211° C.
IR (Nujol): 3450, 3380, 1655, 1610 cm$^{-1}$
NMR (DMSO-d$_6$, δ): 2.09 (3H, s), 6.40–8.30 (4H, br), 6.53 (1H, dd, J=1.6 Hz, 2.9 Hz), 7.31–7.36 (1H, m), 7.48 (1H, dd, J=7.8 Hz, 7.8 Hz), 7.61–7.65 (1H, m), 7.65–7.72 (1H, m), 7.95 (1H, d, J=7.8 Hz), 8.18 (1H, s), 10.56 (1H, s)

(+) APCI MASS (m/z): 286 [M+H]$^+$
Elemental Analysis Calcd. for C$_{14}$H$_{15}$N$_5$O$_2$: C 58.94, H 5.30, N 24.55 Found: C 58.90, H 5.45, N 24.27

(5) 2-[3-[2-((Z)-1-Hydroxyiminoethyl)pyrrol-1-yl]benzoyl]guanidine
mp: 195°–197° C. (dec.)
IR (Nujol): 3360, 1600 cm$^{-1}$
NMR (DMSO-d$_6$, δ): 2.11 (3H, s), 6.40–6.84 (4H, br), 6.72 (1H, dd, J=1.5 Hz, 2.9 Hz), 7.34–7.39 (1H, m), 7.50 (1H, dd, J=7.8 Hz, 7.8 Hz), 7.64–7.71 (1H, m), 7.95–8.04 (2H, m), 8.17 (1H, m)

(6) 2-[3-(2-Methoxyiminomethylpyrrol-1-yl)benzoyl]guanidine methanesulfonate
mp: 162°–164° C.
IR (Nujol): 3350, 1715, 1695, 1170, 1045 cm$^{-1}$
NMR (DMSO-d$_6$, δ): 2.39 (3H, s), 3.70 and 3.93 (total 3H, each s), 6.35–6.46 (1H, m), 6.71–6.75 and 7.21–7.29 (total 2H, each m), 7.10 and 7.92 (total 1H, each s), 7.72–8.06 (4H, m), 8.38 (2H, s), 8.52 (2H, s), 11.37 (1H, s)
Elemental Analysis Calcd. for C$_{14}$H$_{15}$N$_5$O$_2$.CH$_4$O$_3$S: C 47.24, H 5.02, N 18.36 Found: C 47.31, H 4.73, N 18.07

(7) 2-[3-[2-((E)-2-Carboxyethenyl)pyrrol-1-yl]benzoyl]guanidine
mp: 204°–206° C.
IR (Nujol): 3340, 1700, 1663, 1618 cm$^{-1}$
NMR (DMSO-d$_6$, δ): 6.09 (1H, d, J=15.7 Hz), 6.30–8.40 (4H, br), 6.33–6.39 (1H, m), 6.97–7.02 (1H, m), 7.17 (1H, d, J=15.7 Hz), 7.20–7.25 (1H, m), 7.41–7.49 (1H, m), 7.59 (1H, dd, J=7.7 Hz, 7.7 Hz), 8.01 (1H, s), 8.16 (1H, d, J=7.7 Hz)
(+) APCI MASS (m/z): 299 [M+H]$^+$ (8) 2-[3-[2-(2-Carboxyethyl)pyrrol-1-yl]benzoyl]guanidine
mp: 221° C.
IR (Nujol): 3470, 3380, 1695, 1585 cm$^{-1}$
NMR (DMSO-d$_6$, δ): 2.43 (2H, t, J=7.0 Hz), 2.71 (2H, t, J=7.0 Hz), 5.98–6.03 (1H, m), 6.07–6.15 (1H, m), 6.30–8.40 (4H, m), 6.79–6.86 (1H, m), 7.41–7.58 (2H, m), 8.00–8.10 (2H, m)
(+) APCI MASS (m/z): 301 [M+H]$^+$
Elemental Analysis Calcd. for C$_{15}$H$_{16}$N$_4$O$_3$: C 59.99, H 5.37, N 18.66 Found: C 59.79, H 5.49, N 18.38

(9) 2-[5-(Pyrrol-1-yl)-3-sulfamoylbenzoyl]guanidine
mp: 173°–174° C.
IR (Nujol): 3350, 3230, 1628, 1365 cm$^{-1}$
NMR (DMSO-d$_6$, δ): 6.32–6.38 (2H, m), 6.40–8.70 (4H, br), 7.35–7.41 (2H, m), 7.46 (2H, s), 8.00–8.05 (1H, m), 8.31–8.36 (1H, m), 8.37–8.42 (1H, m)

(10) 2-[3-(Pyrrol-1-yl)-5-(1H-tetrazol-5-yl)benzoyl]guanidine
mp: ≧270° C.
IR (Nujol): 3350, 3100, 1700, 1650, 1597 cm$^{-1}$
NMR (DMSO-d$_6$, δ): 6.32–6.38 (2H, m), 7.15–8.50 (4H, br), 7.42–7.48 (2H, m), 8.18–8.22 (1H, m), 8.27–8.32 (1H, m), 8.56–8.60 (1H, m)
(+) APCI MASS (m/z): 297 [M+H]$^+$
Elemental Analysis Calcd. for C$_{13}$H$_{12}$N$_8$O: C 52.70, H 4.08, N 37.82 Found: C 52.60, H 3.98, N 37.46

(11) 2-[4-(2-Hydroxyethoxy)-3-(pyrrol-1-yl)benzoyl]guanidine
mp: 182°–185° C.
IR (Nujol): 3350, 1628, 1600 cm$^{-1}$
NMR (DMSO-d$_6$, δ): 3.65–3.77 (2H, m), 4.13 (2H, t, J=4.9 Hz), 4.86 (1H, t, J=5.2 Hz), 6.16–6.22 (2H, m), 6.40–8.30 (4H, br), 7.10–7.15 (2H, m), 7.19 (1H, d, J=8.6 Hz), 7.96 (1H, dd, J=2.1 Hz, 8.6 Hz), 8.01 (1H, d, J=2.1 Hz)

(12) 2-[4-Benzyloxy-3-(pyrrol-1-yl)benzoyl]guanidine
mp: 150°–153° C.

IR (Nujol): 3320, 1630, 1600 cm$^{-1}$

NMR (DMSO-d$_6$, δ): 5.21 (2H, s), 6.16–6.24 (2H, m), 6.30–6.84 (4H, br), 7.02–7.08 (2H, m), 7.27–7.47 (6H, m), 7.94–8.06 (2H, m)

(13) 2-[4-Methoxy-3-(pyrrol-1-yl)benzoyl]guanidine mp: 155°–156° C.

IR (Nujol): 3450, 3320, 1660, 1633, 1595 cm$^{-1}$

NMR (DMSO-d$_6$, δ): 3.85 (3H, s), 6.16–6.22 (2H, m), 6.30–8.30 (4H, br), 6.96–7.02 (2H, m), 7.19 (1H, d, J=9.2 Hz), 7.96–8.06 (2H, m)

(14) 2-[4-Carboxymethoxy-3-(pyrrol-1-yl)benzoyl]guanidine mp: 250°–253° C.

IR (Nujol): 3300, 1708, 1675, 1600 (br) cm$^{-1}$

NMR (DMSO-d$_6$, δ): 4.64 (2H, s), 6.16–6.23 (2H, m), 6.40–9.40 (4H, br), 6.98 (1H, d, J=8.8 Hz), 7.17–7.23 (2H, m), 7.90 (1H, dd, J=2.0 Hz, 8.8 Hz), 8.01 (1H, d, J=2.0 Hz)

(+) APCI MASS (m/z): 303 [M+H]$^+$

(15) 2-[3-Dimethylcarbamoyl-5-(pyrrol-1-yl)benzoyl]guanidine methanesulfonate mp: 203°–204° C.

IR (Nujol): 3350, 3280, 1710, 1630, 1590 cm$^{-1}$

NMR (DMSO-d$_6$, δ): 2.42 (3H, s), 2.95 (3H, s), 3.04 (3H, s), 6.3–6.4 (2H, m), 7.5–7.6 (2H, m), 7.75 (1H, s), 7.98 (1H, s), 8.13 (1H, t, J=1.8 Hz), 8.42 (2H, br s), 8.56 (2H, br s), 11.48 (1H, s)

(+) APCI MASS (m/z): 300 [M of free compound+H]$^+$

Elemental Analysis Calcd. for $C_{15}H_{17}N_5O_2 \cdot CH_4O_3S$: C 48.60, H 5.35, N 17.71 Found: C 48.27, H 5.32, N 17.47

(16) 2-[4-Acetylaminomethyl-3-(pyrrol-1-yl)benzoyl]guanidine mp: 183°–185° C.

IR (Nujol): 3400, 3320, 3180, 1640, 1590 cm$^{-1}$

NMR (DMSO-d$_6$, δ): 1.87 (3H, s), 4.12 (2H, d, J=5.6 Hz), 6.21–6.27 (2H, m), 6.93–6.99 (2H, m), 7.41 (1H, d, J=8.0 Hz), 7.98 (1H, s), 8.02 (1H, d, J=8.0 Hz), 8.28 (1H, t, J=5.6 Hz)

(17) 8-(Diaminomethyleneaminocarbonyl)-1-dimethylaminomethyl-4,4-dimethyl-4H-pyrrolo[2,1-c][1,4]benzoxazine mp: 182°–186° C.

IR (Nujol): 3400, 1660, 1600 cm$^{-1}$

NMR (DMSO-d$_6$, δ): 1.53 (6H, s), 2.29 (6H, s), 3.37 (2H, s), 6.01 (1H, d, J=3.4 Hz), 6.15 (1H, d, J=3.4 Hz), 6.30–8.40 (4H, br), 6.99 (1H, d, J=8.4 Hz), 7.86 (1H, dd, J=1.7 Hz, 8.4 Hz), 8.75 (1H, d, J=1.7 Hz)

(18) 2-[4-(Pyrrol-1-yl)benzoyl]guanidine mp: 184°–186° C.

IR (Nujol): 3300, 1595 cm$^{-1}$

NMR (DMSO-d$_6$, δ): 6.10–8.40 (4H, br), 6.26–6.32 (2H, m), 7.41–7.47 (2H, m), 7.59 (2H, d, J=8.8 Hz), 8.13 (2H, d, J=8.8 Hz)

(19) 2-[3-[(Pyrrol-1-yl)methyl]benzoyl]guanidine mp: 165°–166° C.

IR (Nujol): 3430, 3280, 1647, 1600 cm$^{-1}$

NMR (DMSO-d$_6$, δ): 5.11 (2H, s), 5.99–6.05 (2H, m), 6.20–8.40 (4H, br), 6.76–6.82 (2H, m), 7.22 (1H, d, J=7.5 Hz), 7.33 (1H, dd, J=7.5 Hz, 7.5 Hz), 7.92 (1H, s), 7.98 (1H, d, J7.5 Hz)

(20) 2-[3-(Pyrazol-3-yl)benzoyl]guanidine mp: 228°–230° C.

IR (Nujol): 3440, 3310, 3130, 1690 cm$^{-1}$

NMR (DMSO-d$_6$, δ): 6.40–8.80 (4H, br), 6.68 (1H, s), 7.41 (1H, dd, J=7.2 Hz, 7.2 Hz), 7.80 (1H, s), 7.85 (1H, d, J=7.2 Hz), 7.98 (1H, d, J=7.2 Hz), 8.53 (1H, s), 12.90 (1H, s)

(21) 2-[3-(Pyrimidin-4-yl)benzoyl]guanidine mp: 173°–175° C.

IR (Nujol): 3320, 3150, 1680, 1605, 1575 cm$^{-1}$

NMR (DMSO-d$_6$, δ): 6.20–8.70 (4H, br), 7.59 (1H, dd, J=7.7 Hz, 7.7 Hz), 8.10 (1H, d, J=5.4 Hz), 8.20–8.30 (2H, m), 8.86–8.95 (2H, m), 9.28 (1H, s)

(22) 2-[3-(Pyridin-2-yl)benzoyl]guanidine mp: 190°–191° C.

IR (Nujol): 3310, 3140, 1670, 1605, 1585, 1570 cm$^{-1}$

NMR (DMSO-d$_6$, δ): 6.30–8.60 (4H, br), 7.31–7.43 (1H, m), 7.51 (1H, dd, J=7.7 Hz, 7.7 Hz), 7.83–7.99 (2H, m), 8.08–8.18 (2H, m), 8.65–8.73 (1H, m), 8.78–8.84 (1H, m)

(23) 2-[3-(Pyridin-3-yl)benzoyl]guanidine mp: 182°–185° C.

IR (Nujol): 3430, 3290, 1690, 1670, 1625 cm$^{-1}$

NMR (DMSO-d$_6$, δ): 6.30–8.60 (4H, br), 7.46–7.58 (2H, m), 7.76–7.83 (1H, m), 8.02–8.15 (2H, m), 8.35–8.41 (1H, m), 8.56–8.62 (1H, m), 8.85–8.89 (1H, m)

(24) 2-[3-(5-Aminopyrazol-1-yl)benzoyl]guanidine mp: 140°–143° C.

IR (Nujol): 3320, 3180, 1645 cm$^{-1}$

NMR (DMSO-d$_6$, δ): 5.30 (2H, s), 5.48 (1H, d, J=1.8 Hz), 6.20–8.60 (4H, br), 7.29 (1H, d, J=1.8 Hz), 7.47 (1H, dd, J=7.8 Hz, 7.8 Hz), 7.61–7.69 (1H, m), 7.95–8.02 (1H, m), 8.27–8.32 (1H, m)

(25) 2-[3-(1H-Tetrazol-5-yl)benzoyl]guanidine mp: >300° C.

IR (Nujol): 3300, 3100, 1700, 1670, 1610 cm$^{-1}$

NMR (D$_2$O+NaOD, δ): 7.56 (1H, dd, J=7.8 Hz, 7.8 Hz), 7.98 (1H, d, J=7.8 Hz), 8.12 (1H, d, J=7.8 Hz), 8.50 (1H, s)

(+) APCI MASS (m/z): 232 [M+H]$^+$

(26) 2-[3-(3-Cyano-1,5-dimethylpyrrol-2-yl)benzoyl]guanidine mp: 112°–124° C.

IR (Nujol): 3320, 2220, 1662, 1640, 1610, 1590 cm$^{-1}$

NMR (DMSO-d$_6$, δ): 2.26 (3H, s), 3.45 (3H, s), 6.20–8.40 (4H, m), 7.50–7.62 (2H, m), 8.10–8.20 (2H, m)

(27) 2-[2-(Pyrrol-1-yl)isonicotinoyl]guanidine mp: 165°–169° C.

IR (Nujol): 3440, 3350, 3070, 1685, 1625, 1605 cm$^{-1}$

NMR (DMSO-d$_6$, δ): 6.29–6.35 (2H, m), 6.50–8.90 (4H, br), 7.63–7.69 (2H, m), 7.71–7.77 (1H, m), 8.06 (1H, s), 8.45–8.52 (1H, m)

(28) 2-[[4-(Pyrrol-1-yl)pyridin-1-yl]carbonyl]guanidine mp: 176°–180° C.

IR (Nujol): 3320, 3100, 1663, 1584 cm$^{-1}$

NMR (DMSO-d$_6$, δ): 6.20–8.70 (4H, br), 6.34–6.40 (2H, m), 7.55–7.61 (2H, m), 7.70 (1H, dd, J=2.2 Hz, 5.4 Hz), 8.20 (1H, d, J=2.2 Hz), 8.58 (1H, d, J=5.4 Hz)

(29) 2-[3-(3-Methylphenyl)benzoyl]guanidine hydrochloride mp: 168°–169° C.

IR (Nujol): 1690, 1300, 1250 cm$^{-1}$

NMR (DMSO-d$_6$, δ): 2.40 (3H, s), 7.24 (1H, d, J=7.4 Hz), 7.39 (1H, dd, J=7.6 Hz, 7.6 Hz), 7.60–7.75 (3H, m), 7.95–8.15 (2H, m), 8.47 (1H, s), 8.63 (2H, br s), 8.89 (2H, br s), 12.30 (1H, s)

(+) APCI MASS (m/z): 254 [M of free compound+H]$^+$

(30) 2-[3-(2-Fluorophenyl)benzoyl]guanidine hydrochloride mp: 168°–169° C.

IR (Nujol): 3350, 3150, 1700, 1685, 1235 cm$^{-1}$

NMR (DMSO-d$_6$, δ): 7.3–7.55 (3H, m), 7.67–7.80 (2H, m), 7.90–7.94 (1H, m), 8.17 (1H, d, J=7.9 Hz), 8.30 (1H, s), 8.63 (2H, br s), 8.81 (2H, br s)

(+) APCI MASS (m/z): 258 [M of free compound+H]$^+$

Elemental Analysis Calcd. for $C_{14}H_{12}FN_3O \cdot HCl$: C 56.55, H 4.54, N 14.13 Found: C 56.65, H 4.43, N 14.15

(31) 2-[3-(3-Nitrophenyl)benzoyl]guanidine hydrochloride
mp: 239°–240° C.
IR (Nujol): 3325, 1690, 1520, 1360 cm$^{-1}$
NMR (DMSO-d$_6$, δ): 7.7–7.9 (2H, m), 8.1–8.2 (2H, m), 8.2–8.3 (1H, m), 8.3–8.4 (1H, m), 8.4–8.9 (6H, m), 12.31 (1H, s)
(+) APCI MASS (m/z): 285 [M of free compound+H]$^+$
(32) 2-[3-(2-Nitrophenyl)benzoyl]guanidine hydrochloride
mp: 206°–208° C.
IR (Nujol): 3350, 1700, 1590, 1520, 1230 cm$^{-1}$
NMR (DMSO-d$_6$, δ): 7.67–7.88 (5H, m), 8.05–8.23 (3H, m), 8.59 (2H, br s), 8.73 (2H, br s), 12.17 (1H, s)
(+) APCI MASS (m/z): 285 [M of free compound+H]$^+$
(33) 2-[3-(3-Cyanophenyl)benzoyl]guanidine hydrochloride
mp: 268° C. (dec.)
IR (Nujol): 3350, 2230, 1700, 1560 cm$^{-1}$
NMR (DMSO-d$_6$, δ): 7.67–7.77 (2H, m), 7.90 (1H, d, J=7.8 Hz), 8.12 (2H, d, J=7.8 Hz), 8.27 (1H, d, J=7.8 Hz), 8.40 (1H, s), 8.59 (1H, s), 8.61 (2H, br s), 8.85 (2H, br s), 12.40 (1H, s)
(+) APCI MASS (m/z): 265 [M of free compound+H]$^+$
(34) 2-[3-(2-Chlorophenyl)benzoyl]guanidine hydrochloride
mp: 191°–192° C.
IR (Nujol): 3200, 1690, 1560, 1230 cm$^{-1}$
NMR (DMSO-d$_6$, δ): 7.44–7.74 (5H, m), 7.82 (1H, ddd, J=7.8 Hz, 1.4 Hz, 1.4 Hz), 8.15–8.24 (2H, m), 8.65 (2H, br s), 8.80 (2H, br s), 12.20 (1H, s)
(+) APCI MASS (m/z): 274 [M of free compound+H]$^+$
Elemental Analysis Calcd. for C$_{14}$H$_{12}$ClN$_3$O.HCl: C 54.21, H 4.22, N 13.55 Found: C 54.11, H 4.24, N 13.42
(35) 2-[3-(3-Fluorophenyl)benzoyl]guanidine hydrochloride
mp: 214°–216° C.
IR (Nujol): 3100, 1690, 1270 cm$^{-1}$
NMR (DMSO-d$_6$, δ): 7.22–7.31 (1H, m), 7.49–7.84 (4H, m), 8.05–8.13 (2H, m), 8.54 (1H, s), 8.64 (2H, br s), 8.89 (2H, br s), 12.41 (1H, s)
(+) APCI MASS (m/z): 258 [M of free compound+H]$^+$
(36) 2-[3-(4-Fluorophenyl)benzoyl]guanidine hydrochloride
mp: 160°–162° C.
IR (Nujol): 3120, 1700, 1630, 1260 cm$^{-1}$
NMR (DMSO-d$_6$, δ): 7.29–7.38 (2H, m), 7.69 (1H, dd, J=7.8 Hz, 7.8 Hz), 7.90–8.09 (4H, m), 8.47 (1H, s), 8.61 (2H, br s), 8.86 (2H, br s), 12.34 (1H, s)
(+) APCI MASS (m/z): 258 [M of free compound+H]$^+$
(37) 2-[3-(3-Trifluoromethylphenyl)benzoyl]guanidine hydrochloride
mp: 179°–181° C.
IR (Nujol): 3300, 1690, 1640, 1150, 1110 cm$^{-1}$
NMR (DMSO-d$_6$, δ): 7.69–7.82 (3H, m), 8.09–8.15 (2H, m), 8.20–8.23 (2H, m), 8.55 (1H, s), 8.59 (2H, br s), 8.82 (2H, br s), 12.37 (1H, s)
(+) APCI MASS (m/z): 308 [M of free compound+H]$^+$
(38) 2-[3-[(E)-2-Carboxyethenyl]5-(pyrrol-1-yl)benzoyl]guanidine
mp: >250° C.
IR (Nujol): 3300, 1690, 1580 cm$^{-1}$
NMR (DMSO-d$_6$, δ): 6.2–6.4 (2H, m), 6.70 (1H, d, J=16.0 Hz), 7.4–7.5 (2H, m), 7.66 (1H, d, J=16.0 Hz), 8.0–8.2 (3H, m)
(+) APCI MASS (m/z): 299 [M+H]$^+$
(39) 2-[3-Trifluoromethylsulfonylamino-5-(pyrrol-1-yl)benzoyl]guanidine
mp: >250° C.
IR (Nujol): 3370, 1700, 1595 cm$^{-1}$
NMR (DMSO-d$_6$, δ): 6.2–6.3 (2H, m), 7.2–7.3 (2H, m), 7.4–7.5 (3H, m), 8.1–8.4 (4h, br s), 11.09 (1H, br s)
(+) APCI MASS (m/z): 376 [M+H]$^+$
(40) 2-[3-(Diethylaminoacetylamino)-5-(pyrrol-1-yl)benzoyl]guanidine dihydrochloride
mp: 188°–195° C.
IR (Nujol): 3200, 1700, 1590 cm$^{-1}$
NMR (DMSO-d$_6$, δ): 1.27 (6H, t, J=7.2 Hz), 3.2–3.4 (4H, m), 4.24 (2H, s), 6.3–6.4 (2H, m), 7.5–7.6 (2H, m), 8.15 (1H, s), 8.18 (1H, s), 8.38 (1H, s), 8.70 (2H, br s), 8.92 (2H, br s), 9.95 (1H, br s), 11.66 (1H, s), 12.57 (1H, s)
(+) APCI MASS (m/z): 357 [M of free compound+H]$^+$
(41) 2-[3-Morpholinoacetylamino)-5-(pyrrol-1-yl)benzoyl]guanidine dihydrochloride
mp: >250° C.
IR (Nujol): 3320, 1690, 1615, 1580 cm$^{-1}$
NMR (DMSO-d$_6$, δ): 3.1–3.6 (4H, m), 3.7–4.1 (4H, m), 4.27 (2H, s), 6.2–6.4 (2H, m), 7.5–7.6 (2H, m), 8.11 (1H, s), 8.16 (1H, s), 8.35 (1H, s), 8.64 (2H, br s), 8.90 (2H, br s), 10.70 (1H, br s), 11.43 (1H, s), 12.53 (1H, s)
(+) APCI MASS (m/z): 371 [M of free compound+H]$^+$
(42) 2-[3-Dimethylaminomethyl-5-(pyrrol-1-yl)benzoyl]guanidine dihydrochloride
mp: >250° C.
IR (Nujol): 3300, 1690, 1600 cm$^{-1}$
NMR (DMSO-d$_6$, δ): 2.75 (6H, s), 4.43 (2H, s), 6.3–6.4 (2H, m), 7.7–7.8 (2H, m), 8.02 (1H, s), 8.38 (1H, s), 8.60 (1H, s), 8.71 (1H, br s), 8.93 (1H, br s), 11.20 (1H, br s), 12.67 (1H, br s)
(+) APCI MASS (m/z): 286 [M of free compound+H]$^+$
(43) 2-[3-(2-Aminoethyl)-5-(pyrrol-1-yl)benzoyl]guanidine dihydrochloride
mp: 216°–218° C.
IR (Nujol): 3350, 1690, 1600 cm$^{-1}$
NMR (DMSO-d$_6$, δ): 2.9–3.3 (4H, m), 6.2–6.4 (2H, m), 7.6–7.7 (2H, m), 7.8–7.9 (2H, m), 8.0–8.3 (3H, m), 8.33 (1H, s), 8.72 (2H, br s), 8.95 (2H, br s), 12.60 (1H, s)
(+) APCI MASS (m/z): 272 [M of free compound+H]$^+$
(44) 2-[3-Hydroxyiminomethyl-5-(pyrrol-1-yl)benzoyl]guanidine
mp: 185°–187° C.
IR (Nujol): 3360, 3130, 1660, 1625, 1585 cm$^{-1}$
NMR (DMSO-d$_6$, δ): 6.2–6.4 (2H, m), 7.3–7.4 (2H, m), 7.7–8.3 (4H, m), 11.39 (1H, s)
(+) APCI MASS (m/z): 272 [M+H]$^+$
(45) 2-[3-Hydroxymethyl-5-(pyrrol-1-yl)benzoyl]guanidine
mp: 188°–189° C.
IR (Nujol): 3420, 3300, 3150, 1635, 1600 cm$^{-1}$
NMR (DMSO-d$_6$, δ): 4.5–4.7 (2H, m), 5.2–5.4 (1H, m), 6.2–6.3 (2H, m), 7.3–7.4 (2H, m), 7.5–7.6 (1H, s), 7.9–8.1 (2H, m)
(+) APCI MASS (m/z): 259 [M+H]$^+$
(46) 1-Cyano-8-(diaminomethyleneaminocarbonyl)-4,4-dimethyl-4H-pyrrolo[2,1-c][1,4]benzoxazine methanesulfonate
mp: 276°–278° C.
IR (Nujol): 3330, 3160, 3100, 2210, 1712, 1694, 1610, 1597, 1195, 1040 cm$^{-1}$
NMR (DMSO-d$_6$, δ): 1.64 (6H, s), 2.38 (3H, s), 6.47 (1H, d, J=4.0 Hz), 7.39 (1H, d, J=4.0 Hz), 7.41 (1H, d, J=8.6 Hz), 7.90 (1H, dd, J=2.0 Hz, 8.6 Hz), 8.39 (4H, s), 8.66 (1H, d, J=2.0 Hz), 11.31 (1H, s)
(+) APCI MASS (m/z): 310 [M of free compound+H]$^+$
Elemental Analysis Calcd. for C$_{16}$H$_{15}$N$_5$O$_2$.CH$_4$O$_3$S: C 50.36, H 4.72, N 17.27 Found: C 50.17, H 4.84, N 17.12
(47) 8-(Diaminomethyleneaminocarbonyl)-4H-pyrrolo[2,1-c][1,4]benzoxazine methane sulfonate
mp: 232°–233° C.
IR (Nujol): 3330, 1695, 1585, 1170, 1045 cm$^{-1}$ NMR (DMSO-d$_6$, δ): 2.42 (3H, s), 5.31 (2H, s), 6.11–6.17 (1H, m), 6.33–6.40 (1H, m), 7.28 (1H, d, J=8.5 Hz), 7.57–7.65 (1H, m), 7.71 (1H, dd, J=2.1 Hz, 8.5 Hz), 8.21 (1H, d, J=2.1 Hz), 8.42 (4H, s), 11.28 (1H, s)

(+) APCI MASS (m/z): 257 [M of free compound+H]$^+$

Elemental Analysis Calcd. for C$_{13}$H$_{12}$N$_4$O$_2$.CH$_4$O$_3$S: C 47.72, H 4.58, N 15.90 Found: C 47.80, H 4.59, N 15.79

(48) 2-[3-Hydroxymethyl-5-phenylbenzoyl]guanidine methanesulfonate mp: 129°–130° C.

IR (Nujol): 3350, 1690, 1170, 1040 cm$^{-1}$

NMR (DMSO-d$_6$, δ): 4.68 (2H, s), 7.40–7.60 (3H, m), 7.73–7.78 (2H, m), 7.90–7.95 (2H, m), 8.09 (1H, s), 8.3–8.7 (4H, br), 11.38 (1H, s)

(+) APCI MASS (m/z): 270 [M of free compound+H]$^+$

(49) 2-[3-Benzoylbenzoyl]guanidine methanesulfonate mp: 208°–210° C.

IR (Nujol): 3300, 1710, 1040, 700 cm$^{-1}$

NMR (DMSO-d$_6$, δ): 2.38 (3H, s), 7.56–7.85 (6H, m), 8.03–8.08 (1H, m), 8.22–8.30 (2H, m), 8.20–8.70 (4H, br), 11.45 (1H, s)

(+) APCI MASS (m/z): 268 [M of free compound+H]$^+$

(50) 2-[3-Trifluoromethylbenzoyl]guanidine hydrochloride mp: 156°–157° C.

IR (Nujol): 3400, 3200, 1715, 1700, 1690 cm$^{-1}$

NMR (DMSO-d$_6$, δ): 7.85 (1H, dd, J=7.8 Hz, 7.7 Hz), 8.09 (1H, d, J=7.8 Hz), 8.43 (1H, d, J=7.7 Hz), 8.48 (1H, s), 8.67 (2H, br s), 8.77 (2H, br s), 12.42 (1H, s)

(+) APCI MASS (m/z): 232 [M of free compound+H]$^+$

(51) 2-[3-(3-Chlorophenyl)benzoyl]guanidine methanesulfonate mp: 213°–214° C.

IR (Nujol): 3340, 3100, 1710, 1160 cm$^{-1}$

NMR (DMSO-d$_6$, δ): 2.40 (3H, s), 7.49–7.61 (2H, m), 7.68–7.79 (2H, m), 7.86 (1H, s), 7.97 (1H, d, J=7.9 Hz), 8.07 (1H, d, J=7.9 Hz), 8.22 (1H, s), 8.45 (4H, br s), 11.42 (1H, s)

(+) APCI MASS (m/z): 276 [M of free compound+H]$^+$

Elemental Analysis Calcd. for C$_{14}$H$_{12}$ClN$_3$O.CH$_3$SO$_3$H: C 48.72, H 4.36, N 11.36 Found: C 48.74, H 4.40, N 11.22

(52) 2-[3-(Furan-3-yl)benzoyl]guanidine methanesulfonate mp: 214°–216° C.

IR (Nujol): 3350, 3100, 1690, 1590, 1260 cm$^{-1}$

NMR (DMSO-d$_6$, δ): 2.42 (3H, s), 7.07 (1H, dd, J=1.6 Hz, 0.6 Hz), 7.63 (1H, dd, J=7.8 Hz, 7.8 Hz), 7.80–7.85 (2H, m), 7.97 (1H, d, J=7.8 Hz), 8.15 (1H, dd, J=1.6 Hz, 0.6 Hz), 8.34 (1H, s), 8.46 (4H, br s), 11.38 (1H, s)

(+) APCI MASS (m/z): 230 [M of free compound+H]$^+$

Elemental Analysis Calcd. for C$_{12}$H$_{11}$N$_3$O$_2$.CH$_3$SO$_3$H: C 47.99, H 4.65, N 12.92 Found: C 48.17, H 4.75, N 12.46

(53) 2-[3-Hydroxy-5-phenylbenzoyl]guanidine methanesulfonate mp: 287°–288° C.

IR (Nujol): 3300, 3150, 1700, 1600, 1340, 1150 cm$^{-1}$

NMR (DMSO-d$_6$, δ): 2.42 (3H, s), 7.36 (2H, ddd, J=7.8 Hz, 2.1 Hz, 2.1 Hz), 7.40–7.56 (3H, m), 7.65–7.73 (3H, m), 8.42 (4H, br s), 10.22 (1H, s), 11.27 (1H, s)

(+) APCI MASS (m/z): 256 (M of free compound+H]$^+$

(54) 2-[3-(2-Hydroxyethoxy)-5-phenylbenzoyl]guanidine methanesulfonate mp: 175°–176° C.

IR (Nujol): 3350, 3100, 1700, 1590, 1170 cm$^{-1}$

NMR (DMSO-d$_6$, δ): 2.43 (3H, s), 3.78 (2H, t, J=4.8 Hz), 4.19 (2H, t, J=4.8 Hz), 7.39–7.55 (5H, m), 7.76–7.80 (3H, m), 8.44 (4H, br s), 11.36 (1H, s)

(+) APCI MASS (m/z): 300 [M of free compound+H]$^+$

(55) 2-[3-(2-Cyanothiophen-3-yl)benzoyl]guanidine methanesulfonate mp: 188°–189° C.

IR (Nujol): 3320, 2200, 1710, 1050 cm$^{-1}$

NMR (DMSO-d$_6$, δ): 2.38 (3H, s), 7.68 (1H, d, J=5.1 Hz), 7.81 (1H, dd, J=7.8 Hz, 7.8 Hz), 8.00–8.15 (2H, m), 8.22 (1H, d, J=5.1 Hz), 8.24–8.26 (1H, m), 8.3–8.6 (4H, br s), 11.42 (1H, s)

(+) APCI MASS (m/z): 271 [M+H]$^+$

Elemental Analysis Calcd. for C$_{13}$H$_{10}$N$_4$OS.CH$_4$O$_3$S: C 45.89, H 3.85, N 15.29 Found: C 45.81, H 3.74, N 15.13

(56) 2-[3-(2-Cyanofuran-3-yl)benzoyl]guanidine methanesulfonate mp: 208° C. (dec.)

IR (Nujol): 3300, 2220, 1720, 1170 cm$^{-1}$

NMR (DMSO-d$_6$, δ): 2.37 (3H, s), 7.38 (1H, d, J=1.9 Hz), 7.81 (1H, dd, J=7.8 Hz, 7.8 Hz), 8.04 (1H, d, J=7.8 Hz), 8.11 (1H, d, J=7.8 Hz), 8.24 (1H, d, J=1.9 Hz), 8.28 (1H, dd, J1.7 Hz, 1.7 Hz), 8.43 (4H, br s), 11.44 (1H, s)

(+) APCI MASS (m/z): 255 [M+H]$^+$

(57) 2-[2-Hydroxy-3-(pyrrol-1-yl)benzoyl]guanidine methanesulfonate mp: 176°–177° C.

IR (Nujol): 3390, 3280, 1694, 1665, 1575, 1237, 1028 cm$^{-1}$

NMR (DMSO-d$_6$, δ): 2.36 (3H, s), 6.18–6.24 (2H, m), 6.99 (1H, dd, J=7.9 Hz, 7.9 Hz), 7.07–7.13 (2H, m), 7.40 (1H, dd, J=1.5 Hz, 7.9 Hz), 7.75 (1H, dd, J=1.5 Hz, 7.9 Hz), 7.80–8.60 (4H, br)

Elemental Analysis Calcd. for C$_{12}$H$_{12}$N$_4$O$_2$.CH$_4$O$_3$S: C 45.88, H 4.74, N 16.46 Found: C 46.04, H 4.83, N 16.48

(58) 6-(Diaminomethyleneaminocarbonyl)-4H-pyrrolo[2,1-c][1,4]benzoxazine methanesulfonate NMR (DMSO-d$_6$, δ): 2.35 (3H, s), 5.38 (2H, s), 6.15–6.20 (1H, m), 6.31–6.39 (1H, m), 7.25 (1H, dd, J=7.9 Hz, 7.9 Hz), 7.50–7.62 (2H, m), 7.98 (1H, dd, J=1.5 Hz, 7.9 Hz), 8.58 (4H, s), 11.05 (1H, s)

(59) 1-Cyano-6-(diaminomethyleneaminocarbonyl)-4H-pyrrolo[2,1-c][1,4]benzoxazine methanesulfonate NMR (DMSO-d$_6$, δ): 2.36 (3H, s), 5.42 (2H, s), 6.45 (1H, d, J=4.0 Hz), 7.34–7.44 (2H, m), 7.68 (1H, dd, J=1.4 Hz, 7.9 Hz), 8.20 (1H, dd, J=1.4 Hz, 7.9 Hz), 8.56 (4H, s), 11.18 (1H, s)

(60) 2-[4-Hydroxymethyl-3-(pyrrol-1-yl)benzoyl]guanidine methanesulfonate mp: 131°–133° C.

IR (Nujol): 3340, 3120, 1707, 1590, 1190, 1040 cm$^{-1}$

NMR (DMSO-d$_6$, δ): 2.40 (3H, s), 4.47 (2H, s), 6.25–6.31 (2H, m), 7.05–7.11 (2H, m), 7.80–7.90 (2H, m), 8.00 (1H, d, J=8.7 Hz), 8.22–8.70 (4H, br), 11.33 (1H, s)

EXAMPLE 26

The following compounds were obtained according to similar manners to those of Examples 6, 17 and 18.

(1) 2-[2-Methoxy-5-(pyrrol-1-yl)benzoyl]guanidine methanesulfonate mp: 197°–198° C.

IR (Nujol): 3290, 3130, 1710, 1180, 1050 cm$^{-1}$

NMR (DMSO-d$_6$, δ) 2.42 (3H, s), 3.98 (3H, s), 6.25–6.30 (2H, m), 7.31–7.39 (3H, m), 7.80–7.89 (2H, m), 8.65 (4H, s), 11.11 (1H, s)

Elemental Analysis Calcd. for C$_{13}$H$_{14}$N$_4$O$_2$.CH$_4$O$_3$S: C 47.45, H 5.12, N 15.81 Found: C 47.09, H 5.16, N 15.52

(2) 2-[5-(Pyrrol-1-yl)-3-sulfamoylbenzoyl]guanidine methanesulfonate mp: 240°–241° C.

IR (Nujol): 3300, 3150, 1718, 1695, 1585, 1335, 1165 cm$^{-1}$

NMR (DMSO-d$_6$, δ): 2.43 (3H, s), 6.37–6.43 (2H, m), 7.51–7.56 (2H, m), 7.65 (2H, s), 8.16 (1H, s), 8.25–8.31 (2H, m), 8.31–8.80 (4H, m), 11.64 (1H, s)

Elemental Analysis Calcd. for C$_{12}$H$_{13}$N$_5$O$_3$S.CH$_4$O$_3$S: C 38.70, H 4.25, N 17.36 Found: C 38.45, H 4.25, N 17.08

(3) 2-[4-Methoxy-3-(pyrrol-1-yl)benzoyl]guanidine methanesulfonate mp: 220°–221° C.

IR (Nujol): 3320, 3100, 1705, 1605, 1260, 1048 cm$^{-1}$

NMR (DMSO-d$_6$, δ): 2.38 (3H, s), 3.94 (3H, s), 6.22–6.28 (2H, m), 7.09–7.15 (2H, m), 7.44 (1H, d, J=8.7 Hz), 7.91 (1H, d, J=2.2 Hz), 7.97 (1H, dd, J=2.2 Hz, 8.7 Hz), 8.38 (4H, s), 11.19 (1H, s)

(+) APCI MASS (m/z): 259 [M of free compound+H]$^+$

Elemental Analysis Calcd. for C$_{13}$H$_{14}$N$_4$O$_2$.CH$_4$O$_3$S: C 47.45, H 5.12, N 15.81 Found: C 47.30, H 5.17, N 15.72

(4) 2-[4-Acetylaminomethyl-3-(pyrrol-1-yl)benzoyl]guanidine methanesulfonate mp: 193°–194° C.

IR (Nujol): 3370, 3270, 1705, 1648, 1175, 1050 cm$^{-1}$

NMR (DMSO-d$_6$, δ): 1.89 (3H, s), 2.37 (3H, s), 4.20 (2H, d, J=5.7 Hz), 6.26–6.34 (2H, m), 7.03–7.12 (2H, m), 7.61 (1H, d, J=8.2 Hz), 7.85 (1H, s), 7.97 (1H, d, J=8.2 Hz), 8.19–8.65 (5H, m), 11.30 (1H, s)

(+) APCI MASS (m/z): 300 (M of free compound+H)$^+$

Elemental Analysis Calcd. for C$_{15}$H$_{17}$N$_5$O$_2$.CH$_4$O$_3$S: C 48.60, H 5.35, N 17.71 Found: C 48.79, H 5.41, N 17.39

(5) 2-[3-(3-Cyano-1,5-dimethylpyrrol-2-yl)benzoyl]guanidine methanesulfonate mp: 230°–231° C.

IR (Nujol): 3330, 3080, 2220, 1700, 1650, 1600, 1170, 1050 cm$^{-1}$

NMR (DMSO-d$_6$, δ): 2.27 (3H, s), 2.34 (3H, s), 3.49 (3H, s), 6.40 (1H, s), 7.72–7.88 (2H, m), 7.95–8.08 (2H, m), 8.35 (4H, s), 11.32 (1H, s)

(+) APCI MASS (m/z): 282 [M of free compound+H]$^+$

Elemental Analysis Calcd. for C$_{15}$H$_{15}$N$_5$O.CH$_4$O$_3$S: C 50.92, H 5.07, N 18.56 Found: C 50.85, H 5.02, N 18.36

(6) 2-[3-Hydroxymethyl-5-(pyrrol-1-yl)benzoyl]guanidine isethionate mp: 154°–156° C.

IR (Nujol): 3350, 1700, 1590 cm$^{-1}$

NMR (DMSO-d$_6$, δ): 2.73 (2H, t, J=7.0 Hz), 3.67 (2H, t, J=7.0 Hz), 4.66 (2H, s), 6.3–6.4 (2H, m), 7.4–7.5 (2H, m), 7.7–8.0 (3H, m), 8.44 (4H, br s), 11.38 (1H, s)

(+) APCI MASS (m/z): 259 [M of free compound+H]$^+$

Elemental Analysis Calcd. for C$_{13}$H$_{14}$N$_4$O$_2$.C$_2$H$_6$O$_4$S: C 46.87, H 5.24, N 14.57 Found: C 46.63, H 5.32, N 14.45

(7) 2-[3-Hydroxyiminomethyl-5-(pyrrol-1-yl)benzoyl]guanidine methanesulfonate mp: 224°–226° C.

IR (Nujol): 3350, 3170, 1700, 1645, 1590 cm$^{-1}$

NMR (DMSO-d$_6$, δ): 2.42 (3H, s), 6.3–6.4 (2H, m), 7.5–7.6 (2H, m), 8.0–8.1 (3H, m), 8.31 (1H, s), 8.42 (4H, br s), 11.51 (1H, s), 11.64 (1H, s)

(+) APCI MASS (m/z): 272 [M of free compound+H]$^+$

Elemental Analysis Calcd. for C$_{13}$H$_{13}$N$_5$O$_2$.CH$_4$O$_3$S: C 45.77, H 4.66, N 19.06 Found: C 45.69, H 4.75, N 18.87

(8) 2-[2-Nitro-5-(pyrrol-1-yl)benzoyl]guanidine hydrochloride mp: 253°–254° C.

IR (Nujol): 3350, 3120, 1720, 1690, 1620, 1590, 1570, 1330 cm$^{-1}$

NMR (DMSO-D$_6$, δ): 6.38–6.44 (2H, m), 7.65–7.71 (2H, m), 8.06 (1H, dd, J=2.5 Hz, 9.0 Hz), 8.21 (1H, d, J=2.5 Hz), 8.31 (1H, d, J=9.0 Hz), 8.45 (2H, s), 8.74 (2H, s), 12.77 (1H, s)

(+) APCI MASS (m/z): 274 [M of free compound+H]$^+$

Elemental Analysis Calcd. for C$_{12}$H$_{11}$N$_5$O$_3$.HCl C 46.54, H 3.91, N 22.61 Found: C 46.24, H 3.90, N 22.27

(9) 2-[3-[2-((Z)-1-Hydroxyiminoethyl)pyrrol-1-yl]benzoyl]guanidine hydrochloride mp: 184°–186° C.

IR (Nujol): 3300, 1685 cm$^{-1}$

NMR (DMSO-d$_6$, δ): 2.26 (3H, s), 6.90–6.95 (1H, m), 7.65–7.77 (2H, m), 7.97–8.07 (2H, m), 8.36 (1H, s), 8.51 (1H, s), 8.65 (2H, s), 8.86 (2H, s), 12.46 (1H, s)

(+) APCI MASS (m/z): 286 [M of free compound+H]$^+$

(10) 2-[4-(2-Hydroxyethoxy)-3-(pyrrol-1-yl)benzoyl]guanidine hydrochloride mp: 140°–142° C.

IR (Nujol): 3330, 3150, 1707, 1685, 1600 cm$^{-1}$

NMR (DMSO-d$_6$, δ): 3.75 (2H, t, J=4.7 Hz), 4.24 (2H, t, J=4.7 Hz), 6.20–6.26 (2H, m), 7.33–7.39 (2H, m), 7.42 (1H, d, J=8.8 Hz), 8.05 (1H, dd, J=2.3 Hz, 8.8 Hz), 8.12 (1H, d, J=2.3 Hz), 8.51 (2H, s), 8.72 (2H, s), 12.06 (1H, s)

(+) APCI MASS (m/z): 289 [M of free compound+H]$^+$

(11) 8-(Diaminomethyleneaminocarbonyl)-1-dimethylaminomethyl-4,4-dimethyl-4H-pyrrolo[2,1-c][1,4]benzoxazine dihydrochloride mp: 212°–213° C.

IR (Nujol): 3320, 1703, 1616 cm$^{-1}$

NMR (DMSO-d$_6$, δ): 1.58 (6H, s), 2.80 (3H, s), 2.82 (3H, s), 4.88 (2H, br s), 6.29 (1H, d, J=3.7 Hz), 6.70 (1H, d, J=3.7 Hz), 7.31 (1H, d, J=8.5 Hz), 8.02 (1H, d, J=8.5 Hz), 8.28 (1H, s), 8.65 (2H, s), 8.84 (2H, s), 10.22 (1H, s), 12.31 (1H, s)

(+) APCI MASS (m/z): 342 [M of free compound+H]$^+$

(12) 2-[4-(Pyrrol-1-yl)benzoyl]guanidine hydrochloride mp: 267°–268° C. (dec.)

IR (Nujol): 3350, 3130, 1685, 1635, 1600 cm$^{-1}$

NMR (DMSO-d$_6$, δ): 6.32–6.38 (2H, m), 7.56–7.63 (2H, m), 7.85 (2H, d, J=8.8 Hz), 8.29 (2H, d, J=8.8 Hz), 8.63 (2H, s), 8.85 (2H, s), 12.15 (1H, s)

(+) APCI MASS (m/z): 229 [M of free compound+H]$^+$

(13) 2-[3-[(Pyrrol-1-yl)methyl]benzoyl]guanidine hydrochloride mp: 210°–212° C.

IR (Nujol): 3340, 3240, 3120, 1695, 1630, 1570 cm$^{-1}$

NMR (DMSO-d$_6$, δ): 5.19 (2H, d), 6.00–6.10 (2H, m), 6.84–6.93 (2H, m), 7.45–7.61 (2H, m), 7.99 (2H, s), 8.10 (1H, d, J=7.6 Hz), 8.57 (2H, ()), 8.77 (2H, 5), 12.10 (1H, s)

(+) APCI MASS (m/z): 243 [M of free compound+H]$^+$

Elemental Analysis Calcd. for C$_{13}$H$_{14}$N$_4$O.HCl: C 56.02, H 5.42, N 20.10 Found: C 56.31, H 5.43, N 20.01

(14) 2-[3-(Pyrazol-3-yl)benzoyl]guanidine hydrochloride mp: 259°–260° C.

IR (Nujol): 3380, 3150, 1680, 1630 cm$^{-1}$

NMR (DMSO-d$_6$, δ): 7.05 (1H, d, J=2.3 Hz), 7.64 (1H, dd, J=7.8 Hz, 7.8 Hz), 7.83 (1H, d, J=2.3 Hz), 8.08 (1H, d, J=7.8 Hz), 8.18 (1H, d, J=7.8 Hz), 8.67 (3H, s), 8.90 (2H, s), 12.23 (1H, s)

(+) APCI MASS (m/z): 230 [M of free compound+H]$^+$

(15) 2-[3-(Pyrimidin-4-yl)benzoyl]guanidine hydrochloride mp: 285°–286° C. (dec.)

IR (Nujol): 3270, 3050, 1710, 1575 cm$^{-1}$

NMR (DMSO-d$_6$, δ): 7.80 (1H, dd, J=8.0 Hz, 8.0 Hz), 8.31 (1H, d, J=8.0 Hz), 8.42 (1H, d, J=5.4 Hz), 8.57 (1H, d, J=8.0 Hz), 8.66 (2H, s), 8.84 (2H, s), 8.96 (1H, d, J=5.4 Hz), 8.98–9.02 (1H, m), 9.30–9.35 (1H, m), 12.37 (1H, s)

Elemental Analysis Calcd. for C$_{12}$H$_{11}$N$_5$O.HCl: C 51.90, H 4.36, N 25.22 Found: C 51.94, H 4.35, N 24.88

(+) APCI MASS (m/z): 242 [M of free compound+H]$^+$

(16) 2-[3-(Pyridin-2-yl)benzoyl]guanidine dihydrochloride mp: 257°–258° C.

IR (Nujol): 3400–3100 (br), 1685, 1620 cm$^{-1}$

NMR (DMSO-d$_6$, δ): 7.70–7.87 (2H, m), 8.27–8.38 (2H, m), 8.43–8.58 (2H, m), 8.76–8.94 (6H, m), 12.56 (1H, s)

(+) APCI MASS (m/z): 241 [M of free compound+H]$^+$

(17) 2-[3-(Pyridin-3-yl)benzoyl]guanidine dihydrochloride mp: 255°–256° C.

IR (Nujol): 3250–3150 (br), 1700, 1615 cm$^{-1}$

NMR (DMSO-d$_6$, δ): 7.80 (1H, dd, J=7.8 Hz, 7.8 Hz), 8.06–8.17 (1H, m), 8.18–8.30 (2H, m), 8.65–9.00 (6H, m), 9.03–9.12 (1H, m), 9.46–9.52 (1H, m), 12.66 (1H, s)

Elemental Analysis Calcd. for C$_{13}$H$_{12}$N$_4$O$_2$.HCl: C 49.86, H 4.51, N 17.89 Found: C 49.77, H 4.54, N 18.19

(18) 2-[3-(5-Aminopyrazol-1-yl)benzoyl]guanidine dihydrochloride mp: 248°–250° C.

IR (Nujol): 3400, 3270, 3150, 2700, 1705, 1685, 1625 cm$^{-1}$

NMR (DMSO-d$_6$, δ): 5.74 (1H, d, J=2.4 Hz), 7.71–7.84 (2H, m), 7.96 (1H, d, J=7.9 Hz), 8.26 (1H, d, J=7.9 Hz), 8.34 (1H, s), 8.82 (4H, s), 12.47 (1H, s)

(+) APCI MASS (m/z): 245 [M of free compound+H]$^+$

Elemental Analysis Calcd. for C$_{11}$H$_{12}$N$_6$O.2HCl: C 41.66, H 4.13, N 26.50 Found: C 41.69, H 4.53, N 26.21

(19) 2-[2-(Pyrrol-1-yl)isonicotinoyl]guanidine hydrochloride mp: 255°–256° C. (dec.)

IR (Nujol): 3350, 3120, 1700, 1620, 1560 cm$^{-1}$

NMR (DMSO-d$_6$, δ): 6.33–6.39 (2H, m), 7.76 (1H, dd, J=1.3 Hz, 5.2 Hz), 7.83–7.89 (2H, m), 8.54 (1H, d, J=1.3 Hz), 8.60–8.95 (4H, m), 8.67 (1H, d, J=5.2 Hz), 12.63 (1H, s)

(+) APCI MASS (m/z): 230 [M of free compound+H]$^+$

Elemental Analysis Calcd. for C$_{11}$H$_{11}$N$_5$O.HCl: C 49.73, H 4.55, N 26.36 Found: C 49.73, H 4.56, N 26.07

(20) 2-[[4-(Pyrrol-1-yl)pyridin-2-yl]carbonyl]guanidine hydrochloride mp: 257°–258° C. (dec.)

IR (Nujol): 3400, 1690, 1600 cm$^{-1}$

NMR (DMSO-d$_6$, δ): 6.38–6.45 (2H, m), 7.74–7.81 (2H, m), 8.07 (1H, dd, J=2.4 Hz, 5.6 Hz), 8.31 (1H, d, J=2.4 Hz), 8.75 (1H, d, J=5.6 Hz), 8.76 (2H, s), 8.84 (2H, s), 11.77 (1H, s)

(21) 2-[3-(2-cyanopyrrol-1-yl)benzoyl]guanidine isethionate mp: 149°–150° C.

IR (Nujol): 3320, 2220, 1717, 1585, 1172, 1033 cm$^{-1}$

NMR (DMSO-d$_6$, δ): 2.66 (2H, t, J=6.9 Hz), 3.64 (2H, t, J=6.9 Hz), 6.48–6.55 (1H, m), 7.27–7.33 (1H, m), 7.63–7.68 (1H, m), 7.84 (1H, dd, J=8.0 Hz, 8.0 Hz), 7.92–7.80 (1H, m), 8.01–8.09 (2H, m), 8.38 (4H, s), 11.40 (1H, s)

EXAMPLE 27

The following compound was obtained by reacting methyl 3-[[N-(2-hydroxyethyl)-N-benzyloxycarbonylamino]methyl]- 5-(pyrrol-1-yl)benzoate with guanidine hydrochloride according to similar manners to those of Examples 1, 3, 8, 10, 14 and 24.

2-[3-[(2-Oxooxazolidin-3-yl)methyl]5-(pyrrol-1-yl)benzoyl]guanidine methanesulfonate mp: 162°–163° C.

IR (Nujol) ; 3350, 3150, 1730, 1700, 1600 cm$^{-1}$

NMR (DMSO-d$_6$, δ): 2.44 (3H, s), 3.5–3.6 (2H, m), 4.3–4.4 (2H, m), 4.50 (2H, s), 6.3–6.4 (2H, m), 7.5–7.6 (2H, m), 7.69 (1H, s), 7.85 (1H, s), 8.02 (1H, s), 8.47 (4H, br s), 11.50 (1H, s)

(+) APCI MASS (m/z): 328 [M of free compound+H]$^+$

Elemental Analysis Calcd. for C$_{16}$H$_{17}$N$_5$O$_3$.CH$_4$O$_3$S: C 48.22, H 5.00, N 16.54 Found: C 48.40, H 5.10, N 16.44

EXAMPLE 28

The following compound was obtained according to a similar manner to that of Example 12.

2-[4-(Diaminomethyleneaminocarbonyl)-2-(pyrrol-1-yl)benzoyl]guanidine mp: 228°–229° C.

IR (Nujol): 3300, 1650, 1577 cm$^{-1}$

NMR (DMSO-d$_6$, δ): 6.00–6.50 (8H, br), 6.11–6.17 (2H, m), 6.93–6.99 (2H, m), 7.44 (1H, d, J=7.6 Hz), 7.90–7.99 (2H, m)

EXAMPLE 29

The following compound was obtained according to a similar manner to that of Example 20.

2-[4-(Diaminomethyleneaminocarbonyl)-2-(pyrrol-1-yl)benzoyl]guanidine dimethanesulfonate mp: 276°–278° C. (dec.)

IR (Nujol): 3350, 3110, 1725, 1710, 1660, 1605, 1250, 1405 cm$^{-1}$

NMR (DMSO-d$_6$, δ): 2.36 (6H, s), 6.28–6.34 (2H, m), 7.04–7.10 (2H, m), 7.87–8.07 (3H, m), 8.07–8.75 (8H, m), 11.53 (1H, s), 11.86 (1H, s)

(+) APCI MASS (m/z): 314 [M of free compound+H]$^+$

Elemental Analysis Calcd. for C$_{14}$H$_{15}$N$_7$O$_2$.2CH$_4$O$_3$S: C 38.02, H 4.59, N 19.40 Found: C 37.79, H 4.40, N 19.06

EXAMPLE 30

The following compounds were obtained according to similar manners to those of Examples 12 and 20.

(1) 2-[5-(2-Cyanophenyl)-3-(diaminomethyleneaminocarbonyl)benzoyl]guanidine dimethanesulfonate mp: 270°–271° C.

IR (Nujol): 3350, 1720, 1205, 1050 cm$^{-1}$

NMR (DMSO-d$_6$, δ): 2.42 (6H, s), 7.6–8.1 (4H, m), 8.44 (2H, s), 8.59 (1H, s), 8.0–8.7 (4H, br), 11.64 (1H, br)

(+) APCI MASS (m/z): 350 [M of free compound+H]$^+$

Elemental Analysis Calcd. for C$_{17}$H$_{15}$N$_7$O$_2$.2CH$_3$SO$_3$H: C 42.14, H 4.28, N 18.10 Found: C 42.07, H 4.26, N 17.77

(2) 2-[3-(Diaminomethyleneaminocarbonyl)-5-phenylbenzoyl]guanidine dimethanesulfonate mp: 265°–266° C.

IR (Nujol): 3350, 1720, 1205, 1040 cm$^{-1}$

NMR (DMSO-d$_6$, δ): 2.45 (6H, s), 7.45–7.70 (3H, m), 7.85–7.93 (2H, m), 8.40–8.80 (11H, m), 11.66 (2H, s)

(+) APCI MASS (m/z): 325 [M of free compound+H]$^+$

Elemental Analysis Calcd. for C$_{16}$H$_{16}$N$_6$O$_2$.C$_2$H$_8$S$_2$O$_6$: C 41.85, H 4.68, N 16.27 Found: C 41.69, H 4.76, N 15.93

(3) 2-[3-(3-Diaminomethyleneaminocarbonylphenyl)benzoyl]guanidine dimethanesulfonate mp: >300° C.

IR (Nujol): 3350, 3100, 1710, 1580, 1270, 1040 cm$^{-1}$

NMR (DMSO-d$_6$, δ): 2.36 (6H, s), 7.78 (2H, dd, J=7.8 Hz, 7.8 Hz), 8.00 (2H, d, J=7.8 Hz), 8.13 (2H, d, J=7.8 Hz), 8.27 (2H, s), 8.40 (8H, br s), 11.41 (2H, s)

(+) APCI MASS (m/z): 325 [M of free compound+H]$^+$

EXAMPLE 31

2M (Trimethylsilyl)diazomethane in hexane solution (0.84 ml) was added to a mixture of 2-[3-[2-((E)-2- carboxyethenyl)pyrrol-1-yl]benzoyl]guanidine (0.25 g) in tetrahydrofuran (5 ml) and methanol (5 ml) and the mixture was stirred for 25 minutes at the ambient temperature. To the reaction mixture was added acetic acid (2 ml) and stirred for 5 minutes. The mixture of ethyl acetate and water was added to the above mixture and adjusted to pH 8 with 20% aqueous potassium carbonate solution. The separated organic layer was washed with brine, dried over magnesium sulfate and evaporated in vacuo. The residue was recrystallized from a mixture of ethanol and diisopropyl ether to give 2-[3-[2-((E)-2-methoxycarbonylethenyl)pyrrol-1-yl]benzoyl]guanidine (0.15 g).

mp: 165°–168° C. (dec.)

IR (Nujol): 3270, 1690, 1620 cm$^{-1}$

NMR (DMSO-d$_6$, δ): 3.60 (3H, s), 6.00–8.20 (4H, br), 6.15 (1H, d, J=15.7 Hz), 6.34–6.40 (1H, m), 7.02–7.06 (1H, m), 7.21 (1H, d, J=15.7 Hz), 7.25 (1H, s), 7.42–7.49 (1H, m), 7.59 (1H, dd, J=7.7 Hz, 7.7 Hz), 8.01 (1H, s), 8.15 (1H, d, J=7.7 Hz)

(+) APCI MASS (m/z): 313 [M+H]$^+$

Elemental Analysis Calcd. for $C_{16}H_{16}N_4O_3$: C 61.53, H 5.16, N 17.94 Found: C 61.31, H 5.22, N 18.07

EXAMPLE 32

10% Palladium on carbon (0.2 g) was added to a solution of 2-[4-benzyloxy-3-(pyrrol-1-yl)benzoyl]guanidine (1.9 g) in methanol (20 ml) and tetrahydrofuran (20 ml) and the mixture was subjected to catalytic reduction at ambient temperature under atmospheric pressure for 30 minutes. The catalyst was removed by filtration and the filtrate was evaporated in vacuo. The residue was dissolved in methanol (15 ml) and to the solution was added a methanesulfonic acid (0.4 ml) under stirring. To the solution was added diisopropyl ether and the isolated precipitate was collected by filtration. The precipitate was recrystallized from a mixture of methanol and diisopropyl ether to give 2-[4-hydroxy-3-pyrrol-1-yl)benzoyl]guanidine methanesulfonate.

mp: 128°–133° C.

IR (Nujol): 3350, 3150, 1690, 1595, 1240, 1045 cm$^{-1}$

NMR (DMSO-d$_6$, δ): 2.39 (3H, s), 6.20–6.26 (2H, m), 7.12–7.22 (3H, m), 7.81 (1H, dd, J=2.2 Hz, 8.5 Hz), 7.90 (1H, d, J=2.2 Hz), 8.29 (4H, s), 11.17 (1H, s)

EXAMPLE 33

28% Methanolic sodium methoxide (122.2 ml) was added to a solution of guanidine hydrochloride (63.7 g) in dry N,N-dimethylformamide (300 ml) and the mixture was stirred for 20 minutes at ambient temperature. To the mixture was added methyl 3-(2-cyanopyrrol-1-yl)benzoate (30.5 g), and the mixture was stirred for 2 hours at the same temperature. The reaction mixture was poured into water under stirring. The isolated precipitate was collected by filtration to give 2-[3-(2-cyanopyrrol-1-yl)benzoyl]guanidine (21.66 g).

mp: 136°–138° C.

IR (Nujol): 3390, 2220, 1637 cm$^{-1}$

NMR (DMSO-d$_6$, δ): 6.30–6.40 (4H, br), 6.46 (1H, dd, J=2.8 Hz, 3.9 Hz), 7.24 (1H, dd, J=1.6 Hz, 3.9 Hz), 7.56 (1H, dd, J=1.6 Hz, 2.8 Hz), 7.58–7.69 (2H, m), 8.11–8.19 (2H, m)

EXAMPLE 34

Methanesulfonic acid (0.8 ml) was added to a mixture of 2-[3-(2-cyanopyrrol-1-yl)benzoyl]guanidine (2.0 g) in methanol (20 ml) and the mixture was stirred for 30 minutes at ambient temperature. To the mixture was added ethyl acetate (20 ml) and isolated precipitate was collected by filtration. The precipitate was recrystallized from water to give 2-[3-(2-cyanopyrrol-1-yl)benzoyl]guanidine methanesulfonate (1.48 g).

mp: 200°–201° C.

IR (Nujol): 3350, 3100, 2220, 1720, 1585, 1165, 1045 cm$^{-1}$

NMR (DMSO-d$_6$, δ): 2.36 (3H, s), 6.49–6.55 (1H, m), 7.27–7.33 (1H, m), 7.64–7.67 (1H, m), 7.84 (1H, dd, J=7.7 Hz, 7.7 Hz), 7.96 (1H, d, J=7.7 Hz), 8.00–8.10 (2H, m), 8.20–8.60 (4H, m), 11.42 (1H, s)

Elemental Analysis Calcd. for $C_{13}H_{11}N_5O \cdot CH_4O_3S$: C 48.13, H 4.33, N 20.05 Found: C 48.16, H 4.21, N 19.83

What we claim is:

1. A compound of the formula:

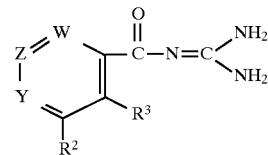

wherein

Y is C—R$^1$, wherein R$^1$ is hydrogen, lower alkyl, hydroxy, protected hydroxy, lower alkoxy, hydroxy(lower)alkyl, protected hydroxy(lower)alkyl, amino(lower)alkyl, protected amino(lower)alkyl, carboxy(lower)alkoxy, protected carboxy(lower)alkyloxy, hydroxy(lower)alkoxy, protected hydroxy(lower)alkoxy, acyl, aryl or pyrrolyl, R$^2$ is a substituted or unsubstituted heterocyclic group or heterocyclic(lower)alkyl, wherein R$^2$ excludes saturated monoheterocyclic groups bonded to the remainder of the molecule through a nitrogen heteroatom on said group, and which contain either nitrogen as the only heteroatom, two nitrogens as the only heteroatoms, one nitrogen and one oxygen as the only heteroatoms, or one nitrogen and one sulfur as the only heteroatoms, R$^3$ is hydrogen, lower alkoxy, hydroxy, protected hydroxy, or heterocyclic group, Z is C—R$^4$, wherein R$^4$ is hydrogen, carboxy, protected carboxy, nitro, halogen, hydroxy(lower)alkyl, protected hydroxy(lower)alkyl, cyano, lower alkoxy(lower)alkyl, carboxy(lower)alkenyl, protected carboxy(lower)alkenyl, hydroxy, protected hydroxy, di(lower)alkylamino(lower)alkyl, amino(lower)alkyl, protected amino(lower)alkyl, hydroxy(lower)alkoxy, protected hydroxy(lower)alkyoxy, hydroxyimino(lower)alkyl, heterocyclic group, substituted or unsubstituted heterocyclic(lower)alkyl, alkanoyl, carbamoyl which is unsubstituted or substituted with one or two substituent(s) selected from the group consisting of lower alkyl, diamino(lower)alkylidene, di(lower)alkylamino(lower)alkyl and heterocyclic(lower)alkyl, or heterocycliccarbonyl unsubstituted or substituted with hydroxy, protected hydroxy or lower alkyl; and W is C—R$^{12}$, wherein R$^{12}$ is hydrogen, lower alkoxy, nitro, hydroxy or protected hydroxy, and pharmaceutically acceptable salts thereof.

2. The compound of claim 1, wherein

Y is C—$R^1$, wherein $R^1$ is hydrogen, lower alkyl, hydroxy, phenyl(lower)alkoxy, lower alkoxy, hydroxy (lower)alkyl, acyloxy(lower)alkyl, amino(lower)alkyl, acylamino(lower)alkyl, carboxy(lower)alkoxy, esterified carboxy(lower)alkyoxy, hydroxy(lower)alkoxy, acyloxy(lower)alkyl, substituted or unsubstituted carbamoyl, phenyl or pyrrolyl, $R^2$ is substituted or unsubstituted tetrazolyl, pyrazolyl, thienyl, furyl, oxadiazolyl, thiadiazolyl, pyridyl or pyrimidinyl wherein each may be substituted by one to three substituent(s) selected from the group consisting of carboxy, protected carboxy, acyl, lower alkyl, halogen, hydroxyimino(lower)alkyl, lower alkoxyimino(lower)alkyl, di(lower)alkylamino(lower)alkyl, cyano, amino, protected amino, carboxy(lower)alkenyl, protected carboxy(lower)alkenyl, carboxy(lower)alkyl and protected carboxy(lower)alkyl;

$R^3$ is hydrogen, lower alkoxy, hydroxy, acyloxy or pyrrolyl;

Z is C—$R^4$, wherein $R^4$ is hydrogen, carboxy, esterified carboxy, nitro, halogen, hydroxy(lower)alkyl, acyloxy (lower)alkyl, cyano, lower alkoxy(lower)alkyl, carboxy(lower)alkenyl, esterified carboxy(lower)alkenyl, hydroxy, acyloxy, di(lower)alkylamino(lower)alkyl, amino(lower)alkyl, acylaminio(lower)alkyl, hydroxy(lower)alkoxy, acyloxy(lower)alkyoxy, hydroxyimino(lower)alkyl, pyrrolyl, tetrazolyl, substituted or unsubstituted oxazolidinyl(lower)alkyl, lower alkanoyl, carbamoyl which is unsubstituted or substituted with one or two substitutent(s) selected from the group consisting of lower alkyl, diamino(lower) alkylidene, di(lower)alkylamino(lower)alkyl and heterocyclic(lower)alkyl; or heterocycliccarbonyl which may be unsubstituted or substituted with hydroxy, protected hydroxy or lower alkyl; and W is C—$R^{12}$, wherein $R^{12}$ is hydrogen, lower alkoxy, nitro, hydroxy or acyloxy.

3. The compound of claim 2, wherein

Y is C—$R^1$, wherein $R^1$ is hydrogen, lower alkyl, hydroxy, benzyloxy, lower alkoxy, hydroxy(lower) alkyl, lower alkanoylamino(lower)alkyl, carboxy (lower)alkoxy, hydroxy(lower)alkoxy, diamino(lower) alkylidenecarbamoyl, phenyl or pyrrolyl;

$R^2$ is substituted or unsubstituted pyrrolyl, tetrazolyl, pyrazolyl, thienyl, furyl, oxadiazolyl, thiazolyl, pyridyl or pyrimidinyl wherein each may be substituted by one to three substituent(s) selected from the group consisting of carboxy, diphenyl(lower)alkoxycarbonyl, lower alkanoyl, carbamoyl, lower alkyl, halogen, hydroxyimino(lower)alkyl, lower alkoxyimino(lower)alkyl, di(lower)alkylamino(lower)alkyl, cyano, amino, carboxy(lower)alkenyl, lower alkyoxycarbonyl(lower) alkenyl and carboxy(lower)alkyl; or pyrrolyl(lower) alkyl;

$R^3$ is hydrogen, lower alkoxy, hydroxy or pyrrolyl; and

Z is C—$R^4$, wherein $R^4$ is hydrogen, carboxy, lower alkoxycarbonyl, nitro, halogen, hydroxy(lower)alkyl, cyano, lower alkoxy(lower)alkyl, carboxy(lower) alkenyl, hydroxy, di(lower)alkylamino(lower)alkyl, amino(lower)alkyl, hydroxy(lower)alkoxy, hydroxyimino(lower)alkyl, pyrrolyl, tetrazolyl, oxazolidinyl(lower)alkyl having oxo, lower alkanoyl, di(lower)alkylcarbamoyl; diamino(lower) alkylidenecarbamoyl, di(lower)alkylamino(lower) alkylcarbamoyl, morpholinyl(lower)alkylcarbamoyl, hydroxypiperidylcarbonyl or lower alkylpiperazinylcarbonyl.

4. The compound of claim 3, wherein

Y is C—$R^1$, wherein $R^1$ is hydrogen, lower alkyl, hydroxy, benzyloxy, lower alkoxy, hydroxy(lower) alkyl, lower alkanoylamino(lower)alkyl, carboxy (lower)alkoxy, hydroxy(lower)alkoxy, diamino(lower) alkylidenecarbamoyl, phenyl or pyrrolyl;

$R^2$ is pyrrolyl, carboxypyrrolyl, diphenyl(lower) alkoxycarbonylpyrrolyl, mono(or di)(lower) alkylpyrrolyl, hydroxyimino(lower)alkylpyrrolyl, lower alkoxyimino(lower)alkylpyrrolyl, pyrrolyl, cyanopyrrolyl, carboxy(lower)alkenylpyrrolyl, lower alkyoxycarbonyl(lower)alkenylpyrrolyl, carboxy (lower)alkylpyrrolyl, dihalopyrrolyl, pyrrolyl substituted with lower alkyl and cyano, pyrrolyl substituted with di(lower)alkylamino(lower)alkyl and cyano, pyrrolyl substituted with two lower alkyl and cyano, tetrazolyl, pyrazolyl which may be substituted with amino, thienyl which may be substituted with cyano, furyl which may be substituted with cyano, lower alkyloxadiazolyl, thiazolyl, pyridyl, pyrimidiknyl or pyrrolyl(lower)alkyl; and $R^3$ is hydrogen, lower alkoxy, hydroxy or pyrrolyl.

5. The compound of claim 4, wherein

Y is C—$R^1$, wherein $R^1$ is hydrogen;

$R^2$ is pyrrolyl, cyanopyrrolyl, hydroxyimino(lower) alkylpyrrolyl, cyanothienyl or cyanofuryl;

$R^3$ is hydrogen;

Z is C—$R^4$, wherein $R^4$ is hydrogen, nitro, hydroxy (lower)alkyl, diaminomethylenecarbamoyl, di(lower) alkylamino(lower)alkylcarbamoyl, morpholinyl(lower) alkylcarbamoyl or pyrrolyl; and W is C—$R^{12}$, wherein $R^{12}$ is hydrogen.

6. The compound of claim 5, selected from the group consisting of:

(1) 2-[3-(Pyrrol-1-yl)benzoyl]guanidine, or its hydrochloride or methanesulfonate, (2) 2-[3,5-di(Pyrrol-1-yl)benzoyl]guanidine, (3) 2-[3-Nitro-5-(Pyrrol-1-yl)benzoyl]guanidine, or its hydrochloride or methanesulfonate, (4) 2-[3-(2-Morpholinoethylcarbamoyl)-5-(Pyrrol-1-yl) benzoyl] guanidine, or its dihydrochloride, (5) 2-[3-(2-Morpholinopropylcarbamoyl)-5-(Pyrrol-1-yl) benzoyl]guanidine, or its dihydrochloride, (6) 2-[3-Hydroxymethyl-5-(Pyrrol-1-yl)benzoyl] guanidine, or its hydrochloride, methanesulfonate or isethionate, (7) 2-[3-[(2-Dimethylaminoethyl)carbamoyl]-5-(Pyrrol-1-yl)benzoyl]guanidine, (8) 2-[3-(2-Cyanopyrrol-1-yl)benzoyl]guanidine, or its hydrochloride, hemisulfate, fumarate, maleate, hemicitrate, methanesulfonate or isethionate, (9) 2-[3-(2-Cyanopyrrol-1-yl)-5-(diaminomethyleneaminocarbonyl)benzoyl]guanidine, or its methanesulfonate,

(10) 2-[3-[(Z)-2-Hydroxyiminomethylpyrrol-1-yl) benzoyl]guanidine, or its hydrochloride,

(11) 2-[3-(2-Cyanothiophen-3-yl)benzoyl]guanidine, or its methanesulfonate, and

(12) 2-[3-(2-Cyanofuran-3-yl)benzoyl]guanidine, or its methanesulfonate.

7. The compound of claim 4, wherein

Y is C—$R^1$, wherein $R^1$ is lower alkyl or hydroxy(lower) alkyl;

$R^2$ is pyrrolyl;

$R^3$ is hydrogen;

Z is C—$R^4$, wherein $R^4$ is hydrogen; and

W is C—$R^{12}$, wherein $R^{12}$ is hydrogen.

8. The compound of claim 7, selected from the group consisting of:

(1) 2-[4-n-Butyl-3-(pyrrol-1-yl)benzoyl]guanidine or its hydrochloride, and (2) 2-[4-Hydroxymethyl-3-(pyrrol-1-yl)benzoyl] guanidine or its methanesulfonate.

9. A process for preparing a pharmaceutical composition which comprises admixing a compound of claim 1 or a pharmaceutically acceptable salt thereof with a pharmaceutically acceptable carrier.

10. A pharmaceutical composition which comprises, as an active ingredient, a compound of claim 1 or a pharmaceutically acceptable salt thereof in admixture with pharmaceutically acceptable carriers.

11. A method for inhibiting $Na^+/H^+$ exchange in cells comprising treating the cells with an amount of the compound of claim 1 or a pharmaceutically acceptable salt thereof sufficient to inhibit the $Na^+/H^+$ exchange in the cells.

12. A method for the prophylactic or therapeutic treatment of cardiovascular diseases, cerebrovascular diseases, renal diseases, arteriosclerosis or shock which comprises administering a compound of claim 1 or a pharmaceutically acceptable salt thereof to human or animal.

* * * * *

UNITED STATES PATENT AND TRADEMARK OFFICE
CERTIFICATE OF CORRECTION

PATENT NO.   : 5,824,691

DATED        : October 20, 1998

INVENTOR(S)  : Kuno, et al.

It is certified that error appears in the above-identified patent and that said Letters Patent is hereby corrected as shown below:

Column 89, line 10, after "unsubstituted" insert --pyrrolyl--.

Column 89, line 20, after ";" insert --or pyrrolyl(lower)alkyl;--.

Signed and Sealed this

Ninth Day of March, 1999

*Attest:*

Q. TODD DICKINSON

*Attesting Officer*      Acting Commissioner of Patents and Trademarks